United States Patent [19]

Hoover et al.

[11] Patent Number: 4,935,405

[45] Date of Patent: * Jun. 19, 1990

[54] NOR-STATINE AND NOR-CYCLOSTATINE POLYPEPTIDES

[75] Inventors: Dennis J. Hoover, Ledyard; Robert L. Rosati, Stonington; Ronald T. Wester, Mystic, all of Conn.

[73] Assignee: Pfizer Inc., New York, N.Y.

[*] Notice: The portion of the term of this patent subsequent to Mar. 21, 2006 has been disclaimed.

[21] Appl. No.: 277,614

[22] Filed: Nov. 29, 1988

Related U.S. Application Data

[60] Division of Ser. No. 112,976, Oct. 23, 1987, Pat. No. 4,814,342, which is a continuation-in-part of Ser. No. 68,982, Jul. 1, 1987, abandoned, which is a continuation-in-part of Ser. No. 925,449, Oct. 31, 1986, abandoned.

[51] Int. Cl.$^5$ .................... A61K 31/42; C07D 265/30; C07C 5/08

[52] U.S. Cl. ........................................ 514/19; 514/18; 514/385; 530/330; 530/331; 544/159

[58] Field of Search .......................... 514/18, 19, 385; 530/330, 331; 544/159

[56] References Cited

U.S. PATENT DOCUMENTS 4,814,342  3/1989  Hoover et al. ...................... 514/385

*Primary Examiner*—Lester L. Lee
*Attorney, Agent, or Firm*—Peter C. Richardson; J. Trevor Lumb; James M. McManus

[57] ABSTRACT

Polypeptides and derivatives thereof containing nor-statine and nor-cyclostatine are useful for inhibiting the angiotensinogen-cleaving action of the enzyme renin.

12 Claims, No Drawings

NOR-STATINE AND NOR-CYCLOSTATINE POLYPEPTIDES CROSS-REFERENCE TO RELATED APPLICATIONS

This application is a divisional application of copending application Ser. No. 112,976, filed Oct. 23, 1987, now U.S. Pat. No. 4,814,342, which is a continuation-in-part of copending application Ser. No. 68,982, filed July 1, 1987, now abandoned which is a continuation-in-part of copending application Ser. No. 925,449 filed Oct. 31, 1986, now abandoned.

BACKGROUND OF THE INVENTION

This invention relates to novel nor-statine and nor-cyclostatine containing polypeptides useful and antihypertensive agents.

The proteolytic enzyme renin, which has a molecular weight of about 40,000, is produced in and secreted into the blood by the kidney. It is known to be active in vivo in cleaving the naturally-occurring plasma glycoprotein angiotensinogen, in the case of human angiotensinogen at the bond between the leucine (10th) and valine (11th) amino acid residues at the N-terminal end of the angiotensinogen:

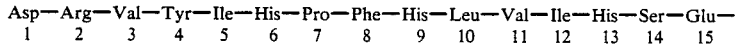

Asp—Arg—Val—Tyr—Ile—His—Pro—Phe—His—Leu—Val—Ile—His—Ser—Glu—
  1     2     3    4    5    6    7    8    9   10   11   12   13   14   15

The circulating N-terminal decapeptide (angiotensin I) formed by the above cleaving action of renin is subsequently broken down by the body to an octapeptide known as angiotensin II. Angiotensin II is known to be a potent pressor substance, i.e. a substance that is capable of inducing a significant increase in blood pressure and is believed to act by causing the constriction of blood vessels and the release of the sodium-retaining hormone aldosterone from the adrenal gland. Thus, the renin-angiotensinogen system has been implicated as a causative factor in certain forms of hypertension and congestive heart failure.

One means of alleviating the adverse effects of the functioning of the renin-angiotensinogen system is the administration of a substance capable of inhibiting the angiotensinogen-cleaving action of renin. A number of such substances are known including antirenin antibodies, pepstatin and naturally-occurring phospholipid compounds. European Patent Application No. 45,665 (published Feb. 2, 1982) discloses a series of renin-inhibiting polypeptide derivatives of the formula X-Y-Pro-Phe-His-A-B-Z-W in which X may be hydrogen or an amino-protecting group, Y may be absent, B is a lipophilic amino acid residue, Z is an aromatic amino acid residue, W may be hydroxyl and A may be, inter alia,

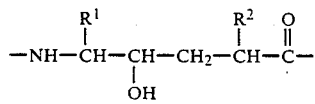

with each of $R^1$ and $R^2$ being a lipophilic or aromatic side chain. According to the definitions set forth in this published patent application, it is not contemplated that either A or Z could be statine or that B could be lysine.

European Patent Application No. 77,028A (published Apr. 20, 1983) discloses a series of renin-inhibiting polypeptide compounds having a non-terminal statine or statine derivative residue. Included within this series are compounds having a phenylalanine-histidine-statine sequence.

European Patent Application No. 132,304A also discloses the use of statine containing polypeptides as renin-inhibiting antihypertensive agents, and European Patent Application No. 114,993A discloses polypeptides containing cyclostatine, useful as renin-inhibiting antihypertensive agents.

SUMMARY OF THE INVENTION

The novel peptides of the present invention are of the formulae

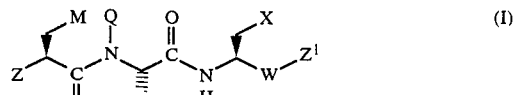

and

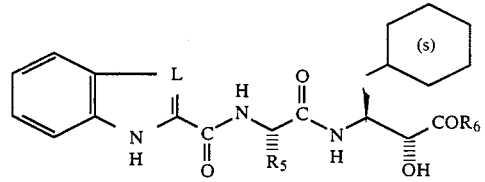

and a pharmaceutically acceptable salt thereof, wherein Z is $R_1-(Y)_m-(A)_p$, where $R_1$ is $(C_1-C_6)$alkyl, amino, $(C_1-C_4)$alkoxy, $(C_1-C_4)$alkylamino, $(C_1-C_3)$alkoxy($C_2-C_4$)alkyleneamino, carboxy$(C_1-C_4)$alkyl, hydroxy($C_2-C_4$)alkyleneamino, $(C_1-C_3)$alkoxyCOCH$_2$N(CH$_3$), amino$(C_1-C_5)$alkyl, morpholino, piperidyl, hydroxypiperidino, 4-oxopiperidino, piperazino, 4-oxopiperidinoethylene ketal, 4-$(C_1-C_3)$alkylpiperazino, thiomorpholino, thiomorpholino 1-oxide, thiomorpholino 1,1-dioxide, N-$(C_1-C_4)$alkoxycarbonylpiperidyl, 4-$(C_1-C_4)$alkoxycarbonylpiperazino, 3-oxomorpholino, 3,5-dioxomorpholino, hydroxypyridyl, pyridyl, (s)-pyrrolid-2-yl, N-t-butoxycarbonyl-(S)-pyrrolid-2-yl, 2-$(C_1-C_3)$alkoxycarbonyl-(S)-pyrrolid-2-yl or 4-$(C_1-C_4)$alkanoylpiperazino; Y is C=O, P(OCH$_3$)=O or SO$_2$l A is NH, NCH$_3$ or O; m and p are each integers of 0 or 1; M is phenyl, naphthyl, benzyl, thienyl, methoxyphenyl, hydroxyphenyl, chlorophenyl or $(C_6-C_7)$cycloalkyl; Q is methyl or hydrogen; $R_2$ is $(C_1-C_5)$alkyl, $(C_1-C_3)$alkylthio$(C_1-C_2)$alkyl, $(C_1-C_3)$alkoxy($C_1-C_2$)alkyl, benzyloxy$(C_1-C_2)$alkyl, benzyl, hydroxy($C_1-C_2$)alkyl, carboxy$(C_1-C_2)$alkyl, guanido$(C_1-C_3)$alkyl, $(C_1-C_3)$alkylsulfinyl$(C_1-C_2)$alkyl, $(C_1-C_3)$alkylsulfonyl$(C_1-C_2)$alkyl, 4-benzyloxycarbonylaminobutyl, 4-aminobutyl, imidazol-4-ylmethyl, N-t-butoxycarbonylimidazol-4-ylmethyl or carbamyl$(C_1-C_2)$alkyl; X is cyclohexyl, i-propyl or phenyl; W is CH⫿OCO($C_1-C_3$)alkylpiperidino, CH⫿OH, CH⫿OCO($C_1-C_3$)alkyldi($C_1-C_2$)alkylamino, C=O, CH⫿N$_3$, CH◂N$_3$, CH◂NH$_2$, CH⫿NH$_2$, C(CH$_3$)⫿OH, C(CH$_3$)◂OH, CH⫿OCO($C$-

$_1$-C$_2$)alkyl or CH⫶OCO(C$_1$-C$_2$)alkylene CO$_2$H; Z$^1$ is CH$_2$OH or R—S—T where R is C=O, S is O, NH, N(CH$_3$), CH$_2$ or a chemical bond linking R and T; T is (C$_1$-C$_5$)alkyl, hydroxy(C$_1$-C$_4$)alkyl, CONH-(C$_1$-C$_4$)alkyl, hydrogen, trifluoroethyl, (C$_6$-C$_7$)cycloalkyl, (C$_6$-C$_7$)cycloalkylmethyl, phenyl, benzyl, amino(C$_2$-C$_5$)alkyl, O-(C$_1$-C$_2$)alkyl hydroxylamino, morpholino, 4-(C$_1$-C$_2$)alkylpiperazino or omega-di(C$_1$-C$_2$)alkylamino(C$_3$-C$_5$)alkyl; L is CH or N; R$_5$ is imidazol-4-ylmethyl or (C$_2$-C$_5$)alkyl; and R$_6$ is (C$_1$-C$_4$)alkoxy or (C$_1$-C$_4$)alkylamino with the provisos that when m is 0, p is 0; when A is O, Y is C=O; when T is CONH-(C$_1$-C$_4$)alkyl, S is NH, N(CH$_3$) or CH$_2$; and when T is (C$_2$-C$_5$)alkylamino, O-(C$_1$-C$_2$)alkyl hydroxylamino, morpholino or 4-(C$_1$-C$_2$)alkylpiperazino, S is CH$_2$ or a chemical bond linking R and T.

A preferred group of compounds are those of formula I, wherein Y is C=O, A is NH, Q is hydrogen, X is cyclohexyl, W is CH OH, R is C=O, T is benzyl or (C$_1$-C$_5$)alkyl and m and p are each 1. Especially preferred within this group are compounds where R$_1$ is morpholino, M is phenyl, S is O and R$_2$ is n-propyl and T is i-propyl, where R$_2$ is CH$_3$SCH$_2$— and T is i-propyl, where R$_2$ is n-butyl and T is methyl, where R$_2$ is HOCH$_2$ and T is i-propyl, where R$_2$ is CH$_3$O(CH$_2$)$_2$— and T is i-propyl, where R$_2$ is CH$_3$SCH$_2$— and T is benzyl, where R$_2$ is methyl and T is i-propyl, where R$_2$ is n-butyl and T is i-propyl, where R$_2$ is CH$_3$OCH$_2$— and T is i-propyl and where R$_2$ is CH$_3$CH$_2$OCH$_2$— and T is i-propyl. Also especially preferred within this group are compounds M is phenyl, S is O, T is i-propyl, R$_2$ is CH$_3$SCH$_2$— and R$_1$ is pyrrolidyl, 4-pyridyl, piperazino, 4-oxopiperidino or 4-hydroxypiperidino. Also especially preferred within this group are those compounds where R$_1$ is morpholino, M is phenyl, S is a chemical bond linking R and T and R$_2$ is n-butyl and T is CH$_2$CH(CH$_3$)$_2$, and where R$_2$ is CH$_3$SCH$_2$ and T is CH$_2$CH(CH$_3$)$_2$. Also especially preferred within this group are compounds where R$_1$ is morpholino, S is O and where M is 2-thienyl, R$_2$ is CH$_3$SCH$_2$ and T is i-propyl, where M is 4-hydroxyphenyl, R$_2$ is CH$_3$SCH$_2$— and T is i-propyl and where M is 4-methoxyphenyl, R$_2$ is n-butyl and T is methyl. Also especially preferred in this group is the compound where R$_1$ is morpholino, M is phenyl, R$_2$ is n-butyl, S is NH and T is methyl.

A preferred group of compounds are those of formula I where M is phenyl, S is a chemical bond linking R and T, T is (C$_1$-C$_5$)alkyl and R is C=O.

The present invention also includes a method for treating hypertension in a mammal which comprised administering to said mammal an antihypertensive effective amount of the compounds of the present invention and a pharmaceutical composition comprised of the compounds of the present invention and a carrier.

As previously indicated, the present invention embraces pharmaceutically acceptable salts of the biologically active compounds. Such salts are those which are non-toxic at the dosages administered. Since compounds of the invention may contain basic groups, acid addition salts are possible. Pharmaceutically acceptable acid addition salts include e.g. the hydrochloride, hydrobromide, hydroiodide, sulfate, bisulfate, phosphate, acid phosphate, acetate, lactate, maleate, mesylate, fumarate, citrate, acid citrate, tartrate, bitartrate, succinate, gluconate and saccharate salts.

In the interest of brevity, the commonly accepted abbreviated name of the individual amino acids and reagents have been employed where possible. For example, the amino acid phenylalanine is abbreviated as Phe, Hse as homoserine, histidine as His, lysine as Lys, and norleucine as Nle. The amino protecting group t-butoxycarbonyl is abbreviated as Boc, benzyloxycarbonyl as CBZ and N-t-butoxycarbonyl on the imidazole of histidine as imBoc. Other abbreviations include: CPBA-chloroperbenzoic acid, DCC-dicyclohexylcarbodiimide, DEC-dimethylaminopropyl ethyl carbodiimide-HCl, DMF dimethylformamide, HCl-hydrogen chloride, HBT hydroxybenzotriazole, mesyl-CH$_3$SO$_2$—, thala-2thienylalanine, Nphala-1-naphthylalanine, TBDMS-t-butyldimethylsilyl, TEA triethylamine, S-MeCys-S-methyl cysteine, S-EtCys-S-ethyl cysteine, MgSO$_4$-magnesium sulfate, NaOH sodium hydroxide, CH$_2$Cl$_2$-methylene chloride, K$_2$CO$_3$-potassium carbonate, NaHCO$_3$-sodium bicarbonate, O-MeTyr-O-methyl tyrosine, O-MeHse-O-methyl-homoserine, etc.

The modified statine and cyclostatine containing one less carbon atom in the structure of statine and cyclostatine and are of the formulae

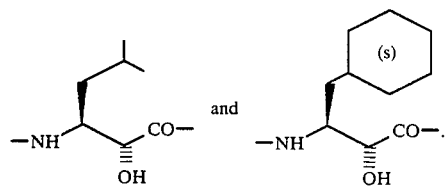

These structures are abbreviated as nor-Sta and nor-C-Sta, respectively.

All the natural amino acid contained in the structures of the instantly claimed compounds are of the L configuration, the naturally occurring configuration, unless otherwise noted.

Also considered as part of the present invention are compounds of formulae I and II wherein nor-Sta and nor-C-Sta are replaced with nor-Statone and nor-C-Statone.

DETAILED DESCRIPTION OF THE INVENTION

The compound of this invention exhibit antihypertensive activity in vivo in mammals, including humans. At least a substantial portion of this activity results from their ability to inhibit the cleavage of angiotensinogen by renin. Although we do not wish to be limited by the following theory of mechanism, it is likely that the mechanism of the renin-inhibiting activity of the compounds of the invention is their selective binding (as compared to angiotensinogen) to renin. The compounds of the invention exhibit an enzyme-inhibiting activity that is selective for renin. Because of their low molecular weights they exhibit favorable solubility characteristics in aqueous media, thus making oral administration feasible, and can be synthesized at a commercially realistic cost. The compounds of the present invention are also useful against congestive heart failure.

The compounds of the invention may be prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end as described herein. The amino acids utilized to synthesize the compounds of the present invention are commercially available (as free acids, salts or esters, etc.) in both alpha-amino protected and alpha-amino unprotected forms.

The activity of the compounds of the present invention as inhibitors of the angiotensinogen-cleaving activity of renin may be determined by studying their ability to inhibit the angiotensinogen-cleaving activity of renin in vitro.

The compounds of the present invention can be administered as antihypertensive agents by either the oral or parental routes of administration, with the former being preferred for reasons of patient convenience and comfort. In general, these antihypertensive compounds are normally administered orally in dosage ranging from about 0.1 mg to about 20 mg per kg of body weight per day and 0.1 mg to about 5 mg per kg of body weight per day when given parenterally; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

The novel compounds of the invention can be orally administered in a wide variety of different dosage forms, i.e., they may be formulated with various pharmaceutically acceptable inert carrier in the form of tablets, capsules, lozenges, troches, hard candies, powders, sprays, aqueous suspensions, elixirs, syrups and the like. Such carriers included solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatin and acacia Additionally, lubricating agents such as magnesium stearate, sodium lauryl sulfate and talc are compositions of a similar type may also be employed as fillers in soft and hard-filled gelatin capsules; included lactose or milk sugar as well as high molecular weight polyethylene glycols. When aqueous suspensions and/or elixirs are desired of oral administration, the essential active ingredient therein may be combined with various sweetening or flavoring agents, coloring matter or dyes and, if so desired, emulsifying and/or as water, ethanol, propylene glycol, glycerin and various like combinations thereof.

The compounds of the present invention are also useful in the diagnosis of hypertension and congestive heart failure.

The following examples illustrate the invention but are not to be construed as limiting the same.

General Experimental

High performance liquid chromatography (HPLC) was performed with the following conditions: 214 nm detection, 4.6×250 mm Dupont Zorbax C-8 column at 1.5 ml/min. TLC systems are, where abbreviated, as follows: System A=ethyl acetate-hexane, respectively, in the ratio indicated, on silica; System B=ether-hexane, respectively, in the ratio indicated, on silica; System C=18/2/1 $HCCl_3$-EtOH-HOAc on silica, System D=9:2:1 chloroform-ethanol-acetic acid.

EXAMPLE 1

BocPheHisnor-C-StaNHCH$_3$ (I,
Z=t-butoxycarbonylamino; M=phenyl; Q=H;
R$_2$=imidazol-4-ylmethyl; W=CH$\,$⫼$\,$OH;
Z$^1$=CONHCH$_3$; and X=cyclohexyl)

A.
N-Methyl-(S)-3-t-Boc-amino-4-cyclohexyl-(R)-2-hydroxybutyramide (S)-3-t-Boc-amino-4-cyclohexyl-(R)-2-hydroxybutyric acid (100 mg), U.S. Pat. No. 4,599,198, was dissolved in 0.9 mL tetrahydrofuran with 55 uL triethylamine and the mixture was treated at −30° C. with isobutyl chloroformate (45 uL). After 1.5 h the mixture was cooled to −60° C. and 1.5 mL of a 1.6M solution of methylamine in tetrahydrofuran was added, and the mixture was brought to 25° C. Excess methylamine was bubbled in to the reaction mixture which was then diluted with 25 mL ether, extracted twice with a saturated sodium bicarbonate solution, dried, and concentrated. Chromatography in 2:1 ethyl acetate-hexanes on silica gave 45 mg (42%) of the title substance as a colorless solid, Rf 0.16 in 2:1 ethyl acetate-hexanes, silica, and RP-HPLC, 40/60 MeCN-pH 2.1 0.1M phosphate, 3.32 min.

B.
N-Methyl-(S)-3-amino-4-cyclohexyl-(R)-2-hydroxybutyramide

The product from Example IA (45 mg) was dissolved in 2 ml 4N hydrogen chloride-dioxane and stirred at 25° C. for 1.5 h. The mixture was concentrated and co-evaporated several times with ether giving 50 mg of the title substance as a colorless solid, HPLC retention time 3.05 min., 40/60 MeCN-pH 7.0 0.1M phosphate.

C. BocPheHis(imBoc)nor-C-StaNHCH$_3$

A solution of the product of Example IB (49 mg) in 0.5 mL dichloromethane was treated at 0° C. with 30 uL triethylamine, 112 mg BocPheHis(imBoc), U.S. Pat. No. 4,599,198, 48 mg of hydroxybenzotriazole and 46 mg of dicyclohexylcarbodiimide respectively, and the mixture was stirred at 0° C. for 6 h, then allowed to warm to 25° C. overnight. The mixture was filtered, the precipitate washed with dichloromethane and the combined filtrates concentrated and dissolved in ethyl acetate. After stirring a few minutes the ethyl acetate suspension was filtered, and the filtrate was washed with 1N sodium hydroxide solution (twice), dried over magnesium sulfate, and concentrated. Chromatography on silica eluting with ethanol-dichloromethane stepwise increased in polarity as follows (1%, 2%, 4%, 6%, and 10% ethanol) gave 57 mg of the title substance as a colorless amorphous solid.

D. BooPheHisnor-C-StaNHCH$_3$

The product of Example IC was dissolved in 1.2 mL of 80/20 (V:V) acetic acid-water and stirred at 25° C. for 12 h. The mixture was concentrated, co-evaporated three times with ether and twice with dichloromethane giving 47 mg of a product as a light brown powder.

HPLC, in 50/50 MeCN-pH 2.1 0.1M phosphate, 3.61 min.; 1H NMR, DMSO, 300 MHz, partial, delta ppm: 1.32 (s, 9H, Boc), 2.60 (d, 3H, NCH$_3$), 3.90, 4.66 and 7.9 (m, 1H ea), 4.18 (m, 2H), 7.12, 7.7, 8.28 (d, 1H ea), 7.32 (s, 1H), 7.2–7.4 (m, aromatic).

EXAMPLE 2

BocPheHisnor-C-StaNHCONHCH$_2$CH$_2$CH$_3$ (I, Z=t-butoxycarbonylamino; R$_2$=imidazol-4-ylmethyl; M=phenyl; Q=H; W=CH$_{\text{IIIIIII}}$OH; Z$^1$=CONHCONHCH$_2$CH$_2$CH$_3$; and X=cyclohexyl)

A. N-t-Boc-O-t-butyldimethylsilyl-nor-C-staNHCONHCH$_2$CH$_2$CH$_3$

A solution of 415 mg (S)-3-t-Boc-amino-(R)-2-t-butyldimethylsilyloxy-4-cyclohexylbutyramide (U.S. Pat. No. 4,599,198) and 94 uL propyl isocyanate in 2 mL toluene was heated 90 h at 100° C., cooled, and chromatographed on silica in 15% ethyl acetate-hexane, giving 260 mg of the title substance as a colorless oily foam, TLC Rf 0.49, 1:2-system A.

B. Nor-C-StaNHCONHCH$_2$CH$_2$CH$_3$ hydrochloride

The product of Example 2C (255 mg) was dissolved in at 25° C. in 3 mL of a solution of freshly prepared 5% aqueous 48% hydrofluoric acid in acetonitrile, and stirred for 2 h. Excess sodium bicarbonate was added to the reaction mixture, along with 20 mL water and the mixture was extracted with ethyl acetate, which was then washed with water, dried (magnesium sulfate), and concentrated to give 198 mg of an oil. This was dissolved at 0° C. in 4 mL 4N hydrogen chloride-dioxane, stirred at 25° C. for 1 h, then concentrated to give 130 mg of a colorless waxy solid. NMR indicated that cleavage of the silyl group was incomplete. TLC showed two products of Rf 0.42 and 0.07 (System C) assumed to be the aminosilyl ether and aminoalcohol, respectively. This product was used without purification in the following step.

C. BocPheHis(imBoc)nor-C-StaNHCONHCH$_2$CH$_2$CH$_3$

According to the procedure for preparation and purification of the product of Example IC, 119 mg of the product of Example 2B gave 97 mg of the title substance as a colorless amorphous solid, TLC Rf 0.55, system C. The undesired corresponding O-silylated substance (derived from the O-silyl contaminant in Example 2B) was separated during the chromatographic step (a less polar substance, Rf 0.60, system C).

D. BocPheHisnor-C-StaNHCONHCH$_2$CH$_2$CH$_3$

The product of Example 2C (91 mg) was dissolved in 1.5 mL 80/20 acetic acid-water and stirred at 25° C. for 6 h. The mixture was concentrated, co-evaporated with ether three times and dried overnight to give 80 mg of product as a colorless solid, Rf 0.10 in system C and having an HPLC retention time of 2.35 min. in 70/30 MeCN-pH 2.1 0.1M phosphate.

NMR, DMSO, 250 MHz, partial delta, ppm: 0.86 (t, 3H), 1.32 (s, 9H, Boc), 1.47 (q, 2H), 3.14 (q, 2H), 4.06 and 4.48 (m, 1H ea), 4.17 (m, 2H), 6.83 (s, 1H), 7.10, 7.63, 8.02 (d, 1H ea), 7.15–7.35 (m, aromatic), 7.56 (s, 1H), 8.28 (m, 1H).

EXAMPLE 3

Indole-2-carbonylHisnor-C-Sta methyl ester (II, R$_5$=imidazol-4-ylmethyl; R$_6$=OCH$_3$; and L=CH)

A. 4-Cyclohexyl-2-pentyn-1-yl tetrahydropyran-1-yl ether

An oven-dried 5 L three-necked roundbottomed flask equipped with mechanical stirrer, thermometer, dropping funnel and nitrogen inlet was charged with 192 g propargyl tetrahydropyranyl ether and 750 mL dry tetrahydrofuran (Aldrich gold label). The stirred solution was maintained at 0° C. with a Dry Ice-acetone bath while 604 mL 2.5M n-butyllithium was added over 45 min. To the resulting dark solution was added a solution of cyclohexylmethyl bromide in hexamethylphosphoramide (distilled from calcium hydride at reduced pressure) over a period of 20 min. at 5°–10° C., and stirring was continued 4 h at 25° C. The mixture was poured into a stirred mixture of 2 L ice-water and 2 L hexane. The organic layer was washed with 2×500 mL 1.0M lithium chloride solution, dried over sodium sulfate, concentrated, and distilled using an 8" Vigreux column to give 102 g recovered propargyl tetrahydropyranyl ether, bp. 60°–90° C. at 3 mm, followed by 151 g of the title product, bp 125°–130° C. at 0.5 mm, TLC Rf 0.5 in 1:4 system B.

B. 4-Cyclohexyl-2-butyn-1-ol

A 2 L three-necked flask equipped with mechanical stirrer, nitrogen inlet, and thermometer was charged with 140 g of the product of Example 3A and 700 mL methanol. The stirred mixture was cooled to 2°–3° C. and 560 mg p-toluenesulfonic acid was added, where upon the cooling bath was replaced with a bath of warm water sufficient to raise the reaction temperature to 30° C. After 4.5 h 5 mL 1N sodium hydroxide solution was added and most of the methanol was removed at reduced pressure on the rotary evaporator. The residue was dissolved in 700 mL hexane and the solution was washed with 1N sodium hydroxide solution (3×100 mL), dried over potassium carbonate, filtered, concentrated and distilled from potassium carbonate using an 8" Vigreux column to give 76 g of product bp 90° C. at 1 mm as a light yellow liquid, contaminated by 1% methanol and 1% hexamethylphosphoramide as judged by 1H NMR. This product was used in the next step without additional purification. TLC Rf 0.5, 1:1 system B.

Anal. Calcd for C$_{10}$H$_{16}$O: C, 78.90; H, 10.59. Found: C, 78.31; H, 10.72.

C. Z-4-Cyclohexyl-2-buten-1-ol

A 500 mL Parr bottle was charged with 35.2 g of the product of Example 3B, 250 mL toluene, 250 mg "Lindlar Catalyst Poison" (Fluka). The solution was purged with nitrogen and 14.08 g Lindlar catalyst (Aldrich) was added. The mixture was shaken under 35 psi. hydrogen pressure for 45 minutes, during which time the reaction temperature increased spontaneously to about 45° C. The cooled suspension was filtered through Celite and was combined with another reaction mixture prepared in an identical manner from another 5.2 g of the same starting material. The combined mixture was concentrated by distillation at atmospheric pressure from calcium carbonate through a 12″ Vigreux column, then on the rotary evaporator at aspirator pressure and 25° C., followed by heating at 80° C. at 0.3 mm in the same flask equipped with a Vigreux column until gentle reflux was achieved. The remaining liquid, a light yellow oil, weighed 77.4 g, and was contaminated with 1% methanol and 1% hexamethylphosphoramide as judged by NMR. This product showed a single spot by TLC, Rf 0.4, 1:1, system B and by NMR showed no detectable trans isomer.

D. 2(S), 3(R)-Epoxy-4-cyclohexyl-1-butanol

A 1 L three-necked flask equipped with thermometer, mechanical stirrer, nitrogen inlet and cooling bath was charged with 15 g 4 anstrom 600-mesh molecular seives, 400 mL dichloromethane, and 7.23 mL (+)-diisopropyl L-tartrate (Aldrich). The stirred mixture was cooled to −5° C. and 6.75 mL titanium tetraisopropoxide was added, followed by 227 mL 3.0M t-butyl hydroperoxide in toluene (Aldrich), neither of which produced appreciable exotherm. To the stirred mixture at −20° C. was added a solution of 70 g of the product of Example 3C in 30 mL dichloromethane over 10 min. so that the temperature did not rise about −20° C. The mixture was stirred 6 h at −10° C., then placed (without stirring) in a refrigerator (−10° C.) for 60 h. The mixture was again stirred in an ice bath and 120 mL water was added, followed by 30 mL 6N sodium hydroxide solution and the mixture was saturated with sodium chloride. Methanol (50 mL) was added and the mixture was filtered, treated with 100 mL 0.1M pH 7 phosphate buffer and after vigorous shaking was allowed to stand until partial separation occurred. The lower (organic) layer was separated, and the top (aqueous) and middle (emulsion) layers were extracted with dichloromethane (3×200 mL). The remaining emulsion (middle layer) was filtered through Celite, causing its complete separation into organic and aqueous layers. The combined organic layers were washed with pH 7 phosphate buffer (3×100 mL), aqueous bicarbonate, brine, dried (magnesium sulfate), filtered and concentrated to give 85 g of a viscous oil which was distilled using an 8″ Vigreux column to give 12 g, bp 60°-122° C. at 0.5 mm, then 51 g of the title substance, bp 122°-130° C. at 0.45 mm, TLC Rf 0.20 in 2:1, system B.

Anal. Calcd for $C_{10}H_{18}O_2$: C, 70.55; H, 10.66. Found: C, 69.89; H, 10.50.

E. 2(S), 3(R)-epoxy-4-cyclohexyl-1-butanoic Acid

Three grams of the product of Example 3D was dissolved in acetonitrile (30 mL), and 45 mL water, 30 mL carbon tetrachloride, 690 mg ruthenium trichloride trihydrate, and 10.0 g periodic acid were added sequentially. The temperature gradually rose but was maintained at 30°-35° C. with gentle cooling. After 1.5 h 75 mL brine and 400 mL chloroform were added. The organic layer was separated and the aqueous was extracted three times with chloroform (400 mL). The combined organic layers were washed with 50 mL 2N hydrochloric acid saturated with sodium chloride, dried (magnesium sulfate), filtered through Celite and concentrated to give 2.55 g of the title substance as a purple solid, TLC Rf 0.40, system C, which was immediately used without purification in the next step.

F. 3(S)-Azido-2(R)-hydroxy-4-cyclohexylbutyric Acid

The product of Example 3E (2.65 g) was dissolved in 10 mL absolute ethanol and added at 25° C. to a stirring solution of 2.11 g lithium azide and 6.43 mL titanium tetraisopropoxide in 180 mL absolute ethanol. The mixture was stirred at 25° C. for 20h then at 35° C. for 5 h and 25° C. for 14 h, whereupon it was concentrated, dissolved in 250 mL ether and 75 mL 1% sulfuric acid, stirred 30 min. and separated. The resulting organic layer was washed with 5% sulfuric acid (3×20 mL), pH 7 phosphate buffer (twice), dried (magnesium sulfate) and concentrated to give 2.82 g of the title substance as a light tan oil which solidified on standing. The material showed TLC Rf 0.35 (system C) and IR (CHCl$_3$) 2100 cm$^{-1}$.

G. 3(S)-Azido-2(R)-hydroxy-4-cyclohexylbutyric acid methyl ester

Diazomethane was prepared by treating 4.5 g of N′-nitroso-N-methyl-N-nitroguanidine in 75 mL ether with 31 mL 6N sodium hydroxide solution at 0° C., followed by decanting and drying the organic layer briefly over 5 g potassium hydroxide. This solution was placed in a dropping funnel and added dropwise to a stirred solution of 2.82 g of the product of Example 3F in 50 mL ether at 0° C. After 40 min. 20 mL acetic acid was added, and the mixture was extracted with saturated sodium bicarbonate (3×20 mL), sodium hydroxide solution (2×20 mL), dried (sodium sulfate), filtered and chromatographed on silica eluting with 1:8 ethyl acetate-hexane. 2.43 g of the title substance was obtained by concentrating the appropriate fractions and showed TLC Rf 0.58, 1:1 system A, IR (CHCl$_3$) 2100 cm$^{-1}$ [alpha]$_D^{20}$+10.1, (c=1.19, CHCl$_3$).

H. (S)-Amino-2(R)-hydroxy-4-cyclohexylbutyric acid methyl ester hydrochloride The product of Example 3G (2.23 g) was shaken with 100 mg 10% Pd/C in 15 mL ethanol and 0.4 mL acetic acid under 50 psi hydrogen for 40 min. at 25° C. The mixture was filtered through Celite, concentrated, co-evaporated with toluene (2×10 mL), dissolved in 4 mL 3.4M hydrogen chloride-dioxane, concentrated and co-evaporated several times with ether to give after drying 1.49 g of an oily light yellow foam, TLC Rf 0.15 (the spotted plate was exposed to ammonia vapor prior to development in system C).

I. Indole-2-carbonylHis methyl ester

Five and a half grams of histidine methyl ester dihydrochloride was suspended in 500 mL dichloromethane and treated at 0° C. with 6.92 mL triethylamine, followed sequentially by 4.2 g indole-2-carboxylic acid, 5.56 g hydroxybenzotriazole and 5.35 g of dicyclohexylcarbodiimide. The mixture was stirred in an ice bath which was allowed to warm to 25° C. overnight. The mixture was filtered, the precipitate washed with dichloromethane, the filtrate concentrated, the residue dissolved in 200 mL chloroform and extracted with 4×30 mL 1N sodium hydroxide solution, brine, dried (sodium sulfate) and concentrated to give 7.2 g of a yellow foam. This foam was dissolved in a mixture of 5 mL chloroform, 20 mL water, 25 mL 1N hydrochloric acid, the aqueous layer washed with 5 mL chloroform and then adjusted to pH 6 with sodium hydroxide solution. The mixture was concentrated and dried to give 4.3 g of a light green solid, showing 3.46 min. retention time by HPC in 35/65 MeCN-pH 2.1 0,1M phosphate (85% of total absorption), with minor contaminants at 2.36 and 1.66 min. TLC Rf in system C was 0.07. This product was used in the next step without additional purification.

J. N-alpha-(Indole-2-carbonyl)-N(im)-t-butoxycarbonyl-L-histidine

Four and three-tenths grams of the product of Example 3I was dissolved in 60 mL methanol and 20 mL water, cooled to 0° C. and treated with 7.6 g anhydrous potassium carbonate. After 1 h at 0° C. and 2 h at 25° C., the mixture was cooled, taken to pH 3 with 6N hydrochloric acid, concentrated, cooled to 0° C., brought to pH 10.5 with 6N sodium hydroxide solution, treated with 150 mL dioxane and at 0° C. 4.2 mL di-t-butyl dicarbonate ((Boc)$^{20}$) was added The mixture was then allowed to stir at 25° C. and the pH was kept between 9 and 10.5 by addition of 6N sodium hydroxide solution. After 75 min. 2 mL more (Boc)$^{20}$ was added, and after an additional 15 min. the mixture was concentrated to remove most of the dioxane, 100 mL water was added, and the resulting solution was washed three times with ether (25 mL ea.). The aqueous layer was cooled in an ice bath, 500 mL ethyl acetate was added and the pH of the aqueous layer was brought to 1.3 with 6N hydrochloric acid. The organic layer was separated, the aqueous extracted with ethyl acetate, the organic layers combined, washed with brine, dried (sodium sulfate), filtered and concentrated to give after drying 3.1 g of the title substance as a dry yellow powder, HPLC in 50/50 MeCN-pH 2.1 0.1M phosphate 4.57 min. (93% of the total UV integration) and [alpha]$_D^{20}$ +10.5° (c=0.88, CHCl$_3$).

K. Indole-2-carbonylHis(imBoc)nor-C-Sta methyl ester

According to the procedure for the preparation and purification of the product of Example 1C, 500 mg of the product of Example 3H was coupled in 25 mL dichloromethane with 911 mg of the product of Example 3J, and 550 mg of the title substance was obtained, TLC Rf 0.58, system C. A minor component, Rf 0.55 was also present.

L. Indole-2-carbonylHisnor-C-Sta methyl ester

The product of Example 3K (455 mg) was stirred in 10 mL 5:1 acetic acid-water for 16 h at 25° C., concentrated, co-evaporated with ether several times and dried to give 431 mg of a light yellow powder, HPLC in 40/60 acetonitrile-pH 2.1 0.1M phosphate showing 5.53 min. (39%) and 6.43 (58%).

NMR, DMSO, partial delta, ppm: 2.94 (m), 3.53 (s, 3H, OCH$_3$), 4.02, 4.18, 4.64 (m), 6.80 (s, 1H), 6.9–7.6 (aromatic m), 7.0 (t) 7.4 (d) 7.6 (d).

EXAMPLE 4

BocPheHis(imBoc)nor-C-Sta methyl ester (I, Z=t-butoxycarbonylamino;
R$_2$=N-t-butoxycarbonylimidazol-4-ylmethyl;
W=CH⦀OH; Q=H; M=phenyl; Z$^1$=CO$_2$CH$_3$; and X=cyclohexyl)

According to the procedure for preparation and purification of the product of Example 1C, 2.0 g of the product of Example 3H gave 1.8 g of the title substance as a colorless foam, TLC Rf 0.37 in system C, HPLC in 70/30 MeCN-pH 2.1 0.1M phosphate eluting at 5.42 min. Also obtained was 125 mg of a less polar substance, Rf 0.43, spectrally identified as the O-BocPheHis(im-Boc) derivative of the above-identified product. A mixture (500 mg) the product of this Example and this compound was also obtained.

NMR, CDCl$_3$, 300 MHz, delta, partial: 1.33 and 1.55 (s, 9H ea, Boc), 2.72 and 2.94 (m, 1H ea), 3.1 (m, 2H), 3.70 (s, 3H OCH$_3$), 4.04, 4.52 and 4.95 (m, 1H ea), 4.28 (m, 2H), 6.68 and 8.08 (d, 1H ea), 7.05–7.30 (m, aromatic), 7.88 (s, 1H).

EXAMPLE 5

BocPheHisnor-C-Sta methyl ester (I,
Z=t-butoxycarbonylamino; M=phenyl; Q=H;
R$_2$=imidazol-4-ylmethyl; Z$^1$=CO$_2$CH$_3$;
W=CH⦀OH; and X=cyclohexyl)

The product of Example 4 (800 mg) was stirred 14 h in 10 mL 4:1 acetic acid-water at 25° C., concentrated, co-evaporated several times with ether, giving 580 mg of a light yellow foam, TLC Rf 0.30 in system D, HPLC in 50/50 acetonitrile-pH 2.1 0.1M phosphate, 6.32 min.

NMR, 300 MHz, CDCl$_3$, partial, delta, ppm: 1.42 (s, 9H, Boc), 2.9–3.1 (m,), 3.78 (s, 3H, OCH$_3$), 4.20 and 4.62 (1H each), 4.38 (m, 2H), 6.89 (s, 1H), 7.1–7.4 (m, aromatic), 7.78 (m, 2–3H).

EXAMPLE 6

BocPheHisnor-C-Statone methyl ester
(Z=(CH$_3$)$_3$COCONH; M=phenyl; Q=H;
X=cyclohexyl; R$_2$=imidazol-4-yl methyl; W=C=O;
and Z$^1$=CO$_2$CH$_3$)

A stirred solution of 157 mg pyridinium dichromate in 10 mL dichloromethane was treated at 25° C. with 107 uL acetic anhydride followed by 250 mg of the product of Example 5 in one portion. After 1.5 h the mixture was diluted with 150 mL dichloromethane and this solution was washed with 2×10 mL 1N hydrochloric acid, aqueous bicarbonate, brine, dried (sodium sulfate) and concentrated to give 260 mg of a brown solid, TLC Rf 0.2 (major) and 0.27 (minor, about 5%), in system D. By these TLC's none of the more polar product of Example 5 could be detected. The less polar impurity could be removed by chromatography on silica in 5% ethanol-ethyl acetate but the recovery was poor: 50 mg of crude material gave 7 mg of product which was pure by TLC.

NMR, 300 MHz, CDCl$_3$, partial, delta, ppm: 1.24 (s, Boc), 3.82 (s, OOCH$_3$), 7.0–7.5 (m, aromatic).

EXAMPLE 7

MorpholinocarbonylPheHisnor-C-Sta methylester (I,
Z=morpholinocarbonylamino; M=phenyl; Q=H;
R$_2$=imidazol-4-ylmethyl; W=CH⦀OH;
Z$^1$=CO$_2$CH$_3$; and X=cyclohexyl)

A. (S)-2-Isocyanato-3-phenylpropionic acid benzyl ester

According to the procedure of Lombardino, et. al. (J. Med. Chem. 1964, 7, 97) 18.0 g L-phenylalanine benzyl ester hydrochloride in 150 mL toluene was stirred at reflux under an atmosphere of phosgene for 1.5H, cooled and concentrated to give a solid which was recrystallized from 120 mL hexane to give 16.1 g of colorless needles.

Anal. Calcd for $C_{17}H_{15}NO_3$: C, 72.59; H, 5.37; N, 4.98. Found: C, 72.32; H, 5.35; N, 4.92. MP 68°–72° C. [alpha]$_D^{23}$ −80.4° (c=1.02, CHCl$_3$). IR (CHCl$_3$) 2250, 1750 cm$^{-1}$.

B. MorpholinocarbonylPhe benzyl ester

The product of Example 7A was dissolved in 5 mL dichloromethane, treated at 25° C. with 930 uL morpholine and after 30 min. the mixture was concentrated to a waxy solid which was recrystallized from hot 4:1 hexane-ethyl acetate, giving 1.92 g of the title substance, mp 87°–89° C. MS (chemical ionization, isobutane) 369 (MH+, base peak).

C. MorpholinocarbonylPhe

The product of Example 7B (1.85 g) was dissolved in 30 mL absolute methanol and 5 mL acetic acid and shaken with 0.5 g 10% Pd/C for 1 h under a 53 psi hydrogen atmosphere. The suspension was filtered, concentrated, co-evaporated three times with added toluene and dried to give 1.43 g of a colorless foam.

D. BocHis(imBoc)nor-C-Sta methyl ester

According to the procedure for preparation and purification of the product of Example IC, except that DiBocHis was used in place of BocPheHis(imBoc), 200 mg of the product of the Example 3H gave 345 mg of an approximately 1.5:1 mixture of the title substance, RF 0.38 and the corresponding O-BocHis(imBoc) derivative, Rf 0.50, respectively (TLC on silica in ethyl acetate). This mixture was used without separation in Example 3E. This mixture could be separated by preparative HPLC on a Zorbax C-8 25 cm×9.8 mm column, eluting with 85/15 acetonitrile-water at 6.3 mL/min., detection at 254 nm. The title substance eluted at 4.76 min. and the O-acylated derivative at 6.48 min. Pure samples of each were thereby obtained.

E. BocHisnor-C-Sta methyl ester

The mixture obtained in Example 7D (895 mg) was dissolved in 20 mL methanol at 25° C. and treated with 30 mg anhydrous potassium carbonate. After 1 h the mixture was concentrated and dried to give 604 mg of a yellow foam which was used without purification in the following reaction. HPLC in 50/50 acetonitrile-pH 2.1 0.1M phosphate showed 3.15 min. and 1.98 min. peaks in 2.8:1 ratio. The 1.98 min. peak was presumed to be BocHisOMe, confirmed by NMR of the mixture and by subsequent conversion to a known derivative, below.

F. Hisnor-C-Sta methyl ester hydrochloride

The product of Example 7E (595 mg) was dissolved in 3.4N hydrogen chloride-dioxane at 25° C. and stirred for 30 min. The mixture was concentrated and the residue was dried in vacuo giving 555 mg of a yellow solid, HPLC in 5/95 acetonitrile-pH 2.1 0.1M phosphate 1.54 min. NMR indicated the title substance to be present, contaminated by histidine methyl ester dihydrochloride.

G. MorpholinocarbonylPheHisnor-C-Sta methyl ester

Following the procedure of Example 1C, except that the product of Example 7C was used instead of BocPheHis(imBoc) and that 2.2 equiv triethylamine rather than 1.1 equiv was used, 550 mg of the product of Example 7F gave 365 mg of a light yellow amorphous solid, which was dissolved in 3 mL methanol and treated with 4 mg anhydrous potassium carbonate at 25° C. for 2 h and concentrated giving 355 mg of a light yellow foam. This was dissolved in 4 mL dichloromethane and vigorously stirred 5 min. with 20 mL 1N hydrochloric The layers were separated and the aqueous layer was extracted with 2×2 mL dichloromethane. The aqueous layer was treated with sufficient 2N sodium hydroxide solution so that the pH was raised to 10.5 and then extracted with 4×100 mL dichloromethane. The latter dichloromethane extracts were dried (sodium sulfate) and concentrated to give the 225 mg of title substance as an off-white foam, TLC Rf 0.1 in system D, HPLC 2.95 min. in 50/50 acetonitrile- pH 2.1 phosphate (93% of total UV integration), with a minor impurity at 1.94 min. (5% UV integration).

NMR, 300 MHz, CDCl$_3$, partial, delta, ppm: 0.7–1.4 (m, 6–8H), 1.5–1.8 (m, 4–6H), 3.4–2.8 (m, ca. 8H), 3.6 (m, 4H), 3.73 (s, 3H, OCH$_3$), 4.08 and 4.54 (m, 1H), 4.30 (m, 2H), 5.2 (m, 1H), 6.82 and 7.57 (s, 1H ea), 6.97 and 8.12 (d, 1H ea), 7.1–7.35 (m, ca. 6H, aromatic).

EXAMPLE 8

MorpholinocarbonylPheNlenor-C-Sta methyl ester (I, Z=morpholinocarbonylamino; M=phenyl; Q=H; R$_2$=n-butyl; W=CH    OH; Z$^1$=CO$_2$CH$_3$ and X=cyclohexyl)

A. Norleucine benzyl ester

According to the general procedure outlined in *J. Med. Chem.* 1986, Vol. 30, p. 3575, 15.0 g norleucine (Nle) was mixed with 200 mL benzyl alcohol and cooled to 0° C. Thionyl chloride (25 ml) was added dropwise over 15 min. and the mixture was slowly heated to 90° C. with a fierce evolution of SO$_2$ occurring at about 50° C. After 2 h at 90° C. the mixture was cooled to 0° C. and 25 mL more thionyl chloride was added. The mixture was then heated again at 90° C. for 2 h, cooled, diluted with 1.6 L ether and stored overnight at 0° C. The crystals which formed were filtered, washed with ether and dried to give 23.1 g of a damp solid which was recrystallized from 1:10 ethanol-ether, using 23 mL ethanol. The filtered and dried solid weighed 17.1 g, TLC Rf 0.25 in System C (the spotted plate was exposed to ammonia vapor and dried prior to elution).

B. MorpholinocarbonylPheNle benzyl ester

Following the procedure for preparation and purification of the product of Example 1C, 2.12 g of the product of Example 8A and 2.63 g of the product of Example 7C gave 3.30 g of the title substance as a colorless foam, TLC Rf 0.5 in ethyl acetate on silica, HPLC ret. time 3.27 min. 97% of total absorption to 25 min. in 70/30 MeCN-pH 2.1 0.1M phosphate.

C. MorpholinocarbonylPheNle

The product of Example 8B (3.3 g) was shaken in 35 mL methanol and 7 mL acetic acid with 1.0 g 10% Pd/C for 45 min., filtered through Celite, concentrated, co-evaporated several times with toluene and ether and dried to give 2.9 g of a colorless solid, TLC Rf 0.2 in System C.

D. MorpholinocarbonylPheNlenor-C-Sta methyl ester

Following the procedure for preparation and purification of the product of Example 1C, 300 mg of the product of Example 3H and 700 mg of the product of Example 8C gave 350 mg of the desired product as a light yellow solid, TLC Rf 0.33 in ethyl acetate on silica, HPLC ret. time 6.02 min. in 75/25 MeCN-pH 2.1 0.1M phosphate.

NMR (CDCl$_3$), 300 MHz, partial, delta: 0.86 (t, 3H, J=6-7 Hz, overlapping a 1-2H m centered at 0.9), 1.04-1.36 (m, ca. 8H), 1.46 (dd, 2H), 1.46-1.90 (m, ca 10H), 3.0 (center of dd, 1H), 3.05-3.38 (m, ca. 5H), 3.58 (m, ca. 4H), 3.74 (s, 3H, OCH$_3$), 4.12 (d, 1H, J=1-2 Hz), 4.20 (q, 1H), 4.32-4.50 (m, 2H), 4.92 (d, 1H, J=ca. 8 Hz), 6.48 (d, 1H, J=9 Hz), 6.54 (d, 1H, J=10 Hz), 7.12-7.35 (m, 5H, aromatic).

EXAMPLE 9

MorpholinocarbonylPheNlenor-Sta i-propyl ester (I, Z=morpholinocarbonylamino; M=phenyl; Q=H; R$_2$=n-butyl; W=CH̅OH; Z$^1$=CO$_2$CH(CH$_3$)$_2$; and X=isopropyl

A.
N-t-Butoxycarbonyl-(S)-3-Amino-R,S)-2-hydroxy-5-methylcapronitrile

Boc-Leucinal (119 g) (prepared by Dibal -H reduction of the methyl ester according to the procedure of Rich et al., J. Med. Chem. 1978, 43, 3624), was dissolved in 500 mL dimethoxyethane and treated at 5° C. with 63.8 g of sodium bisulfite in 500 mL water so that the temperature did not exceed 10° C. Stirring was continued 5 h at 0° C. and the mixture was stirred to 25° C. for 48 h. The mixture was concentrated to 350 mL, 1 L ethyl acetate was added, followed by 39.5 g of KCN in 100 mL water. After 72 h of stirring at 25° C., the layers were separated, the aqueous extracted 2× with ethyl acetate, the combined organic layers were washed with brine, dried over sodium sulfate and concentrated giving the title substances as a light yellow oil, 134 g, TLC Rf 0.22 in 1:3 System A.

B.
N-t-Butoxycarbonyl-(S)-3-amino-(R)-2-t-butyldimethylsiloxy-5-methylcapronitrile The product of Example 9A (117 g) was dissolved in 800 mL dimethylformamide and cooled in an ice bath. Imidazole (82.2 g) and 102 g of t-butyldimethylchlorosilane were added sequentially and the mixture was stirred 3 h at 25° C. The mixture was concentrated, 500 mL hexane and 500 mL ether were added and the organic layer was washed with saturated lithium bromide solution (3×50 mL), 1N hydrochloric acid, brine, dried and concentrated giving 166 g of a yellow viscous oil. These two isomers could be separated by column chromatography, loading 17 g of the mixture on 1.8 kg silica, packed and eluted in 1:25 ether-hexane (10 L), then 10 L 1:22.5, followed by 10 L 1:20 ether-hexane. By repeating this procedure 47.2 g of the less polar isomer was obtained as a colorless waxy solid, together with 30.6 g of the more polar isomer, N-t-Butoxycarbonyl-(S)-3-amino-(S)-2-t-butyldimethylsilyloxy-5-methylcapronitrile and 42 g of the mixture.

C.
N-t-Butoxycarbonyl-(S)-3-amino-(R)-2-t-butyldimethylsilyloxy-5-methylhexanamide The product of Example 9B (30 g) was dissolved in 650 mL abs. ethanol and treated at 0° C. with 144 mL 1N sodium hydroxide solution followed by 290 mL 30% aqueous hydrogen peroxide so that the temperature did not exceed 5° C. After 3.5 h at 0° C. the mixture was warmed to 30° C. for 0.5 h, cooled to 0° C. and treated with 116 mL 30% H$_2$O$_2$. After 10 minutes TLC indicated disappearance of the starting material and 200 mL 20% aq. sodium sulfate was added dropwise at less than 5° C. The mixture was reduced by 450 mL volume in vacuo and extracted with ethyl acetate (4×250 mL) which was washed with brine, dried and concentrated giving 36 g of an oil which was chromatographed on 800 g silica with 1:1 ether-hexane. Some impure fractions were rechromatographed in the same system and a total of 17.0 g of colorless product was thereby obtained, Rf 0.2 in 1:1 ether-hexane.

D. (S)-3-Amino-(R)-2-hydroxy-5-methylhexanamide hydrochloride

The product of Example 9C (16.9 g) was dissolved in 50 mL dioxane and treated with 100 mL 3.4N hydrogen chloride-dioxane at 25° C. After 2.5 h the mixture was concentrated, co-evaporated with ether and dried to give 8.7 g of the title substance as a colorless solid, HPLC ret. time 2.35 min. in 5/95 MeCN-pH 2.1 0.1M phosphate.

E. (S)-3-Amino-(R)-2-hydroxy-5-methylhexanoic acid hydrochloride

The product of Example 9D (8.7 g) was dissolved in 150 mL 6N hydrochloric acid and heated at 60° C. for 2 h, concentrated and dried to give 10.6 g of a light yellow solid, HPLC ret. time 5.0 min. in 5/95 MeCN-pH 2.1 0.1M phosphate.

F. i-Propyl (S)-3-amino-(R)-2-hydroxy-5-methylhexanoate hydrochloride

The product of Example 9E (1.25 g) was dissolved in 2-propanol which was saturated with hydrogen chloride and allowed to stand 18 h at 25° C. The mixture was concentrated, the residue co-evaporated with toluene and ether and dried to give 1.36 g of the desired product as an oily yellow foam, TLC Rf 0.33 in System D (spotted plate exposed to NH3 vapor prior to development).

G. MorpholinocarbonylPheNlenor-Sta i-propyl ester

Employing the procedure for preparation and purification of the product of Example 1C, 300 mg of the product of Example 9F and 782 mg of the product of Example 8C gave 209 mg of product as a colorless foam, TLC Rf 0.4 in ethyl acetate, HPLC ret. time 5.86 min. in 75/25 MeCN-pH 2.1 0.1M phosphate.

1H NMR (CDCl$_3$), 300 MHz, partial: delta, 0.82 (t, H, J=6 Hz), 0.89 (center of dd, 6H), 1.21 (center of dd, 6H), 1.3-1.6 (m, ca. 5H), 1.6-2.0 (m, 2-3H), 2.88-3.34 (multiplets, ca. 7H), 3.55 (m, 4-5H), 4.05, 4.20, 4.36 and 4.46 (m, 1H ea), 4.98 (m, 2H), 6.47 and 6.56 (m, 1H ea), 7.05-7.31 (m, 5H).

EXAMPLE 10

MorpholinocarbonylPheLysnor-C-Sta methyl ester (I, Z=morpholinocarbonylamino; M=phenyl; Q=H, R$_2$=4-aminobutyl; X=cyclohexyl; W=CH⦀OH; and Z$^1$=CO$_2$CH$_3$) and MorpholinocarbonylPheLys(E-CBZ)nor-C-Sta methyl ester (I, Z=morpholinocarbonylamino; M=phenyl; Q=H; R$_2$=φCH$_2$OCONH(CH$_2$)$_4$—; X=cyclohexyl; W=CH⦀OH; and Z$^1$=CO$_2$CH$_3$)

A. BocLys(e-CBZ)nor-C-Sta methyl ester

Following the general procedure for preparation and purification of the product of Example 1C, 300 mg of the product of Example 3H and 679 mg of Boc Lys(E-CBZ) (Chemalog Co.) gave 430 mg of the product as a colorless foam, TLC Rf 0.57 in ethyl acetate, HPLC 4.83 min. in 70/30 MeCN-pH 2.1 0.1M phosphate.

B. Lys(E-CBZ)nor-C-Sta methyl ester hydrochloride

The product of Example 10A (400 mg) was dissolved in 5 mL 3.4N hydrogen chloride-dioxane at 25° C., stirred 1.5 h, concentrated, co-evaporated several times with ether and dried giving 366 mg of product as a light yellow foam.

C. MorpholinocarbonylPheLys(E-CBZ)nor-C-Sta methyl ester

Following the procedure for preparation and purification of the product of Example 1C, 360 mg of the product of Example 10B and 311 mg of the product of Example 7C gave 180 mg of product as a colorless foam. TLC Rf 0.64 in System D, HPLC 2.86 min. in 70/30 MeCN-pH 2.1 0.1M phosphate.

1H NMR, CDCl$_3$, 300 MHz, partial, delta: 0.72–2.0 (m, ca. 25H), 2.94 (center of dd, 1H), 3.0–3.32 (m, ca. 6H), 3.50 (center of m, ca. 4H), 3.68 (s, 3H, OCH$_3$), 5.02 (m, 2H), CH$_2$O, 6.52 and 6.68 (d, 1H ea), 7.08–7.48 (m, ca. 11H).

D. MorpholinocarbonylPheLysnor-C-Sta methyl ester hydrochloride

The product of Example 10C (50 mg) was dissolved in 10 mL methanol and 2 mL acetic acid and shaken with 20 mg 10% Pd/C for 45 min. at 25° C. under 50 psi hydrogen The mixture was filtered, concentrated and co-evaporated first with 3 mL 3.4N hydrogen chloridedioxane, then with ether (3×) and dried giving 36 mg of product as pale yellow plates, HPLC 4.08 min. in 40/60 MeCN-pH 2.1 0.1M phosphate, TLC Rf 0.12 in System D.

1H NMR, 250 MHz, DMSO-d$_6$, partial, delta: 0.67–1.8 (m, ca. 25H), 2.67–3.07 (m, ca. 4H), 3.07–3.56 (m), 3.56 (s, 3H, OCH$_3$), 4.07 (apparent d, 1H, J=3 Hz), 4.13–4.40 (m, ca. 3H), 6.72 (d, 1H, J=8 Hz), 7.10–7.4 (m, ca. 5H), 7.62 (d, 1H, J=9 Hz), 8.08 (d, 1H, J=8.5 Hz).

EXAMPLE 11

MorpholinocarbonylPheNlenor-C-Sta 5-aminopentylamide hydrochloride (I, Z=morpholinocarbonylamino; M=phenyl; Q=H; R$_2$=n-butyl, W=CH⫽OH; Z$^1$=CONH(CH$_2$)$_5$NH$_2$; and X=cyclohexyl)

A. 3-(S)-Azido-2-(R)-hydroxy-4-cyclohexyl-N-(5-benzyloxycarbonylaminopentyl)amide Employing the general procedure for synthesis and purification of the product of Example 1C, 800 mg of 5-(benzyloxycarbonylamino)-1-aminopentane and 477 mg of the product of Example 3F gave 490 mg of the title substance as a light yellow syrup, TLC Rf 0.5 in ethyl acetate, IR (CHCl$_3$) 2100 cm$^{-1}$.

B. 3-(S)-Amino-2-(R)-hydroxy-4-cyclohexyl-N-(5-benzyloxycarbonylaminopentyl)amide The product of Example 11A (410 mg) was dissolved in 5 mL methanol and treated at 0° C. with 525 mg of anhydrous stannous chloride in 5 mL methanol over 1 min. The mixture was stirred at 25° C. for 18 h, concentrated, treated with 3 mL water, 3 mL 1N sodium hydroxide solution and extracted with 200 mL ether. The aqueous layer was saturated with sodium chloride and extracted with ether. The ether layers were dried, filtered and concentrated giving 200 mg of an oily foam. The aqueous layers were further basified with 5 mL 1N sodium hydroxide solution and treated with 5 g sodium chloride and extracted with 3×100 mL ethyl acetate, 3×100 mL dichloromethane and the combined organic layers were dried, filtered and concentrated giving an additional 210 mg light yellow foam. The combined solids (410 mg) were chromatographed on 25 g silica eluting with 250 mL each of 1%, 2%, 4%, 6%, 8% and 12% ethanol-dichloromethane giving 172 mg of pure product as a colorless foam, HPLC 3.39 min. in 50/50 MeCN-pH 2.1 0.1M phosphate.

C. MorpholinocarbonylPheNlenor-C-Sta (5-CBZaminopentyl)amide

Using the general procedure for preparation and purification of the product of Example 1C, except that triethylamine was omitted, 165 mg of the product of Example 11B and 246 mg of the product of Example 8C gave 212 mg of product as a light yellow foam, TLC Rf 0.14 in ethyl acetate, 0.80 in System D. HPLC (4.8 min.) indicated approximately 30% (UV absorbance) of an unidentified impurity, 5.03 min. in 60/40 MeCN-pH 2.1 0.1M phosphate.

D. MorpholinocarbonylPheNlenor-C-Sta (5-aminopentyl)amide hydrochloride

The product of Example 11C (186 mg) was dissolved in 20 mL methanol and 4 mL acetic acid and shaken with 60 mg 10% Pd/C for 2 h at 25° C., filtered through Celite, concentrated, co-evaporated with toluene and dried giving 167 mg of a light yellow solid which was co-evaporated twice with 3.4N hydrogen chloride-dioxane and ether and dried to give 150 mg of product as a light yellow solid, HPLC 3.72 min. in 40/60 acetonitrile-pH 2.1 0.1M phosphate.

1H NMR (DMSO-d6+10% H$_2$O), 300 MHz, partial, delta: 0.82 (m, ca. 5H), 0.96–1.8 (m, ca. 25H), 2.7, 3.0, 3.2 and 3.44 (centers of 2–3H multiplets), 3.76 (apparent d, 1H), 4.0–4.2 (m, 2H), 4.2–4.35 (m, 1–2H), 4.35–4.9 (br, 3–4H), 6.7 (m, 1H), 7.06–7.4 (m, 5–6H), 7.63 (m, 1H), 7.92 (br, ca. 2H), 8.05 (d, 1H, J=9 Hz).

EXAMPLE 12

1-FormylpiperazinocarbonylPheNlenor-C-Sta methyl ester (I, Z=4-formylpiperazinocarbonylamino; M=phenyl; Q=H; R$_2$=n-butyl; X=cyclohexyl; W=CH⫽OH; and Z$^1$=CO$_2$CH$_3$)

A. 1-FormylpiperazinocarbonylPhe benzyl ester

The product of Example 7A (3.0 g) was dissolved in 17 mL dichloromethane and treated at 25° C. with 1.7 mL N-formylpiperzine which produced an exotherm to 40° C. After 0.5 h at 25° C. the mixture was concentrated and chromatographed on 100 g silica eluting with 2 L ethyl acetate followed by 10% ethanol-ethyl acetate to give 3.1 g of product, Rf 0.1 in ethyl acetate, HPLC 4.56 min. in 50/50 MeCN-pH 2.1 0.1M phosphate.

B. 1-FormylpiperazinocarbonylPhe

The product of Example 12A (3.0 g) was dissolved in 50 mL methanol and 5 mL acetic acid and shaken with 1.0 g 10% Pd/C under 50 psi hydrogen for 1 H at 25° C., filtered through Celite, concentrated, co-evaporated with toluene (3×) and dried giving 2.31 g of the title substance as a colorless foam, Rf 0.17 in System D.

C. 1-FormylpiperazinocarbonylPheNle benzyl ester

Using the general procedure for preparation and purification of the product of Example 1C, 750 mg of the product of Example 3H and 1.02 g of the product of Example 8A gave 1.06 g of the title substance as a colorless solid, TLC Rf 0.65 in System D, HPLC 2.48 min. in 70/30 MeCN-pH 2.1 phosphate.

D. 1-FormylpiperazinocarbonylPheNle

The product of Example 12C (1.04 g) was dissolved in 30 ml methanol with 3 mL acetic acid, shaken with 300 mg 10% Pd/C for 1 h at 25° C. under 50 psi hydrogen, filtered, concentrated, co-evaporated with toluene (3×), ether and dried to give 870 mg of the title substance as an off-white foam, TLC Rf 0.5 in System D.

E. 1-FormylpiperazinocarbonylPheNlenor-C-Sta methyl ester

Employing the general procedure for preparation and purification of the product of Example 1C, 200 mg of the product of Example 3H and 465 mg of the product of Example 12D gave 194 mg of product as a light yellow foam, TLC Rf 0.53 in System D, HPLC 4.50 min. in 50/50 acetonitrile-pH 2.1 phosphate.

NMR (CDCl$_3$), 300 MHz, partial, delta: 0.82 (t, 3H, J=6 Hz, overlapping an 0.9 multiplet), 1.0–1.35 (m, ca. 5H), 1.44 (center of dd, 2H), 1.44–1.9 (m, ca. 9H), 2.98 and 3.10 (each center of dd, 1H ea), 3.10–3.57 (m, ca. 8H), 3.57–3.72 (m, with 3.72 s [OCH$_3$], total ca. 5H), 4.13 (d, 1H J=3 Hz), 4.21 (q, 1H), 4.39 (q, 1H), 4.49 (q, 1H), 5.18, 6.49 and 6.63 (d, 1H ea, J=6 Hz), 7.08–7.36 (m, 5–6H), 8.0 (s, 1H, N-CHO).

EXAMPLE 13

MorpholinocarbonylPheNlenor-C-Sta (O-4-piperidinobutyryl) methyl ester (I, Z=morpholinocarbonylamino; M=phenyl; Q=H; R$_2$=n-butyl; X=cyclohexyl; W=CH⫶⫶⫶⫶ OCO(CH$_2$)$_3$ piperidino; Z$^1$=CO$_2$CH$_3$)

A. 4-Piperidinobutyryl chloride hydrochloride

4-Piperidinobutyric acid hydrochloride (750 mg) and 4 ml of thionyl chloride were combined and stirred at reflux for 45 min., concentrated, triturated with ether and dried to give 700 mg of light brown solid which when dissolved in dry methanol gave Rf 0.1 in system D, distinctly different from the starting acid and presumably the methyl ester. The solid was used without further purification.

B. MorpholinocarbonylPheNlenor-C-Sta(O-4-piperidinobutyryl methyl ester

The product of Example 8D (50 mg) was dried by addition and removal in vacuo of benzene, dissolved in 1 mL dichloromethane and treated sequentially at 25° C. with 30 uL triethylamine and 25 mg of the product of Example 13A. After 1.5 h 15 uL more triethylamine and 22 mg more acid chloride were added and after another 2.4 h 19 uL triethylamine and 21 mg acid chloride were added. After 1 h more, 7 uL triethylamine and 10 mg acid chloride were added, and 0.5 hr later the mixture was diluted with dichloromethane, washed with aqueous bicarbonate, dried and concentrated giving 75 mg of a dark brown oil which was chromatographed immediately on 3 g silica with 3% ethanol-methylene chloride, eluting then with 100 mL of this solvent and 100 mL each of 5%, 7%, 9% and 13% ethanol-dichloromethane. The title substance eluted cleanly and was obtained as a light brown solid, 25 mg, TLC Rf 0.23 in System D, HPLC 5.09 min. in 60/40 acetonitrile-pH 2.1 phosphate.

1H NMR (CDCl$_3$), 300 MHz, partial, delta: 0.82 (t, 3H, overlapping 1–2H m), 1.04–2.0 (m), 2.26–2.58 (m), 3.06 (m, 2H), 3.1–3.34 (m, 4–6H), 3.57 (m, ca. 4H), 3.70 (s, 3H, OCH$_3$), 4.18 (q, 1H), 4.46 (q, 1H), 4.53 (m, 1–2H), 4.94 (m, 1H), 7.1–7.3 (m, 5–7H).

EXAMPLE 14

MorpholinocarbonylPheNlenor-C-Sta N-methyl amide (I, Z=morpholinocarbonylamino; M=phenyl; Q=H; R$_2$=n-butyl; X=cyclohexyl; W=CH⫶⫶⫶⫶OH; Z$^1$=CONHCH$_3$)

A. 3(S)-Azido-2(R)-t-butyldimethylsilyloxy-4-cyclohexylbutyric acid methyl ester The product of Example 3G (0.60 g) was dissolved in 5 mL of dimethylformamide and treated at 0° C. sequentially with 422 mg imidazole and 523 mg t-butyldimethylchlorosilane. After 18 h at 25° C. the mixture was treated with 211 mg imidazole and 255 mg t-butyldimethylchlorosilane and stirred at 25° C. for 1 h. The mixture was concentrated, the residue dissolved in ethyl acetate, extracted with aqueous 1M lithium chloride solution, 1N hydrochloric acid, brine, dried, filtered, concentrated (giving 900 mg of clear oil) and chromatographed on 25 g silica with 1 L 1:75 etherhexane to give 800 mg of pure product, TLC Rf 0.55 in 1:2 ether-hexane.

B. 3(S)-Azido-2(R)-t-butyldimethylsilyloxy-4-cyclohexylbutyric acid N-methyl amide The product of Example 14A (725 mg) was dissolved in methanol and cooled to 0° C. This solution was saturated with anhydrous methylamine and the stoppered flask stirred at 40° C. for 5 h. The solution was concentrated, the residue co-evaporated with ether and dried giving 642 mg of a colorless solid, TLC Rf 0.18 in 1:2 ether-hexane.

C. 3(S)-Amino-2(R)-t-butyldimethylsilyloxy-4-cyclohexylbutyric acid N-methyl amide The product of Example 14B (640 mg) was dissolved in 30 mL methanol and 3 mL acetic acid and shaken with 200 mg 10% Pd/C under 50 psi hydrogen for 1 h at 25° C. The mixture was filtered through Celite, the filtrate concentrated and the residue dissolved in ethyl acetate. This solution was washed with aqueous sodium bicarbonate, dried, filtered and concentrated to give 550 mg of a colorless oil which was used in the next step without purification.

D. MorpholinocarbonylPheNlenor-C-Sta(O-t-butyldimethylsilyl ether) N-methyl amide Using the general procedure for preparation and purification of the product of Example 1C, except that triethylamine was omitted, the crude product of Example 14C (250 mg) and 358 mg of the product of Example 8C gave 206 mg of the title substance as a light yellow solid, TLC Rf 0.18 in ethyl acetate, Rf 0.7 in System D, HPLC 8.2 min. in 70/30 MeCN-pH 2.1 phosphate.

E. MorpholinocarbonylPheNlenor-C-Sta methyl ester

The product of Example 14D (200 mg) was treated with 3 mL 3N hydrogen chloride-dioxane at 25° C. for 30 min., concentrated, co-evaporated with ether (3×) and dried to give 155 mg of a pale yellow solid, TLC Rf 0.48 in system D, HPLC 4.57 min. in 50/50 acetonitrile-pH 2.1M phosphate.

1H NMR, 300 MHz, DMSO-d6, partial, delta: 0.82 (t, 3H, J=6 Hz, overlapping m 1–2H), 1.0–1.32 (m, ca. 10H), 1.4–1.9 (m), 2.54 (d, 3H, J=6 Hz, NCH$_3$), 2.78 and 2.96 (centers of dd, 1H ea), 3.06–3.28 (m, ca. 4H), 3.42 (center of m, ca. 4H), 3.76 (apparent d, 1H, J=ca. 1 Hz), 4.11 (m, 2H), 4.28 (m, 1H), 6.62, 7.58 and 7.96 (d, 1H ea), 7.06–7.3 (m, 5H).

EXAMPLE 15

MorpholinocarbonylPheNlenor-C-Sta N-n-butyl amide (I, Z=morpholinocarbonylamino; M=phenyl; Q=H; R$_2$=n-butyl; X=cyclohexyl; W=CH∣∣∣∣∣∣∣OH; Z$^1$=CONH(CH$_2$)$_3$CH$_3$)

A.
3(S)-Azido-2(R)-t-butyldimethylsilyloxy-4-cyclohexyl-butyric acid N-n-butyl amide The product of Example 14A (800 mg) was dissolved in 2 mL methanol and 1 mL butylamine and stirred at reflux 18 h. Butylamine (1 ml) was added and refluxing continued 2 h. The mixture was concentrated and chromatographed on 25 g silica eluting with 1:5 ether-hexane, giving 500 mg of a colorless waxy solid, TLC Rf 0.1 in 1:5 ether-hexane, together with 240 mg of recovered starting material.

B.
3(S)-Amino-2(R)-t-butyldimethylsilyloxy-4-cyclohexylbutyric acid N-n-butyl amide The product of Example 15A (450 mg) was dissolved in 30 mL methanol with 3 mL acetic acid and shaken with 220 mg Pd/C for 5 h. The mixture was filtered through Celite, the filtrate concentrated, the residue co-evaporated with added toluene, dissolved in ethyl acetate, washed with three portions of aqueous bicarbonate, dried over magnesium sulfate and concentrated to give 360 mg of a colorless oil which was used without purification in the next step.

C.
MorpholinocarbonylPheNlenor-C-Sta(O-t-butyldimethylsilyl ether)N-n-butyl amide Employing the general procedure for preparation and purification of the product of Example 1C, except that triethylamine was omitted, 355 mg of the product of Example 15B and 300 mg of the product of Example 8C gave 313 mg of product as a colorless solid, Rf 0.8 in System D, HPLC 7.5 min. in 85/15 acetonitrile-water.

D. MorpholinocarbonylPheNlenor-C-Sta N-n-butyl amide

The product of Example 15C (305 mg) was dissolved at 25° C. in 3 mL 3.4N hydrogen chloride-dioxane. After 45 min. the mixture was concentrated, the residue co-evaporated three times with ether and dried giving 239 mg of a beige solid, TLC Rf 0.6 in System D, HPLC 10.2 min. in 50/50 acetonitrile-pH 2.1 phosphate.

1H NMR, DMSO-d6, 300 MHz, partial, delta: 0.9 (triplets, 6H total, overlapping 1–2H m), 1.0–1.85 (m, ca. 20H), 2.76 (center of dd, 1H), 2.9–3.5 (m), 3.74 (apparent d, 1H, J=ca. 1 Hz), 4.14 (m, 2H), 4.27 (m, 1H), 6.60 (d, 1H), 7.05–7.3 (m, 5H), 7.58 (t, 1H), 7.98 (d, 1H).

EXAMPLE 16

MorpholinocarbonylPheNva-nor-C-Sta-i-propyl ester (I, Z=morpholinocarbonylamino; M=phenyl; Q=H; R$_2$=n-propyl; X=cyclohexyl; W=CH∣∣∣∣∣∣∣OH; and Z$^1$=CO$_2$CH(CH$_3$)$_2$)

A. L-Norvaline methyl ester hydrochloride

Anhydrous hydrogen chloride was bubbled into a suspension of 2.0 g L-norvaline (Chemical Dynamics) in 50 mL anhydrous methanol at 0° for 15 min. The resulting solution was stirred at ambient temperature for 18 h. The reaction mixture was concentrated in vacuo to a white solid which was recrystallized from ethanol/ether to afford 2.3 g of the desired methyl ester.

B.
N-(Morpholinocarbonyl)-L-phenylalanine-L-norvaline methyl ester

To a solution of 0.50 g N-(Morpholinocarbonyl)-L-phenylalanine and 0.26 g L-norvaline methyl ester in 10 mL anhydrous methylene chloride was added 0.22 mL triethylamine, 0.33 g 1-hydroxybenzotriazole and 0.38 g 1-(3-dimethylaminopropyl)-3-ethyl carbodiimide. The reaction was stirred at ambient temperature for 16 h, after which it was diluted with 50 mL ethyl acetate and washed (2×25 mL) 0.1N hydrochloric acid solution and (2×25 mL) 0.1N sodium hydroxide solution. The organic phase was dried over magnesium sulfate, filtered and concentrated in vacuo to afford 0.62 g crude dipeptide.

C.
N-(Morpholinocarbonyl)-L-phenylalanine-L-norvaline

To a solution of 0.62 g N-(Morpholinocarbonyl)-L-phenylalanine-L-norvaline methyl ester in 40 mL methanol and 20 mL water was added 1.2 g potassium carbonate. The resulting mixture was stirred at ambient temperature for 60 h, afterwhich it was concentrated in vacuo to an aqueous solution and washed (3×50 mL) ether. The aqueous phase was acidified with 10 mL 4N hydrochloric acid solution and was extracted (3×25 mL) with methylene chloride. The combined extracts were dried over magnesium sulfate, filtered and concentrated to afford 0.46 g crude acid.

D. MorpholinocarbonylPheNva-nor-C-Sta-i-propyl ester

To a solution of 0.13 g N-(morpholinocarbonyl)-L-phenylalanine-L-norvaline and 0.10 g 2(R)-hydroxy-3(S)-amino-4-cyclohexylbutanoic acid 2-propyl ester (Example 17A) in 5 mL anhydrous methylene chloride was added 0.055 mL triethylamine, 0.060 g 1-hydroxybenzotriazole and 0.075 g 1-(3-dimethylaminopropyl)-3-ethyl carbodiimide.

The solution was stirred at ambient temperature for 16 h, afterwhich it was diluted with 40 mL ethyl acetate and washed with 2×25 mL 0.1N hydrochloric acid solution and 2×25 mL 0.1N sodium hydroxide solution. The organic phase was dried over magnesium sulfate, filtered and concentrated in vacuo. The residue was chromatographed on silica gel (29:1, CH$_2$Cl$_2$:EtOH) to afford 0.17 g pure peptide, (77%). NMR (300 MHz, CDCl$_3$): 0.86 (m, 3H), 1.27 (d, J=8 Hz, 6H), 4.09 (m, 1H), 4.25 (m, 1H), 4.46 (m, 1H), 4.51 (m, 1H), 7.25 (m, 5H).

EXAMPLE 17

MorpholinocarbonylPhe-S-methyl-Cysnor-C-Sta i-propyl ester (I, Z=morpholinocarbonylamino; M=phenyl; Q=H; $R_2$=$CH_3SCH_2$—; X=cyclohexyl; W=CH⫶OH; and $Z^1$=$CO_2CH(CH_3)_2$)

A. 2(R)-Hydroxy-3(S)-amino-4-cyclohexylbutanoic acid, 2-propanol ester, hydrochloride Into an ice-cooled solution of 1.0 g N-t-butyloxycarbonyl-2(R)-hydroxy-3(S)-amino-4-cyclohexylbutanoic acid in 50 mL 2-propanol was bubbled anhydrous hydrogen chloride for 20 min. The solution was allowed to warm to ambient temperature and was stirred for 16 h. The solution was concentrated in vacuo and dried under high vacuum to afford 0.93 g of the desired amine hydrochloride ester.

B. S-Methyl-L-cysteine methyl ester, hydrochloride

An ice-cooled suspension of 2.5 g S-methyl-L-cysteine (Chemical Dynamics) in 25 mL anhydrous methanol was saturated with anhydrous hydrogen chloride, during which all material dissolved. The solution was allowed to warm to ambient temperature and was stirred for 20 h. The solution was concentrated in vacuo to a yellow solid, which was recrystallized from ether/ethanol to afford 3.0 g (87%) of the desired methyl ester-amine hydrochloride.

C. N-(Morpholinocarbonyl)-L-phenylalanine-S-methyl-L-cysteine methyl ester

To a solution of 0.96 g N-(morpholinocarbonyl)-L-phenylalanine 3 and 0.55 g S-methyl-L-cysteine methyl ester in 50 mL anhydrous methylene chloride at ambient temperature was added 0.50 mL triethylamine, 0.51 g 1-hydroxybenzotriazole and 0.70 g 1-(3-dimethylaminopropyl)-3-ethyl carbodiimide hydrochloride. After being stirred for 4 h, the solution was diluted with 100 mL ethyl acetate and was washed with 2×35 mL 0.1N hydrochloric acid solution and 2×35 mL 0.1N sodium hydroxide solution. The organic phase was dried over magnesium sulfate, filtered and concentrated in vacuo to afford 1.15 g of the desired solid dipeptide.

D. N-(Morpholinocarbonyl)-L-phenylalanine-S-methyl-L-cysteine

To an ice-cooled solution of 1.15 g N-(morpholinocarbonyl)-L-phenylalanine-S-methyl-L-cysteine methyl ester in 30 mL water and 60 mL methanol was added 3.5 g potassium carbonate. The resulting mixture was stirred at 0° for 15 min. and at ambient temperature for 4 h. The solution was concentrated in vacuo to an aqueous solution, which was acidified with conc. hydrochloric acid and extracted 3×50 mL methylene chloride. The combined extracts were dried over magnesium sulfate, filtered and concentrated in vacuo to afford 1.0 g (89%) of the crude acid.

E. MorpholinocarbonylPhe-S-methyl-Cysnor-C-Sta i-propyl ester

To a solution of 0.43 g N-(morpholinocarbonyl)-L-phenylalanine-S-methyl-L-cysteine 5 and 0.34 g 2(R)-hydroxy-3(S)-amino-4-cyclohexylbutanoic acid 2-propanol ester in 20 mL anhydrous methylene chloride was added 0.17 ml triethylamine, 0.18 g hydroxybenzotriazole and 0.23 1-(3-dimethylaminopropyl)-3-ethyl carbodiimide. The solution was stirred at ambient temperature for 16 h, after which it was diluted with 50 mL ethyl acetate and washed with 25 mL 0.1N hydrochloric acid solution and 25 mL 0.1N sodium hydroxide solution. The organic phase was dried over magnesium sulfate, filtered and concentrated in vacuo. The residue was chromatographed on silica gel (29:1, $CH_2Cl_2$:EtOH) to afford 0.42 g pure peptide 6 (62%). NMR (300 MHz, $CDCl_3$) 1.30 (2xd, 6H), 2.13 (s, 3H), 4.49 (m, 3H), 5.07 (m, 1H), 7.25 (m, 5H).

EXAMPLE 18

Benzimidazole-2-carbonylNlenor-C-Sta methyl ester (II, L=N; $R_5$=n-butyl; and $R_6$=$OCH_3$)

A. benzimidazole-2-carbonyl Norleucine benzyl ester

According to the procedure for preparation of the product of Example 1C, 80 mg of benzimidazole-2-carboxylic acid and 110 mg of norleucine benzyl ester hydrochloride (product of Example 8a) gave after chromatography on silica gel eluting with ethyl acetate-hexanes 110 mg of a solid which was recrystallized from 1:7 ether-hexanes giving 85 mg of a colorless solid.

B. benzimidazole-2-carbonyl Norleucine

The product of Example 18A (82 mg) was dissolved in 15 mL methanol and 2 mL acetic acid and shaken with 50 mg 10% Pd/C under 50 p.s.i. hydrogen at 25° C. for 1 hour, filtered through Celite, concentrated, coevaporated with 3 mL added toluene (5×), and dried giving 48 mg of a yellowish solid, TLC Rf 0.35 in System C.

C. 3(S)-amino-2(R)-t-butyldimethylsilyloxy-4-cyclohexylbutyric acid methyl ester Using the procedure for preparation of the product of Example 14B, 750 mg of the product of Example 18B gave 500 mg of the title substance as a yellow oil.

D. benzimidazole-2-carbonylNlenor-C-Sta methyl TBDMS ether

According to the procedure for preparation of the product of Example 1C, 65 mg of the product of Example 18C and 45 mg of the product of Example 18B gave 110 mg of crude product which was purified on silica eluting with ether-hexane giving 65 mg of a colorless foam, TLC Rf 0.52 in 1:1 System A.

E. benzimidazole-2-carbonylNlenor-C-Sta methyl ester

The product of Example 8D (60 mg) was dissolved in 3 mL 4N HCl-dioxane. After 45 minutes at 25° C. the mixture was concentrated, the residue coevaporated with ether, dissolved in ethyl acetate, washed with aqueous sodium hydroxide, dried, concentrated and chromatographed on silica in ethyl acetate-hexane (1:1) giving 27 mg of yellow solid which was purified by preparative HPLC (1 cm C-8 column), eluting with 7/3 acetonitrile-water. Ten (10) mg of the pure substance was thereby obtained, TLC Rf 0.55 on silica in ethyl acetate, HPLC 3.17 minutes in 70/30 acetonitrile-pH 2.1 phosphate.

1H NMR, $CDCl_3$, 300 MHz, partial, delta ppm: 0.83 (t, 3H), 3.80 (s, 3H), 4.10, 4.15, 4.29, 4.57 and 4.79 (m, 1H ea), 7.25 (m, 2H), 7.33 (m, 2–3H), 7.50, 7.77 and 8.10 (d, 1H ea).

EXAMPLE 19

MorpholinocarbonylPheNlenor-C-Sta Sodium Salt (I, Z=morpholinocarbonylamino; M=phenyl; Q=H; R$_2$=n-butyl; X=cyclohexyl; W=CH⋮⋮⋮⋮OH; and Z$^1$=CO$_2$H)

The product of Example 8 (25 mg) was dissolved in 0.5 mL dioxane and treated at 25° C. with 42 uL 1N sodium hydroxide solution. After 3 hours the mixture was concentrated to give the title substance as a light yellow solid (17 mg), HPLC 3.06 minutes in 60/40 acetonitrile-pH 2.1 phosphate buffer.

1H NMR, DMSO, 300 MHz, partial, delta ppm: 0.87 (t, 3H), 4.97, 5.07 and 5.34 (m, 1H ea), 6.66, 7.98 and 8.10 (d, 1H ea), 7.1–7.35 (m, aromatic).

EXAMPLE 20

3-(S)-MorpholinocarbonylPheNorleucylamino)-2-(R)-hydroxy-4-phenylbutyramide (I, Z=morpholinocarbonylamino; M=phenyl; Q=H; R$_2$=n-butyl; X=phenyl W=CH⋮⋮⋮⋮⋮⋮OH; and Z$^1$=CONH$_2$)

According to the procedure for preparation and purification of the product of Example 1C, 148 mg of 3(S)-amino-2(R)-hydroxy-4-phenylbutyramide hydrochloride (Example 1D of U.S. Pat. No. 4,668,769) and 251 mg of the product of Example 8C gave 170 mg of a colorless powder, TLC Rf 0.3 in System C.

1H NMR, DMSO, 250 MHz, partial, delta ppm: 0.82 (t, 3H), 2.60 (dd, 1H), 2.80 (overlapping dd, 1H), 2.95 (dd, 1H), 3.42 (m, 4H), 3.68 (d, 1H), 4.17 (m, 2H), 4.28 (m, 1H), 6.61, 7.52 and 7.91 (d, 1H ea), 7.05–7.35 (m, aromatic).

EXAMPLE 21

MorpholinocarbonylPheNlenor-C-Sta amide (I, Z=morpholinocarbonylamino; M=phenyl; Q=H; R2=n-butyl; X=cyclohexyl; W=C⋮⋮⋮⋮⋮=OH; and Z$^1$=CONH$_2$)

A. Boc nor-C-Sta amide TBDMS ether

The product of Example 1C, U.S. Pat. No. 4,668,769, (9.17 g) was dissolved in 200 mL methanol and shaken with 1 g 10% RhC for 70 hours at 25° C. and 30 p.s.i. hydrogen, filtered through Celite and concentrated giving 8.25 of a pale yellow foam which was chromatographed on 400 g silica in ethyl acetate-hexane (3 L of 1:3, then 2 L 100:0), giving 7.2 g of the product as a colorless crystalline solid.

B. nor-C-Sta amide hydrochloride

The product of Example 21A (6.1 g) was dissolved in 15 mL 4N HCl-dioxane, stirred 3 hours at 25° C., concentrated and coevaporated with added ether giving 3.00 g of a colorless powder which was suspended in a minimal amount of ether, filtered, and dried to yield 2.70 g of colorless solid, m.p. 236°–238° C.

C. morpholinocarbonylPheNlenor-C-Sta-amide

According to the procedure for preparation and purification of the product of 1C, 150 mg of the product of Example 21B and 248 mg of the product of Example 8C gave 169 mg of the title substance as a colorless powder, TLC Rf 0.30 in System C.

1H NMR, DMSO, 250 MHz, partial, delta ppm: 0.85 (t, 3H), 3.44 (m, 4H), 3.73 (m, 1H), 4.15 (m, 2H), 4.30 (m, 1H), 5.64, 6.64 and 8.02 (d, 1H), 7.10–7.35 (m, aromatic).

EXAMPLE 22

Benzimidazole-2-carbonylHisnor-C-Sta methyl ester (II, L=N; R$_5$=imidazol-4-ylmethyl; R$_6$=OCH$_3$)

A. diBocHisnor-C-Sta methyl ester TBDMS ether

According to the procedure for preparation of the product of Example 1C, 750 mg of the product of Example 18C and 1.05 g of Boc-His(imBoc) gave 1.6 g of crude product which was chromatographed on silica eluting with ethyl acetate-hexane to give 932 mg of the title substance, TLC Rf 0.31 in 1:1 System A.

B. Hisnor-C-Sta methyl ester dihydrochloride

The product of Example 22A (400 mg) was dissolved in 2 mL dichloromethane, cooled to 0° C. and treated with 3 mL trifluoroacetic acid. After 30 minutes at 0° C. and 80 minutes at 30° C. the mixture was concentrated and coevaporated with three portions of added 4N HCl-dioxane, then with added ether, and dried, giving 210 mg of a pale yellow solid.

C. benzimidazole-2-carbonylHisnor-C-Sta methyl ester

According to the procedure for preparation and purification of the product of Example 1C, 205 mg of the product of Example 22B and 93 mg of benzimidazole-2-carboxylic acid gave 27 mg of a pale yellow solid which was chromatographed again on 1 g silica in 6% ethanol-dichloromethane giving 12 mg of product, TLC Rf 0.44 in System D, HPLC 6.01 minutes in 60/40 acetonitrile-pH 2.1 phosphate.

1H NMR, CDCl$_3$, 300 MHz, partial, delta ppm: 3.75 (s, 3H), 4.20 (br, 1H), 3.16 (m), 6.96 (s, 1H).

EXAMPLE 23

4-MethylpiperazinocarbonylPheNlenor-C-Sta-N-methylamide (I, Z=4-methylpiperazinocarbonylamino; M=phenyl; Q=H; R$_2$=n butyl; X=cyclohexyl; W=CH⋮⋮⋮⋮ OH; and Z$^1$=CONHCH$_3$)

A. 4-methylpiperazinocarbonylPhe benzyl ester

The product of Example 7A (15.0 g) was dissolved in 100 mL dichloromethane and treated at 3° C. with N-methylpiperazine. After 10 minutes (temperature rose to 20° C.) the mixture was concentrated and the residue purified on silica gel (eluting with 5%–11% ethanol in dichloromethane) giving 18.1 g of a pale yellow oil.

B. 4-methylpiperazinocarbonylPhe hydrochloride

The product of Example 23A (18 g) was dissolved in 150 mL acetic acid and shaken with 3 g 10% Pd/C under 50 p.s.i. hydrogen for 45 minutes at 25° C., filtered through Celite, concentrated, the residue coevaporated with added toluene (2×), ether (2×) and dried giving 16.8 g of a colorless hygroscopic foam. This was coevaporated three times with 30 mL 4N HCl-dioxane and dried giving 15.9 g of colorless crystals.

C. 4-methylpiperazinocarbonylPheNle benzyl ester

According to the procedure for preparation and purification of the product of Example 1C except that 2.5 equiv of triethylamine was used, 2.00 g of norleucine benzyl ester (8A) and 2.54 of the product of Example 23B gave 2.34 g of a colorless white foam, TLC Rf 0.12 in System C.

D. 4-methylpiperazinocarbonylPheNle

The product of Example 23C (2.32 g) was dissolved in 20 mL of 10:1 methanol-acetic acid and shaken with 500 mg 10% Pd/C under 50 p.s.i. hydrogen for 1.5 hours at 25° C., filtered through Celite, coevaporated three times each with added toluene and ether, and dried giving 2.15 g of colorless solid.

E. 4-methylpiperazinocarbonylPheNlenor-C-Sta-N-methylamide TBDMS ether

According to the procedure for preparation and purification of the product of Example 1C, 350 mg of the product of Example 23D and 201 mg of the product of Example 14C gave 235 mg of a colorless solid, HPLC 4.92 minutes in 70/30 acetonitrile-pH 2.1 phosphate.

F. 4-methylpiperazinocarbonylPheNlenor-C-Sta-N-methylamide

The product of Example 23E (230 mg) was dissolved in 5 mL 4N HCl-dioxane at 25° C. After 30 minutes the mixture was concentrated at reduced pressure, the residue coevaporated several times with added ether, dried, triturated with ether and dried giving 175 mg of a yellow solid, HPLC 3.92 minutes in 40/60 acetonitrile-pH 2.1 phosphate, TLC Rf 0.08 in System D (the spotted plate being exposed to $NH_3$ vapor prior to elution).

1H NMR, $CDCl_3$, 300 MHz, partial, delta ppm: 0.90 (t, 3H), 2.59 (d, 3H), 3.82 (m, 1H), 7.00, 7.62 and 8.08 (d, 1H ea).

EXAMPLE 24

MorpholinocarbonylPheNlenor-C-Sta ethyl ketone (I, Z=morpholinocarbonylamino; M=phenyl; Q=H; $R_2$=n-butyl; X=cyclohexyl; W=CH|||||| OH; and $Z^1$=COCH$_2$CH$_3$)

A. 5(S)-Bocamino-4(R)-benzyloxy-6-cyclohexyl-3(R,S)-hexanol

The product of Example 5A of U.S. Pat. No. 4,668,769 (700 mg) was dissolved in 5 mL ether and treated at 0° C. with 1.45 mL of 2.8M ethylmagnesium bromide in ether. After 20 minutes another 650 uL 2.8M ethylmagnesium bromide was added and after 30 minutes the solution was treated with 1 mL saturated aqueous ammonium chloride. The mixture wad diluted with ether, extracted with 1N hydrochloric acid, bicarbonate, brine, dried over magnesium sulfate and concentrated giving 530 mg of a vicous oil, TLC Rf 0.4 and 0.25 (1:3 System A).

B. 5(S)-Bocamino-4(R)-benzyloxy-6-cyclohexyl-3-hexanone

The product of Example 24A (525 mg) was dissolved in 5 mL ether and treated at 25° C. with 1.0 mL of chromic acid solution (Org. Syn. V, p. 310). After 1 hour ether was added and the solution was washed with 1N sodium hydroxide solution, brine, dried over sodium sulfate, concentrated and the residue purified on silica eluting with 1:7 ether-hexanes giving 250 mg of a colorless oil, TLC Rf 0.6 in 1:3 System A).

C. 5(S)-amino-4(R)-benzyloxy-6-cyclohexanone hydrochloride

The product of Example 24B (245 mg) was dissolved in 3 mL 4N HCl-dioxane, stirred 45 minutes at 25° C., concentrated, the residue coevaporated with added ether and dried giving 190 mg of a pale yellow foam, TLC Rf 0.58 in System C (the spotted substance exposed to $NH_3$ vapor prior to plate elution).

D. morpholinocarbonylPheNlenor-C-Sta ethyl ketone benzyl ether

According to the procedure for preparation and purification of the product of Example 1C, 95 mg of the product of Example 24D and 142 mg of the product of Example 8C gave 133 mg of the title substance as a colorless foam.

E. morpholinocarbonylPheNlenor-C-Sta ethyl ketone

The product of Example 24D (120 mg) was dissolved in 3 mL of 2:1 methanol-acetic acid and shaken with 75 mg 10% Pd/C under 50 p.s.i. hydrogen for 20 hours at 25° C., the mixture filtered through Celite, the filtrate concentrated, coevaporated 5x with added toluene, 5x with added ether, and dried giving 100 mg of a light beige solid, HPLC 2.96 minutes in 70/30 acetonitrile-pH 2.1 buffer, TLC Rf 0.3 (ethyl acetate, silica).

1H NMR, $CDCl_3$, 300 MHz, partial, delta ppm: 0.88 and 1.09 (t, 3H ea), 2.47 and 2.78 (dq, 1H ea), 3.10 (m, 2H), 3.17 and 3.64 (m, 4H ea), 4.13, 4.16 and 4.98 (m, 1H ea), 4.52 (m, 2H), 5.17 and 5.48 (d, 1H ea), 7.1–7.35 (m, aromatic).

EXAMPLE 25

MorpholinocarbonylPheHisnor-C-Sta-N-methylamide (I, Z=morpholinocarbonylamino; M=phenyl; Q=H; $R_2$=imidazol-4-ylmethyl; X=cyclohexyl; W=CH|||||| OH; and $Z^1$=CONHCH$_3$

A. diBocHis benzyl ester

DiBoc-L-Histidine (0.317 mol) was dissolved in 800 mL dry DMF and 43.9 g anhydrous potassium carbonate was added. The mixture was stirred in an ice bath and 37.8 mL benzyl bromide was added. The mixture was stirred at 0° C. and allowed to warm to 25° C. overnight, filtered through Celite (washing with ether), the filtrate concentrated, the residue dissolved in 700 mL ethyl acetate, and this solution washed with 2×200 mL 1M lithium chloride and 2×4M lightium chloride, 2×100 mL 1N NaOH, water, brine, dried over magnesium sulfate and concentrated to give an oily solid. This solid was stirred vigorously under 500 mL hexane, whereupon a crystalline mass formed which was pulverized in a mortar and washed with 2×100 mL hexane at 25° C. on the filter. The solid on drying weighed 120.5 g, mp 99°–99.5° C., TLC Rf 0.35 in 1:1 System A, $[a]^D$ 25 −6.4 (c=1.09, $CHCl_3$).

B. histidine benzyl ester dihydrochloride

The product of Example 25A (92 mg) was dissolved in 400 mL of cold 4N HCl-dioxane and the resulting suspension was stirred 24 hours at 25° C. Most of the liquid was decanted and the residue concentrated, dried, washed 3x with ether and dried giving the title substance as a colorless solid in quantitative yield. $[a]^D$ 25 rose to +6.4 (c=2.865, MeOH) over 24 hours (reported, Org. Prep. Proc. Int'l., 1970, 255, $[a]^D$=6.54 under these conditions). The procedure illustrated by these examples is superior to that reported.

C. morpholinocarbonylPheHis benzyl ester

According to the procedure for preparation of the product of Example 1C, 1.37 g of the product of Example 7C and 1.21 g of the product of Example 25B gave 1.8 g a yellow foam (crude). This material was triturated with ether and dried giving 1.68 g of a light yellow foam (HPLC 2.92 minutes in 50/50 acetonitrile-pH 2.1 phosphate) which was used without further purification.

D. morpholinocarbonylPheHis(imBoc) benzyl ester

The product of Example 25C (1.68 g) was dissolved in 30 mL dioxane and 15 mL water and the pH was adjusted to 11 with aqueous 1N sodium hydroxide. Di-t-butyldicarbonate (850 uL) was added and the pH was maintained with added sodium hydroxide between 9 and 11. After 45 minutes 450 uL di-t-butyldicarbonate was added (pH maintained around 10.5) and after 1.5 hours total the pH was adjusted to 5 with 1N HCl, and the solution was partially concentrated and then extracted with 4×100 mL ethyl acetate. These extracts were washed with aqueous sodium hydroxide, bicarbonate, dried over sodium sulfate and concentrated giving 1.85 g of oily foam which was purified on silica eluting with a gradient of ethanol in dichloromethane (2 to 8% EtOH), giving 1.05 g of a pale yellow foam, HPLC 3.10 minutes in 70/30 acetonitrile-buffer, TLC Rf 0.13 (ethyl acetate, silica).

E. morpholinocarbonylPheHis

The product of Example 25D (500 mg) was dissolved in 25 mL methanol and 2 mL acetic acid and shaken with 250 mg 10% Pd/C under 50 p.s.i. hydrogen for 45 minutes at 25° C., the mixture filtered through Celite, the filtrate concentrated, coevaporated with added toluene (3×), ether (4×) and dried giving 423 mg of a colorless solid, TLC Rf 0.3 in System C.

F. morpholinocarbonylPheHis(imBoc)nor-C-Sta-N-methylamide TBDMS ether

According to the procedure for preparation and purification of the product of Example 1C, 140 mg of the product of Example 14C and 285 mg of the product of Example 25E, gave 223 mg of colorless foam, HPLC 9.95 minutes in 70/30 acetonitrile-pH 2.1 buffer.

G. morpholinocarbonylPheHisnor-C-Sta-N-methylamide TBDMS ether

The product of Example 25F (218 mg) was dissolved in 3 mL methanol at 25° C. and treated with 10 mg anhydrous potassium carbonate. After 1 hour the mixture was concentrated giving 193 mg of a colorless solid, TLC Rf 0.06 in System C.

H. morpholinocarbonylPheHisnor-C-Sta-N-methylamide hydrochloride

The product of Example 25G (185 mg) was dissolved in 3 mL 4N HCl-dioxane, stirred 1 hour at 25° C., concentrated and coevaporated with added ether giving 150 mg of a colorless solid, HPLC 1.83 minutes in 1:1 acetonitrile-pH 2.1 phosphate, TLC Rf 0.25 in System D (the spotted substance exposed to $NH_3$ vapor prior to plate elution).

1H NMR, DMSO, 250 MHz, partial, delta ppm: 2.58 (d, 3H), 3.90, 4.12, 4.27 and 4.58 (m, 1H ea), 6.87, 7.60, 7.82 and 8.33 (d, 1H ea), 7.13–7.34 (m, aromatic), 7.44 and 9.02 (s, 1H ea).

EXAMPLE 26

MorpholinocarbonylPheNlenor-C-Sta-dimethylamide (I, Z=morpholinocarbonylamino; M=phenyl; Q=H, $R_2$=n-butyl; X=cyclohexyl; W=CH ⫼OH; and $Z^1$=CONH(CH$_3$)$_2$)

A. Bocnor-C-Sta-dimethylamide

According to the procedure for preparation of the product of Example 1C, 350 mg Boc nor-C-Sta (Example 1G, U.S. Pat. No. 4,668,769) and 170 mg dimethylamine hydrochloride gave 405 mg of crude product which was purified on silica (1:2 ethyl acetate-hexanes) giving 310 mg of a colorless foam.

B. nor-C-Sta-dimethylamide hydrochloride

The product of Example 26B (305 mg) was dissolved in 4 mL HCl-dioxane, stirred 18 hours, concentrated, coevaporated with ether and dried giving 250 mg of a light yellow solid, TLC Rf 0.1 in System C.

C. morpholinocarbonylPheNlenor-C-Sta-dimethylamide

According to the procedure for preparation of the product of Example 1C, 245 mg of the product of Example 26B and 472 mg of the product of Example 8C gave 325 mg of a colorless foam, HPLC 5.36 minutes in 50/50 acetonitrile-pH 2.1 phosphate.

2H NMR, CDCl$_3$, 300 MHz, partial, delta ppm: 0.86 (t, 3H), 2.91 and 3.03 (s, 3H ea), 3.07 (m, 2H), 3.45 and 3.59 (m, 4H ea), 4.15 (m, 2H), 4.31, 4.36 and 4.52 (m, 1H ea), 5.00, 6.13 and 6.49 (d, 1H ea), 7.08–7.26 (m, aromatic).

EXAMPLE 27

MorpholinocarbonylPheNlenor-C-Statone methyl ester (I, Z=morpholinocarbonylamino; M=phenyl; Q=H, $R_2$=n-butyl; X=cyclohexyl; W=C=O; $Z^1$=CO$_2$CH$_3$ The product of Example 8D (100 mg) was dissolved in 0.4 mL dichloromethane and treated with 48 uL acetic anhydride and 141 mg pyridinium dichromate. After 45 minutes the mixture was placed in a −20° C. freezer, where it was stored for 18 hours. Ethyl acetate was added and the solution was washed with 1N HCl, aqueous sodium bicarbonate, 1N sodium hydroxide, brine, dried over sodium sulfate and concentrated giving 85 mg of colorless solid which was chromatographed on silica eluting with ethanol-dichloromethane giving 44 mg of the title substance, TLC Rf 0.28 (ethyl acetate on silica).

1H NMR, CDCl$_3$, 300 MHz, partial, delta ppm: 0.87 (t, 3H), 3.62 (m, 4H), 4.34, 4.51 and 5.09 (m, 1H ea), 4.94, 6.57 and 6.77 (d, 1H ea), 7.15–7.35 (m, aromatic).

EXAMPLE 28

Morpholinocarbonyl O-MeTyrNlenor-C-Sta ethyl ketone (I, Z=morpholinocarbonylamino; M=p-methoxyphenyl; Q=H; $R_2$=n-butyl; X=cyclohexyl; W=CH ⫼OH; $Z^1$=COCH$_2$CH$_3$

A. morpholinocarbonyl O-MeTyrNlenor-C-Sta ethyl ketone benzyl ether

According to the procedure for preparation and purification of the product of Example 1C, 150 mg of Morpholinocarbonyl O-MeTyr Nle and 97 mg of the product of Example 24D gave 140 mg of colorless foam, TLC Rf 0.38 (ethyl acetate, silica).

B. morpholinocarbonyl O-MeTyrNlenor-C-Sta ethyl ketone

The product of Example 28A (128 mg) was dissolved in 3 mL methanol and 1 mL acetic acid and shaken with 130 mg 10% Pd/C under 50 p.s.i. hydrogen for 18 hours at 25° C. The mixture was filtered through Celite, concentrated, and the residue coevapoarted with added toluene (5×) and ether (5×) giving after drying 115 mg of a pale yellow solid, TLC Rf 0.25 (ethyl acetate-silica), HPLC 3.64 minutes in 70/30 acetonitrile-pH 2.1 phosphate.

1H NMR, CDCl$_3$, 300 MHz, partial, delta ppm: 0.90 and 1.11 (t, 3H eac), 2.47 and 2.79 (dq, 1H eac), 3.04 (m, 2H), 3.29 and 3.64 (m, 4H eac), 3.80 (s, 3H), 4.13, 4.16, 4.25 and 4.35 (m, 1H eac), 4.95, 6.28 and 6.43 (d, 1H ea), 6.84 and 7.12 d, 2H ea).

EXAMPLE 29

A. MorpholinocarbonylPheNle 2(R,S)-methyl-nor-C-Sta methyl ester (I, Z=morpholinocarbonylamino; M=phenyl; Q=H; $R_2$=n-butyl; X=cyclohexyl; W=C(CH$_3$) ⫼OH and C(CH$_3$) ⬛ OH; $Z^1$=CO$_2$CH$_3$)

A. methyl 3(S)-Boc amino-4-cyclohexyl-2-oxo-1-methylthio-1-ylsulfoxide

Methyl methylthiomethyl sulfoxide (8.2 mL) in 78 mL dry THF was cooled in an ice bath and treated dropwise over 20 minutes with 49 mL 1.6 butyllithium in hexane. After 45 minutes the solution was brought to −25° C. and treated dropwise with a solution of Boc-hexahydro-L-phenylalanine methyl ester in 20 mL THF. After 30 minutes at −25° C. the solution was concentrated at reduced pressure and the residue dissolved in 200 mL ether. This solution was washed with water (4×30 mL), brine and dried over magnesium sulfate. To the aqueous layers more brine was added, and this mixture was extracted with ethyl acetate which was dried over magnesium sulfate. The organic layers were combined and concentrated giving an orange oil which was chromatographed on silica (ethyl acetate-hexanes) giving 6.8 g of a light amber foam, TLC Rf 0.28 in 3:1 System A.

B. Boc-nor-C-Sta methyl ester

The product of Example 29A, 4.25 g was dissolved in 25 mL methanol at 0° C. and treated with 2.86 g iodine. After stirring 1 hour at 30° C., the mixture was poured into a stirred mixture of ice, 300 mL 10% aqueous sodium thiosulfate and 100 mL ethyl acetate. The organic layer was separated and the aqueous layer washed with ethyl acetate (4×50 mL). The organic layers were dried over magnesium sulfate, concentrated and chromatographed on silica (ethyl acetate-hexane), giving 980 mg of a yellow solid, TLC Rf 0.32 (1:2 System C). Also obtained was 1.66 g of an oil, TLC Rf 0.45 in the same system, identified as 3(S)-t-Bocamino-4-cyclohexyl-2-oxo-1,1-dismethylthio-1-methoxybutane.

C. methyl 3-Bocamino-4-cyclohexyl-2(R,S)methyl-2-hydroxybutyrate

A solution of 459 mg of the Rf 0.32 product of Example 29B in 2 mL ether at 0° C. was treated with 1.92 mL methylmagnesium bromide (1.9M in n-butyl ether). After 10 minutes at 0° C. 1 mL saturated aqueous ammonium chloride was added. The mixture was extracted with ether which was washed with 1N HCl, aqueous sodium bicarbonate and brine, dried over magnesium sulfate, filtered, concentrated and the residue chromatographed on silica (ether-hexanes) giving 375 mg of a colorless solid.

D. methyl 3-amino-4-cyclohexyl-2(R,S)-methyl-2-hydroxybutyrate hydrochloride The product of Example 29C was dissolved in 3 mL 4N HCl-dioxane and stirred at 25° C. After 30 minutes the mixture was concentrated and coevaporated with ether giving 275 mg of a yellow foam.

E. morpholinocarbonylPheNle 2(R,S)-methyl nor-C-Sta methyl ester

According to the procedure for preparation and purification of the product of Example 1C, 255 mg of the product of Example 29E and 375 mg of the product of Example 8C gave 321 mg of a colorless solid, TLC Rf 0.68 in System C, HPLC 5.24 minutes (68%) and 5.51 minutes, 32% in 60/40 acetonitrile-water. The two components were separated by semipreparative HPLC (9.8×250 mm Zorbax C-8, 6.3 mL/min, 60/40 acetonitrile-water, 254 nM detection) in ca. 20 mg injections giving 172 mg of the less-retained substance and 97 mg of the more retained substance as colorless solids (HPLC in the analytical system above of 5.20 and 5.53 minutes, respectively, each homogeneous (>98%)).

The less retained substance by HPLC, 1H NMR, CDCl$_3$, 300 MHz, partial, delta ppm: 0.82 (t, 3H), 1.34 (s, 3H), 3.04 and 3.13 (dd, 1H ea), 3.13–3.34 (m), 3.59 (m, 4–5H), 3.78 (s, 3H), 4.32 (m, 2H), 4.51 (m, 1H), 5.05 (m, 1H), 6.36 (m, 1H), 7.71 (m, 1H), 7.14–7.35 (m, aromatic).

The more retained substance by HPLC, 1H NMR, CDCl$_3$, 300 MHz, partial, delta ppm: 0.89 (t, 3H), 1.39 (s, 3H), 3.04 (dd, 1H), 3.60 (m, 4H), 3.76 (s, 3H), 3.92, 4.47 and 4.88 (m, 1H ea), 4.20–4.32 (m, 2H), 7.12–7.35 (m, aromatic).

EXAMPLE 30

MorpholinocarbonylPheN-alpha-MeNlenor-C-Sta ethyl ketone (I, Z=morpholinocarbonylamino; M=phenyl; Q=CH$_3$; $R_2$=n-butyl; X=cyclohexyl; W=CH ⫼ OH; $Z^1$=COCH$_2$CH$_3$)

A. N-Boc-N-methyl-L-norleucine

N-methyl-L-Norleucine (1.0 g) (J. Chem. Soc. 1968, p. 930) was dissolved in 11 mL DMF at 0° C. and treated with 2.1 mL triethylamine followed by 1.74 mL di-t-butyl dicarbonate. The mixture was stirred at 0° C. for 4 hours and then allowed to warm to 20° C. overnight. The mixture was concentrated, dissolved in a mixture of aqueous saturated sodium bicarbonate and ethyl acetate. The aqueous layer was separated, washed with ethyl acetate and acidified with HCl in the presence of ethyl acetate. This organic layer was separated and combined with further ethyl acetate extracts of the aqueous layer, dried over magnesium sulfate and concentrated giving 1.17 g of yellow oil.

B. N-Boc-N-methyl-L-norleucine benzyl ester

The product of Example 30A (750 mg) was dissolved in 7.5 mL dry DMF at 0° C. and treated with 423 mg anhydrous potassium carbonate and 364 uL of benzyl bromide. The mixture was stirred in a flask cooled in an ice bath which was allowed to warm to 20° C. overnight. The mixture was diluted with ether, filtered through Celite. The filtrate was concentrated and the residue was dissolved in ethyl acetate which was washed with 10% aqueous lightium chloride (3×), 1N sodium hydroxide, brine, dried over magnesium sulfate and concentrated giving 942 mg of a yellow oil.

C. N-methyl-L-Norleucine benzyl ester hydrochloride

The product of Example 30B (915 mg) was dissolved in 3.5 mL 4N HCl-dioxane and stirred at 25° C. for 45 minutes. The mixture was concentrated and 727 mg of an off-white powder was thereby obtained, TLC Rf 0.55 in System C.

D. morpholinocarbonylPhe N-MeNle benzyl ester

According to the procedure for preparation and purification of the product of Example 1C, 370 mg of the product of Example 30C and 378 mg of the product of Example 7C gave 476 mg of an opaque oil, TLC Rf 0.69 in System C.

E. morpholinocarbonylPhe N-MeNle

The product of Example 30E (468 mg) was dissolved in 10 mL methanol and 1 mL acetic acid and shaken with 100 mg 10% Pd/C at 25° C. and 50 p.s.i. hydrogen for 1 hour, filtered through Celite, concentrated and coevaporated with added toluene, then ether and dried giving 365 mg of an off-white powder, TLC Rf 0.6 in System C.

F. morpholinocarbonylPheN-MeNle nor-C-Sta ethyl ketone benzyl ether

According to the procedure for preparation of the product of Example 1C, 78 mg of the product of Example 24D and 93 mg of the product of Example 30E gave 148 mg of an off-white foam which was used without further purification.

G. morpholinocarbonylPhe N-MeNlenor-C-Sta ethyl ketone

The product of Example 30F (142 mg) was dissolved in 10 mL methanol and 1 mL acetic acid and shaken with 150 mg 10% Pd/C at 25° C. and 50 p.s.i. hydrogen for 20 hours, filtered, concentrated, coevaporated with toluene, then ether, and dried giving 120 mg of an off-white foam. This material was chromatographed on silica (ethanol-dichloromethane gradient) giving 93 mg of colorless solid, TLC Rf 0.48 in System C, HPLC 5.29 minutes in 70/30 acetonitrile-pH 2.1 phosphate.

1H NMR, DMSO, 250 MHz, partial, delta ppm: 0.80 and 0.85 (t, 3H ea), 2.91 (s, $NCH_3$), 4.5 and 4.63 (m, 1H ea), 4.59 (m, 2H), 4.94, 5.39, 5.58, 6.62 and 8.00 (d, presumably NH resonances of different rotamers), 7.15–7.38 (m, aromatic).

EXAMPLE 31

MorpholinocarbonylPheNlenor-C-Sta methyl ketone
(I, Z=morpholinocarbonylamino; M=phenyl; Q=H; $R_2$=n-butyl; X=cyclohexyl;W=CH ⫶⫶⫶OH; $Z^1$=$COCH_3$)

A. 4(S)-Bocamino-3(R)-benzyloxy-5-cyclohexyl-2-pentanone

3(S)-t-Butoxycarbonylamino-2(R)-benzyloxy-4-cyclohexylbutyraldehyde (315 mg) was dissolved in 4 mL ether at 0° C. and treated with 530 uL 1.9M methylmagnesium bromide in n-butyl ether. After 20 minutes another 530 uL of the Grignard reagent was added and 10 minutes later the reaction was quenched with saturated aqueous ammonium chloride and extracted with ether. The ether layers were washed with 1N NCl, aqueous sodium bicarbonate, brine, dried over sodium sulfate and concentrated giving 580 mg of a yellow oil. This material wa dissolved in 5 mL ether and treated with 1 mL chromic acid solution (Org. Syn. Coll. Vol. 5, p. 310). After 30 minutes the mixture was diluted with ether and washed with 1N sodium hydroxide (4×5 mL), dried over magnesium sulfate, and concentrated to give 250 mg of a light yellow oil which was purified on silica gel (ether-hexanes) giving 125 mg of colorless oil, TLC Rf 0.24 (1:4 System B).

B. 4(S)-amino-3(R)-benzyloxy-5-cyclohexyl-2-pentanone hydrochloride

The product of Example 31A (120 mg) was dissolved in 3 mL 4N HCl-dioxane and stirred at 25° C. for 1.2 hours. The mixture was concentrated and the residue coevaporated 3× with added ether and dried giving 100 mg of a colorless foam, TLC Rf 0.22 (System C, the spotted plate exposed to ammonia prior to elution).

C. morpholinocarbonylPheNlenor-C-Sta methyl ketone benzyl ether

According to the procedure for the preparation and purification of the product of Example 1C, 95 mg of the product of Example 31B and 150 mg of the product of Example 8C gave 180 mg of a pale yellow foam, TLC Rf 0.30 (ethyl acetate, silica).

D. morpholinocarbonylPheNlenor-C-Sta methyl ketone

The product of Example 31C (180 mg) was dissolved in 3 mL methanol and 1 mL acetic acid and shaken with 10% Pd/C (180 mg) at 25° C. and 50 p.s.i. hydrogen for 24 hours. The mixture was filtered, concentrated, coevaporated with added toluene, and dried giving 160 mg of colorless foam which was chromatographed on silica (ethanol-dichloromethane gradient) giving 55 mg of a colorless solid, HPLC 3.37 minutes in 70/30 acetonitrile-pH 2.1 phosphate.

1H NMR, $CDCl_3$, 300 MHz, partial, delta ppm: 0.86 (t, 3H), 2.17 (s, 3H), 3.05 and 3.09 (dd, 1H ea), 3.24 and 3.59 (m, 4H ea), 3.89, 4.08, 4.15, 4.47 and 4.55 (m, 1H ea), 4.92, 6.11 and 6.48 (d, 1H ea), 7.13–7.35 (m, aromatic).

EXAMPLE 32

MorpholinocarbonylPhe O-ETSernor-C-Sta
N-methylamide (I, Z=morpholinocarbonylamino;
M=phenyl; Q=H; $R_2=C_2H_5OCH_2$; X=cyclohexyl;
W=CH∭OH; $Z^1=CONHCH_3$)

A. morpholinocarbonylPhe O-ETSernor-C-Sta N-methylamide TBDMS ether

According to the procedure for preparation and purification of the product of Example 1C, 70 mg of the product of Example 14C and 75 mg of Morpholinocarbonyl Phe O-EtSer gave 50 mg of a colorless solid.

B. morpholinocarbonylPhe O-ETSernor-C-Sta N-methyl amide

The product of Example 32A (48 mg) was dissolved in 2 mL 4N HCl-dioxane and stirred 1 hour at 25° C. The mixture was concentrated, and the residue was coevaporated with ether and dried giving 40 mg of a colorless solid, HPLC 3.46 minutes in 50/50 acetonitrile-pH 2.1 phosphate, TLC Rf 0.28 in System C.

1H NMR, DMSO-D6, 300 MHz, partial, delta ppm: 1.12 (t, 3H), 2.57 (d, 3H), 2.81 and 3.03 (dd, 1H ea), 3.20 (m, 4H), 3.45 (m), 3.78 and 4.13 (m, 1H ea), 4.35 (m, 2H), 5.74, 6.68, 7.54 and 8.08 (d, 1H ea), 7.12-7.35 (m, aromatic).

EXAMPLE 33

MorpholinocarbonylPheNlenor-C-Sta i-propyl ketone
(I, Z=morpholinocarbonylamino; M=phenyl; Q=H;
$R_2$=n-butyl; X=cyclohexyl; W=CH∭OH; and
$Z^1=COCH(CH_3)_2$)

A. 5(S)-Bocamino-4(R)-benzyloxy-6-cyclohexyl-2-methyl-3-hexanone

3(S)-t-Butoxycarbonylamino-2(R)-benzyloxy-4-cyclohexylbutyraldehyde (400 mg) was dissolved in 3 mL ether at 0° C. and treated with 1.17 mL isopropylmagnesium bromide (2.0M in diethylether). After 20 minutes another 0.6 mL of the Grignard reagent was added followed 5 minutes later by 1 mL saturated aqueous sodium bicarbonate, brine, dried over magnesium sulfate and concentrated giving 350 mg of a clear oil. This material was dissolved in 2 mL ether and treated with 2 mL chromic acid solution (Org. Syn. Coll. Vol. V, p. 310) and after 30 minutes the mixture was extracted with ether which was washed with aqueous sodium hydroxide, brine, dried and concentrated to give 250 mg of a yellow oil which was purified on silica (ether-hexanes) giving 125 mg of a light yellow oil, TLC Rf 0.33 (1:4 System A).

B. 5(s)-amino-4(R)-benzyloxy-6-cyclohexyl-2-methyl-3-hexanone hydrochloride

The product of Example 33A (120 mg) was dissolved in 2 mL 4N HCl-dioxane and stirred 1.2 hours at 25° C., concentrated and the residue coevaporated with ether, giving 95 mg of a colorless solid, TLC Rf 0.4 in System C (the spotted plate exposed to ammonia prior to elution).

C. morpholinocarbonylPheNlenor-C-Sta isopropyl ketone benzyl ether

According to the procedure for preparation and purification of the product of Example 1C, 95 mg of the product of Example 33B and 136 mg of the product of Example 8C gave 160 mg of colorless foam, HPLC 3.56 minutes in 85/15 acetonitrile-water.

D. morpholinocarbonylPheNlenor-C-Sta i-propyl ketone

The product of Example 33C (155 mg) was dissolved in 3 mL methanol and 3 mL acetic acid and shaken with 155 mg 10% Pd/C for 18 hours at 25° C., filtered through Celite, concentrated, the residue coevaporated with toluene and ether and dried giving 100 mg of a pale yellow solid, TLC Rf 0.40 (ethyl acetate-silica).

1H NMR, CDCl3, 250 MHz, partial, delta ppm: 0.87 (t, 3H), 1.08 and 1.12 (d, 3H ea), 3.09 (m, 2H), 3.62 (m, 4H), 4.15 (m, 1H), 4.32 (s, 1H), 4.99, 6.38 and 6.51 (d, 1H ea), 7.15-7.37 (m, aromatic).

EXAMPLE 34

MorpholinocarbonylPheNlenor-C-Sta i-butyl ketone (I,
Z=morpholinocarbonylamino; M=phenyl; Q=H;
$R_2$=n-butyl; X=cyclohexyl; W=C∭OH; and
$Z^1=COCH_2CH(CH_3)_2$)

A. 6(S)-Bocamino-5(R)-benzyloxy-7-cyclohexyl-2-methyl-4-hexanone

3(S)-t-Butoxycarbonylamino-2(R)-benzyloxy-4-cyclohexylbutyraldehyde (1.00 g) was dissolved in 10 mL ether at 0° C. and treated with 1.6 mL 2.0M ethereal isobutylmagnesium chloride. After 30 minutes another 3 mL Grignard reagent was added and the solution warmed to 25° C. After another hour, the mixture was quenched with aqueous ammonium chloride solution and extracted with ether. The ether was washed with brine, dried over sodium sulfate and concentrated giving 1.02 g of a clear oil. This material was dissolved in 20 mL ether and treated with 5 mL chromic acid solution (Org. Syn., V, p. 310). After being stirred at 0° C. for 1 hour and 25° C. for 30 minutes, the mixture was diluted with ether and washed with 1N sodium hydroxide, brine, dried over magnesium sulfate, concentrated and the crude product purified on silica (ether-hexane) giving 440 mg of colorless oil, TLC Rf 0.33 in 1:3 System B.

B. 6(S)-amino-5(R)-benzyloxy-7-cyclohexyl-2-methyl-4-hexanone hydrochloride

The product of Example 34A (430 mg) was dissolved in 3 mL 4N HCl-dioxane and stirred 1.2 hours at 25° C., concentrated, thrice coevaporated with ether and dried giving 325 mg of a colorless solid, TLC Rf 0.29 in System C (spotted plate exposed to ammonia prior to elution).

C. morpholinocarbonylPheNlenor-C-Sta i-butyl ketone benzyl ester

According to the procedure for preparation and purification of the product of Example 1C, 150 mg of the product of Example 34B and 207 mg of the product of Example 8C gave 280 mg of colorless foam.

D. morpholinocarbonylPheNlenor-C-Sta i-butyl ketone

The product of Example 34C (300 mg) was dissolved in 10 mL 1:1 methanol-acetic acid and shaken with 300 mg 10% Pd/C for 18 hours at 25° C. and 50 p.s.i. hydrogen. The mixture was filtered through Celite, the filtrates concentrated and coevaporated with added toluene, and the residue chromatographed on silica (ethanol-dichloromethane gradient) giving 180 mg of colorless solid, HPLC 4.40 minutes in 70/30 acetonitrile-pH 2.1 phosphate, TLC Rf 0.31 (ethylacetate-silica).

1H NMR, CDCl$_3$, 300 MHz, partial, delta ppm: 0.84 (t, 3H), 0.90 and 0.92 (d, 3H ea), 2.10 (septet, 1H), 2.38 and 2.53 (dd, 1H ea), 3.04 (m, 2H), 3.26 and 3.58 (m, 4H ea), 4.06 (s, 1H), 4.22, 4.52 and 4.60 (m, 1H ea), 5.26, 6.57 and 7.00 (d, 1H ea), 7.1–7.3 (m, aromatic).

MorpholinocarbonylPheNlenor-C-Sta methoxyamide (I, Z=morpholinocarbonylamino; M=phenyl; Q=H; R$_2$=n-butyl; X=cyclohexyl; W=CH∥∥∥∥OH; and Z$^1$=CONHOCH$_3$)

A. Boc nor-C-Sta methoxyamide

According to the procedure for preparation of the product of Example 1C, 54 mg of methoxyamine hydrochloride and 98 mg of Boc nor-C-Sta (product of Example 1G, U.S. Pat. No. 4,668,769) gave 102 mg of crude product which was purified on silica (ethyl acetate-hexantes) giving 40 mg of the title substance.

B. nor-C-Sta methoxyamide hydrochloride

The product of Example 35A (38 mg) was stirred in 2 mL 4N HCl-dioxane at 25° C. for 1.2 hours and concentrated to a colorless solid which was washed thrice with ether giving 25 mg of solid.

C. morpholinocarbonylPheNle N-hydroxysuccinimide ester

The product of Example 8A (1.05 g) was dissolved in 5 mL dimethoxyethane and treated at 0° C. with 350 mg N-hydroxysuccinimide and 573 mg of dicyclohexylcarbodiimide and stirred overnight in an ice bath which was allowed to warm to 18° C. The mixture was filtered, the filtered solid washed with dimethoxyethane, the filtrates concentrated, and the residue suspended in ethyl acetate. The ethyl acetate suspension was washed with saturated aqueous sodium bicarbonate, brine, dried over magnesium sulfate and concentrated to give 960 mg of a colorless foam.

D. morpholinocarbonylPheNlenor-C-Sta methoxyamide

The product of Example 35B (23 mg) was dissolved in 0.3 mL dimethoxyethane and treated sequentially at 25° C. with 12 uL triethylamine and 42 mg of the product of Example 35C. More dimethoxyethane (200 ul) and 200 uL dichloromethane was added and the mixture was stirred 22 hours, dissolved in 30 mL ethyl acetate, washed with 2×1 mL 1N HCl, 2×2 mL saturated aqueous sodium bicarbonate, dried over magnesium sulfate, concentrated and chromatographed on silica (ethanol-dichloromethane gradient) giving 45 mg of a colorless solid, TLC Rf 0.5 in System C, HPLC 2.84 minutes in 60/40 acetonitrile-pH 2.1 phosphate.

1H NMR, CDCl$_3$, 250 MHz, partial, delta ppm: 0.89 (t, 3H), 3.02 (dd, 1H), 3.14 (m), 3.62 (m, 4H), 3.77 (s, 3H), 4.35, 4.60 and 5.01 (m, 1H ea), 7.13–7.38 (m, aromatic), 9.57 (s, 1H).

EXAMPLE 36

MorpholinocarbonylPheNlenor-C-Statol (I, Z=morpholinocarbonylamino; M=phenyl; Q=H; R$_2$=n-butyl; X=cyclohexyl; W=CH∥∥∥∥OH; and Z$^1$=CH$_2$OH)

A. 3(S)-amino-2(R)-benzyloxy-4-cyclohexyl-1-butanol

3(S)-t-Butoxycarbonylamino-2(R)-benzyloxy-4-cyclohexyl-1-butanol (108 mg) (U.S. Pat. No. 4,668,769), Example 1J was dissolved in 0.5 mL ether and cooled to 0° C. Into this solution was introduced excess anhydrous HCl and the solution was stirred at 25° C. for 2 hours and concentrated giving 88 mg of colorless solid, TLC Rf 0.28 in System A.

B. 3(S)-(morpholinocarbonylPheNleamino)-2(R)-benzyloxy-4-cyclohexyl-1-butanol The product of Example 36A (85 mg) was dissolved in 500 uL dimethoxyethane and treated sequentially at 0° C. with 38 uL triethylamine and 132 mg of the product of Example 35C. After 18 hours, the mixture was concentrated and chromatographed on silica (ethyl acetate-hexanes) giving 139 mg of a colorless solid, TLC Rf 0.25 (ethyl acetate-silica).

C. morpholinocarbonylPheNlenor-C-Statol

The product of Example 36B (80 mg) and 90 mg of 10% Pd/C were mixed in 5 mL methanol and 5 mL acetic acid and shaken at 48 p.s.i. hydrogen and 25° C. for 21 hours. The mixture was concentrated and the residue was chromatographed on silica (ethanol-dichloromethane gradient) giving 64 mg colorless solid, TLC Rf 0.5 in System C, HPLC 4.95 minutes in 50/50 acetonitrile-water.

1H NMR, CDCl$_3$, 250 MHz, partial, delta ppm: 0.92 (t, 3H), 2.94 (dd, 1H), 3.09–3.72 (overlapping m), 4.12–4.37 (m, ca. 3H), 4.79, 6.28 and 6.93 (d, 1H ea), 7.20–7.48 (m, aromatic).

EXAMPLE 37

MorpholinocarbonylPhe S-MeCysnor-C-Sta i-butyl ketone (I, Z=morpholinocarbonylamino; M=phenyl; Q=H; R$_2$=CH$_3$SCH$_2$; X=cyclohexyl; W=CH∥∥∥∥OH; and Z$^1$=COCH$_2$CH(CH$_3$)$_2$)

A. morpholinocarbonylPhe S-MeCysnor-C-Sta i-butyl ketone benzyl ether

According to the procedure for preparation and purification of the product of Example 1C, 120 mg of the product of Example 34B and 129 mg of Mor-Phe-SMe-Cys gave 114 mg of a colorless powder, TLC Rf 0.58 in System C.

B. morpholinocarbonylPhe S-MeCysnor-C-Sta i-butyl ketone

The product of Example 37A (95 mg) was dissolved in 1.0 mL formic acid and 100 mg of palladium black (ALFA Co.) was added. After stirring overnight the mixture was filtered through Celite, concentrated and the residue was coevaporated with toluene and dried giving 97 mg of a tan oil which was purified on silica (ethanol-dichloromethane gradient) giving 23.5 mg of colorless powder, TLC Rf 0.65 in System C, 3.65 minutes by HPLC in 70/30 acetonitrile-pH 2.1 phosphate.

1H NMR, CDCl$_3$, 300 MHz, partial, delta ppm: 0.90 and 0.92 (d, 3H ea), 2.10 (s, 3H), 2.14 (septet, 1H), 2.38, 2.56, 2.65, 2.92, 3.00 and 3.14 (dd, 1H ea), 3.14–3.37 (m), 3.60 (m, 4H), 3.97, 4.05 and 4.65 (m, 1H ea), 4.41–4.56 (m, 2H), 6.76 and 6.86 (d, 1H ea), 7.14–7.36 (m, aromatic).

EXAMPLE 38

BocPhe S-MeCysnor-C-Sta i-propyl ester (I, Z=t-(CH$_3$)$_3$COCONH; M=phenyl; Q=H; R$_2$=CH$_3$SCH$_2$; X=cyclohexyl; W=CH∥∥∥∥OH; and Z$^1$=CO$_2$CH(CH$_3$)$_2$)

A. BocPhe S-MeCys

S-methylcysteine (6.26 g) was dissolved in 65 mL of saturated aqueous sodium bicarbonate at 25° C. and 35 mL THF was added. This solution was treated in one portion with 12.0 g of N-t-boc-L-phenylalanine hydroxysuccinimide ester. After 30 minutes the solution was transferred to a separatory funnel and washed twice with ethyl acetate. A fresh portion of ethyl acetate was added and the pH was adjusted to 1.1 with 6N HCl. The organic layer was separated and the aqueous layer was extracted with ethyl acetate (4x). The combined organic layers were washed twice with 1N HCl, brine, dried over magnesium sulfate and concentrated giving 12.0 g of a colorless foam.

B. BocPhe S-MeCysnor-C-Sta i-propyl ester

Nor-C-Sta isopropyl ester (1.0 g) was dissolved in 20 mL dichloromethane and treated sequentially with 1.57 g (1.0 equiv) of the product of Example 38A, 945 mg (1.5 equiv) of hydroxybenzotriazole hydrate and 788 mg (1.0 equiv) 1-(3-dimethylaminopropyl)-3-ethylcarbodiimide hydrochloride (DEC). The reaction mixture was stirred in an ice bath which was allowed to reach 18° C. overnight. The mixture was concentrated, the residue dissolved in ethyl acetate and the resulting solution washed twice with 1N HCl, twice with 1N NaOH, once with brine, dried over magnesium sulfate and concentrated to give a colorless solid which was purified on silica (ethyl acetate-hexanes) giving 1.85 g of the title substance as a colorless powder. TLC Rf 0.60 in System C.

1H NMR, CDCl$_3$, 300 MHz, partial, delta ppm: 0.94 (m), 1.29 and 1.30 (d, 3H ea), 13.9 (s, 9H), 2.13 (s, 3H), 2.64, 2.98, 3.03 and 3.15 (dd, 1H ea), 4.09 (d, 1H), 4.30–4.50 (m, 3H), 4.90 (m, 1H), 5 07 (septet, 1H), 6.66 (m, 1H), 6.86 (d, 1H), 7.16–7.36 (m, aromatic).

EXAMPLE 39

Phe S-MeCysnor-C-Sta i-propyl ester (I, Z=NH$_2$; M=phenyl; Q=H; R$_2$=CH$_3$SCH$_2$; X=cyclohexyl; W=CH∥∥∥∥OH; and Z$^1$=COC$_2$CH(CH$_3$)$_2$)

The product of Example 38B (500 mg) was dissolved in 3 mL 4N HCl-dioxane and stirred at 25° C. for 40 minutes. The mixture was concentrated and the residue coevaporated with ether giving 460 mg of an off-white powder, TLC Rf 0.25 in System C (substance was treated with triethylamine in dichloromethane and then applied to the TLC plate), HPLC 4.05 minutes in 50/50 acetonitrile-pH 2.1 buffer.

1H NMR, DMSO, 250 MHz, partial, delta ppm: 1.20 (overlapping d, 6H), 2.11 (s, 3H), 2.55 (2.82, 2.93 and 3.18 (dd, 1H ea), 4.01, 4.08, 4.23 and 4.57 (m, 1H ea), 7.30 (s, aromatic), 5.38, 7.96 and 8.89 (d, 1H ea), 8.18 (br, 3H).

EXAMPLE 40

4-PicolinoylPhe S-MeCysnor-C-Sta i-propyl ester (I, Z=4-picolinoylamino; M=phenyl; Q=H; R$_2$=CH$_3$SCH$_2$—; X=cyclohexyl; W=CH∥∥∥∥OH; and Z$^1$=CO$_2$CH(CH$_3$)$_2$)

According to the procedure for preparation and purification of the product of Example 38B, with the exception that 1.05 equiv triethylamine (54 uL) was used to neutralize the starting amine hydrochloride, 200 mg of the product of Example 39 and 45 mg of pyridine-4-carboxylic (picolinic) acid gave 157 mg of a colorless powder, TLC Rf 0.52 in System C, HPLC 7.10 minutes in 50/50 acetonitrile-pH 2.1 phosphate.

1H NMR, DMOS, 250 MHz, partial, delta ppm: 1.18 and 1.20 (d, 3H ea), 2.09 (s, 3H), 2.60, 2.80 and 3.14 (dd, 1H ea), 4.00, 4.22, 4.49 and 4.78 (m, 1H ea), 4.87 (septet, 1H), 5.35, 7.18, 8.42 and 8.90 (d, 1H ea), 7.26 (t, 2H), 7.37 (d, 2H), 7.67 (d, 2H), 8.70 (d, 2H).

EXAMPLE 41

4-t-BocpiperazinocarbonylPhe S-MeCysnor-C-Sta i-propyl ester (I, Z=4-t-Bocpiperazinocarbonylamino; M=phenyl; Q=H; R$_2$=CH$_3$SCH$_2$—; X=cyclohexyl; W=CH∥∥∥∥OH; and Z$^1$=CO$_2$CH(CH$_3$)$_2$)

A. 4-t-BocpiperazinocarbonylPheS-MeCys methyl ester

According to the procedure for preparation of the product of Example 38B, 245 mg of S-methyl-cysteine methyl ester and 500 mg of Boc-piperazinecarbonyl-L-phenylalanine gave 547 mg of a colorless foam which was used without further purification.

B. 4-t-BocpiperazinocarbonylPhe S-MeCYs

The product of Example 41A (467 mg) was dissolved in 1 mL dioxane and 0.5 mL water at 0° C. and treated with 33 mg lithium hydroxide. After 2.5 hours the mixture was concentrated, the residue dissolved in water and the resulting solution extracted with ether. Ethyl acetate was added to the aqueous layer which was brought to pH 1 with 1N HCl, extracted with ethyl acetate (4x), the extracts washed with water and dried over magnesium sulfate giving 417 mg of a colorless solid.

C. 4-t-BocpiperazinocarbonylPhe S-MeCysnor-C-Sta i-propyl ester

According to the procedure for preparation and purification of the product of Example 36B, 100 mg of nor-C-Sta isopropyl ester and 203 mg of the product of Example 41B gave 182 mg of colorless solid, TLC Rf 0.49 (ethyl acetate/silica).

1H NMR, CDCl$_3$, 250 MHz, partial, delta ppm: 1.26 and 1.27 (d, 3H ea), 1.45 (s, 9H), 2.10 (s, 3H), 2.73 (dd, 1H), 3.00 (m, 2H), 3.27 and 3.36 (m, 9H total), 3.77 (d, 1H), 4.10 (dd, 1H), 4.44 (m, 1H), 4.81 (d, 1H), 5.07 (septet, 1H), 6.84 and 6.93 (d, 1H ea), 7.18–7.39 (m, aromatic).

EXAMPLE 42

PiperazinocarbonylPhe S-MeCysnor-C-Sta i-propyl ester (I, Z=piperazinocarbonylamino; M=phenyl; Q=H; R$_2$=CH$_3$SCH$_2$—; X=cyclohexyl; W=CH∥∥∥∥OH; and Z$^1$=CO$_2$CH(CH$_3$)$_2$)

The product of Example 41 (33 mg) was dissolved in 2 mL 4N HCl-dioxane and stirred at 25° C. for 50 minutes, concentrated and the residue coevaporated with ether giving 31 mg of an off-white powder, TLC Rf 0.2 in System C (spotted plate exposed to ammonia prior to elution), HPLC 2.98 minutes in 50/50 acetonitrile-pH 2.1 phosphate.

1H NMR, DMSO, 250 MHz, partial, delta ppm: 1.18 and 1.20 (d, 3H ea), 2.10 (s, 3H), 4.00 and 4.21 (m, 1H ea), 4.40 (m, 2H), 4.85 (septet, 1H), 5.33, 6.90, 7.63 and 8.22 (d, 1H ea), 7.13–7.33 (m, aromatic).

EXAMPLE 43

MorpholinocarbonylhexahydroPhe S-MeCysnor-C-Sta i-propyl ester (I, Z=morpholinocarbonylamino; M=cyclohexyl; Q=H; $R_2$=$CH_3SCH_2$; X=cyclohexyl; W=CH ⅢⅢⅢOH; and $Z^1$=$CO_2CH(CH_3)_2$)

A. morpholinocarbonylhexahydro-L-phenylalanine

The product of Example 7C (4.0 g) was dissolved in 55 mL 10:1 methanol-acetic acid and shaken with 1.0 g 10% Rh/C under 50 p.s.i. hydrogen at 25° C. for 3.5 hours. The mixture was filtered through Celite, concentrated, and coevaporated with ether giving 4.15 g of a colorless foam which was purified on silica (packed and loaded in ethyl acetate, eluted in the same followed by an ethanol-dichloromethane gradient) giving 704 mg of a colorless foam, TLC Rf 0.4.

B. morpholinocarbonylhexahydroPhe hydroxy succinimide ester

The product of Example 43A (700 mg) was dissolved in 5 mL dimethoxyethane and treated sequentially at 0° C. with 283 mg N-hydroxysuccinimide and 507 mg dicyclohexylcarbodiimide. The reaction mixture was allowed to warm to 18° C. overnight, filtered, concentrated, the residue dissolved in ethyl acetate which was washed twice with saturated aqueous sodium bicarbonate, brine, dried over magnesium sulfate and concentrated giving 704 mg of a colorless foam.

C. morpholinocarbonylhexahydroPhe S-MeCys

S-methylcysteine (442 mg) was dissolved in 4.6 mL saturated aqueous sodium bicarbonate and 2.5 mL of THF was added followed by 890 mg of the product of Example 43B. After stirring 20 minutes at 25° C. the mixture was diluted with water, washed twice with ethyl acetate and brought to pH 1.1 with 1N HCl in the presence of ethyl acetate. The organic layer was separated, the aqueous layer was extracted with four portions of ethyl acetate, the combined organic layers were washed twice with 1N HCl, brine, dried over magnesium sulfate and concentrated giving 796 mg of a colorless foam.

D. morpholinocarbonylhexahydroPhe S-MeCysnor-C-Sta i-propyl ester

According to the procedure for preparation and purification of the product of Example 38B, 94 mg of nor-C-Sta isopropyl ester and 170 mg of the product of Example 43C gave 178 mg of colorless powder, TLC Rf 0.83 in System C, HPLC 4.16 minutes 70/30 acetonitrile-pH 2.1 phosphate.

1H NMR, CDCl$_3$, 250 MHz, partial, delta ppm: 0.93 (m, 4H), 1.26 and 1.27 (d, 3H ea), 2.13 (s, 3H), 2.76 and 3.11 (dd, 1H ea), 3.39 (m, 4H), 3.70 (m, 4H), 4.08 (br, 1H), 4.28 (m, 1H), 4.41 (m, 2H), 4.82, 6.83 and 6.93 (d, 1H ea), 5.04 (septet, 1H).

EXAMPLE 44

BocProPhe S-MeCysnor-C-Sta i-propyl ester (I, Z=Bocpyrrolidyl-2-carbonylamino; M=phenyl; Q=H; $R_2$=$CH_3SCH_2$—; X=cyclohexyl; W=CH ⅢⅢⅢOH; and $Z^1$=$CO_2CH(CH_3)_2$)

According to the procedure for preparation and purification of the product of Example 38B, except that 1.2 equiv, 71 uL of triethylamine was used to neutralize the amine hydrochloride, 233 mg of the product of Example 39 and 101 mg of boc-L-proline gave 237 mg of colorless powder, TLC Rf 0.66 in System C.

1H NMR, CDCl$_3$, 250 MHz, partial, delta ppm: 1.27 and 1.29 (d, 3H ea), 1.48 (s, 9H), 2.13 (s, 3H), 2.67 and 3.04 (dd, 1H ea), 4.44 (m, 1H), 4.62 (m, 2H), 5.07 (septet, 1H), 6.42 and 6.60 (d, 1H), 7.1–7.4 (m, aromatic).

EXAMPLE 45

ProPhe S-MeCysnor-C-Sta i-propyl ester hydrochloride (I, Z=(s)-2-pyrrolidylcarbonylamino; M=phenyl; Q=H; $R_2$=$CH_3SCH_2$—; X=cyclohexyl; W=CH ⅢⅢⅢOH;) and $Z^1$=$CO_2CH(CH_3)_2$)

The product of Example 44 (124 mg) was dissolved in 3 mL 4N HCl-dioxane and stirred at 25° C. for 40 minutes. The mixture was evaporated giving 114 mg of a pale yellow powder, TLC Rf 0.39 in System C (the spotted plate was exposed to ammonia prior to elution).

1H NMR, DMSO, 250 MHz, partial, delta ppm: 1.27 and 1.29 (d, 3H ea), 2.09 (s, 3H), 2.56 (dd, 1H), 4.00, 4.08, 4.22, 4.47 and 4.64 (m, 1H ea), 4.85 (septet, 1H), 5.37, 7.73, 8.41 and 8.78 (d, 1H ea), 7.13–7.33 (m, aromatic).

EXAMPLE 46

O-Succinoyl morpholinocarbonylPhe S-MeCysnor-C-Sta i-propyl ester (I, Z=morpholinocarbonylamino; M=phenyl; Q=H; $R_2$=$CH_3SCH_2$; X=cyclohexyl; W=CH ⅢⅢⅢ$OCO(CH_2)_2CO_2H$; and $Z^1$=$CO_2CH(CH_3)_2$)

The product of Example 17E (101 mg) was dissolved in 0.8 mL dichloromethane and treated with 16 mg of succinic anhydride and 13 uL pyridine. After stirring 18.5 hours at 25° C. 20 mg dimethylaminopyridine was added. Four hours later 40 mg succinic anhydride was added. After stirring an additional 20 minutes the mixture was diluted with ethyl acetate and washed three times with 1N HCl, brine, dried over magnesium sulfate, concentrated and chromatographed on silica eluting first with ethyl acetate then with 4% ethanol in dichloromethane, giving 59 mg of colorless powder, TLC Rf 0.1 (ethyl acetate, silica, HPLC 2.84 minutes in 70/30 acetonitrile-pH 2.1 phosphate.

1H NMR, CDCl$_3$, 300 MHz, partial, delta ppm: 0.94 (m), 1.24 and 1.27 (d, 3H ea), 2.10 (br, 3H), 2.64–3.54 (m), 3.6 (m, 4H), 4.23, 4.53 and 4.67 (m, 1H ea}, 4.96 (br, 1H), 4.98 (septet, 1H), 5.14 (br, 1H), 6.65 (d, 1H), 7.16–7.39 (m, aromatic).

EXAMPLE 47

MorpholinocarbonylPhe N-MeNlenor-C-Sta i-propyl ester (I, Z=morpholinocarbonylamino; M=phenyl; Q=$CH_3$; $R_2$=n-butyl; X=cyclohexyl; W=CH ⅢⅢⅢOH; and $Z^1$=$CO_2CH(CH_3)_2$)

According to the procedure for preparation and purification of the product of Example 38B, 76 mg of nor-C-

Sta isopropyl ester and 126 mg of the product of Example 30E gave 117 mg of colorless foam, TLC Rf 0.68 in System C. The desired product of this mixture was isolated by preparative HPLC on a 9.8×250 mm Zorbax C-8 column, 6.3 mL/min of 75/25 acetonitrile-water, ret. time 5.61 minutes, separated from an undesired inactive component at 6.42 minutes. Colorless foam (60 mg) was thus obtained, analytical HPLC 4.98 minutes in 75/25 acetonitrile-water.

1H NMR, CDCl$_3$, 250 MHz, partial, delta ppm: 0.83 (t, 3H), 1.23 and 1.26 (d, 3H ea), 2.70 (s, 3H), 2.95 and 3.09 (dd, 1H ea), 3.22–3.45 (m, 4H), 3.65 (m, 4H), 4.02 and 4.05 (d, 1H total), 4.95 (m, 2H), 5.15 and 7.75 (d, 1H ea), 7.14–7.38 (m, aromatic).

EXAMPLE 48

PiperidinocarbonylPhe S-MeCysnor-C-Sta i-propyl ester (I, Z=piperidinocarbonylamino; M=phenyl; Q=H; R$_2$=CH$_3$SCH$_2$—; X=cyclohexyl; W=CH⁞⁞⁞⁞⁞⁞OH; and Z$^1$=CO$_2$CH(CH$_3$)$_2$)

A. piperidinocarbonylPhe benzyl ester

The product of Example 7A (1.74 g) was dissolved in 13 mL dichloromethane and treated with 0.61 mL piperidine at 0° C. After 15 minutes 0.1 mL piperidine was added and the solution was evaporated and the residue chromatographed on silica eluting with ethyl acetate-hexanes giving 1.61 g of a colorless oil, TLC Rf 0.36 in 1:1 System A.

B. piperidinocarbonylPhe

The product of Example 48A (1.6 g) was dissolved in 50 mL 10:1 methanol-acetic acid and shaken with 0.6 g 10% Pd/C at 50 p.s.i. hydrogen and 25° C. for 30 minutes. The mixture was filtered through Celite, the filtrate evaporated and the residue coevaporated first with added toluene then with ether giving 1.17 g of a colorless foam, TLC Rf 0.50 in System C.

C. Boc S-MeCysnor-C-Sta i-propyl ester

According to the procedure for preparation and purification of the product of Example 38B, 900 mg of nor-C-Sta isopropyl ester and 871 mg of Boc-S-methyl-L-cysteine gave 1.04 g of a colorless powder, TLC Rf 0.42 in 1:1 System A.

D. S-MeCysnor-C-Sta i-propylester hydrochloride

The product of Example 48C (1.03 g) was dissolved in 6 mL 4N HCl-dioxane, stirred 45 minutes at 25° C. and concentrated giving 998 mg of colorless solid, TLC Rf 0.48 in System C.

E. piperidinocarbonylPhe S-MeCysnor-C-Sta i-propyl ester

According to the procedure for preparation and purification of the product of Example 38B, except that triethylamine was used to neutralize the amine hydrochloride, 130 mg of the product of Example 48D and 90 mg of the product of Example 48B gave 117 mg of colorless solid, TLC Rf 0.44 (ethyl acetate-silica).

1H NMR, CDCl$_3$, 250 MHz, partial, delta ppm: 1.27 and 1.29 (d, 3H ea), 2.08 (s, 3H), 2.75, 2.92, 3.13 and 3.31 (dd, 1H ea), 3.20 (m), 4.11 (s, 2H), 4.33–4.58 (m), 4.72 and 6.90 (d, 1H ea), 5.09 (septet, 1H), 7.19–7.4 (m, aromatic).

EXAMPLE 49

MorpholinocarbonylPheNlenor-C-Sta 2-hydroxy-i-butyl ketone (I, Z=morpholinocarbonylamino; M=phenyl; Q=H; R$_2$=n-butyl; X=cyclohexyl; W=CH⁞⁞⁞⁞⁞⁞OH; and Z=COCH$_2$C(OH)(CH$_3$)$_2$)

A. 6(S)-Bocamino-5(R)-benzyloxy-7-cyclohexyl-2-methyl-2-hydroxy-4-hexanone

3(S)-t-butoxycarbonylamino-2(R)-benzyloxy-4-cyclohexylbutyraldehyde (475 mg) was added at −78° C. to a solution of 2.5 equiv of lithio ethyl acetate (from 5 mL THF, 392 uL diisopropylamine and 1.75 mL 1.6M n-butyllithium in hexane at 0° C. followed by 272 uL ethyl acetate at −78° C.), stirred 10 minutes at −78° C. and 10 minutes at 0° C. and quenched with aqueous ammonium chloride. The products were isolated by ether extraction giving 548 mg of isomeric substances (TLC Rf 0.35 and 0.28 in 1:1 System B). This material together with 217 mg of the same substances prepared identically but separately were dissolved in 8 mL THF and treated with 5.9 mL 1.3M ethereal methyllithium at 0° C., stirred 5 minutes and quenched with aqueous ammonium chloride solution. A yellowish oil (702 mg) was obtained by ether extraction. TLC Rf 0.2 in 1:1 System B. This material was dissolved in 25 mL acetone and treated with 2 mL chromic acid solution (Org. Syn. Coll. Vol. V, p. 310) and concentrated, dissolved in water and repeatedly extracted with ethyl acetate which was dried over magnesium sulfate, concentrated and purified on silica giving 172 mg of colorless solid, TLC Rf 0.34 in 1:1 System B.

B. 6(S)-amino-5(R)-benzyloxy-7-cyclohexyl-2-methyl-2-hydroxy-4-hexanone hydrochloride The product of Example 49A (124 mg) was dissolved in 0.5 mL trifluoroacetic acid at 0° C., stirred 20 minutes, concentrated and the residue coevaporated with toluene, ether and ether containing 1.1 equiv HCl (in dioxane) giving after drying 106 mg of a yellowish oil.

C. morpholinocarbonylPheNlenor-C-Sta 2-hydroxy-i-butyl ketone benzyl ether

According to the procedure for preparation and purification of the product of Example 38B, except that triethylamine was added to neutralize the amine hydrochloride, 104 mg of the product of Example 49B and 106 mg of the product of Example 8C gave 60 mg of colorless solid, TLC Rf 0.4 (ethyl acetate/silica).

D. morpholinocarbonylPheNlenor-C-Sta 2-hydroxy-i-butyl ketone

The product of Example 49C (58 mg) was dissolved in 10 mL 1:1 acetic acid-methanol and shaken with 100 mg 10% Pd/C for 20 hours at 25° C. and 50 p.s.i. hydrogen pressure. The mixture was filtered through Celite, concentrated and purified on silica in ethyl acetate/hexanes giving 20 mg of colorless powder, TLC Rf 0.22 (ethyl acetate/silica).

1H NMR, CDCl$_3$, 250 MHz, partial, delta ppm: 0.88 (t, 3H), 1.27 (s, 6H), 2.76 and 2.87 (d, 1H ea), 3.00 and 3.16 (dd, 1H), 3.26 (m, 4H), 3.63 (m, 4H), 4.16 (br, 1H), 4.23 (m, 1H), 4.51 (m, 2H), 5.00, 6.62 and 6.73 (d, 1H ea), 7.13–7.36 (m, aromatic).

EXAMPLE 50

4-HydroxypiperidinocarbonylPhe S-MeCysnor-C-Sta i-propyl ester (I, Z=4-hydroxypiperidinocarbonylamino; M=phenyl; Q=H; R$_2$=CH$_3$SCH$_2$—; X=cyclohexyl; W=CH⫶⫶OH; and Z$^1$=CO$_2$CH(CH$_3$)$_2$)

A solution of 150 mg of the product of Example 39 and 40 uL triethylamine in 0.8 mL dichloromethane was added at 0° C. to a 0° C. solution of 49 mg carbonyldiimidazole and 20 mg imidazole in 0.3 mL dichloromethane and the resulting solution was stirred 1 hour at 0° C. A solution of 25 mg 4-hydroxypiperidine in 0.3 mL dichloromethane was added and the mixture was stirred 1.5 hours at 0° C. and at 20° C. for 20 hours, diluted with ethyl acetate and washed with 1N HCl (2×), brine, dried over magnesium sulfate concentrated and purified on silica giving 26.1 mg of a colorless foam, TLC Rf 0.22 (ethyl acetate/silica), HPLC 3.10 minutes in 60/40 acetonitrile-pH 2.1 phosphate.

1H NMR, CDCl$_3$, 250 MHz, partial, delta ppm: 1.27 and 1.29 (d, 3H ea), 2.10 (s, 3H), 2.73 and 3.30 (dd, 1H ea), 3.03 (m, 3-4H), 3.58 (m, 2H), 3.87 (m, 1H), 4.10 (m, 1H), 4.45 (m, 3H), 4.82 (d, 1H), 5.08 (septet, 1H), 6.91 and 7.09 (d, 1H ea), 7.19–7.40 (m, aromatic).

EXAMPLE 51

Methyl 3(S)-(BocPheHisamino)-2(S)-azido-4-cyclohexylbutyrate as a mixture with 3(R), 2(R), isomer (I, Z=Bocamino; M=phenyl; Q=H; R$_2$=imidazol-4-ylmethyl; X=cyclohexyl; W=CH ◂▬ N$_3$; and Z$^1$=CO$_2$CH$_3$)

A. racemic methyl 3(S)-Bocamino-4-cyclohexyl-2(R)-hydroxybutyrate

Ten grams of a mixture of 80% N-t-butoxycarbonyl-(S)-3-amino-(R)-2-hydroxy-4-phenylbutyronitrile and 20% of the corresponding 2(S) isomer (U.S. Pat. No. 4,668,769) was heated at reflux for 18 hours in a mixture of 80 mL p-dioxane, 30 mL water and 30 mL conc. HCl, evaporated, the residue dissolved in water and the solution washed with chloroform (3×). The aqueous solution was chilled and brought to pH 7.5 with HCl. The precipitate was filtered, washed with water, acetone and dried giving 4.10 g of a light greenish solid. This material was dissolved in 40 mL p-dioxane and 20 mL water, the solution brought to pH 11 with sodium hydroxide and treated with 5.85 mL di-t-butyldicarbonate. The pH was maintained between 9.5 and 11.2 with sodium hydroxide and after 1.5 hours the mixture was partially concentrated, the residual aqueous solution washed 3x with ether, then acidified to pH 1.0 in the presence of ethyl acetate, separated, extracted further with ethyl acetate, the extracts dried over sodium sulfate and concentrated giving 4.7 g of a light yellow solid, TLC Rf 0.38 in system C. This material was dissolved in 100 mL methanol containing 12 mL acetic acid and shaken with 1.1 g 10% Rh/C for 5.5 hours at 25° C. and 58 p.s.i. hydrogen, filtered and evaporated giving 4.58 g of yellow foam, TLC Rf 0.45 in System C. This material was dissolved in ether and treated with excess ethereal diazomethane, then with acetic acid to quench excess diazomethane, concentrated and purified on silica (ethyl acetate-hexanes giving 4.3 g of a waxy solid, TLC Rf 0.5 (1:1 System A), [a]$^D$ 20 essentially zero (CHCl$_3$, c=1.1).

B. racemic methyl 3(S)-Bocamino-4-cyclohexyl-2(S)-azidobutyrate

Two grams of the product of Example 51A, 4.16 g triphenylphosphine and 12.1 mmol hydrazoic acid (from sodium azide and sulfuric acid in benzene/water, the benzene dried over sodium sulfate and titrated with standard base) were dissolved in 60 mL total benzene at 0° C. and treated with 2.49 mL diethylazodicarboxylate. The mixture was stirred 30 minutes, filtered, concentrated and purified on silica (ether-hexanes) giving 1.02 g of a waxy, off-white solid, TLC Rf 0.48 in 1:3 System A.

C. Racemic methyl 3(S)-amino-4-cyclohexyl-2(S)-azidobutyrate hydrochloride

The product of Example 51B (430 mg) was dissolved in 15 mL 4N HCl dioxane, stirred 1 hour at 25° C. and evaporated giving 355 mg of off-white foam, TLC Rf 0.22 in System C.

D. methyl3(S)-(BocPheHis(imBoc)amino)-2(S)-azido-4-cyclohexylbutyrate as a 1:1 mixture with the 3(R),2(R) isomer According to the procedure for preparation and purification of the product of Example 1C, 340 mg of the product of Example 51C and 710 mg of BocPheHis(Im-Boc) gave 620 mg of the title substances, TLC Rf 0.45 and 0.47 (5% ethanol-dichloromethane) as a colorless foam.

E. methyl 3(S)-(BocPheHisamino)-2(S)-azido-4-cyclohexylbutyrate as a mixture with the 3(R),2(R) isomer The product of Example 51D (380 mg) was dissolved in 10 mL 5:1 acetic acid-water, stirred 4 hours at 25° C., concentrated, coevaporated first with added toluene, then ether and dried, giving 280 mg of light yellow foam.

1H NMR, CDCl$_3$, 300 MHz, partial, delta ppm: 1.37 (s, 9H), 3.76 and 3.78 (s, ca. 1:1 ratio, 3H total), 6.80 (s, 1H), 7.53 and 7.55 (s, 1:1, 1H total).

EXAMPLE 52

Methyl 3(S)-(BocPheHisamino)-2(S)-amino-4-cyclohexylbutyrate as a mixture with the 3(R),2(R)isomer (I, Z=Bocamino; M=phenyl; Q=H; R2=imidazol-4-ylmethyl; X=cyclohexyl; W=CH ◂▬ NH$_2$; and Z$^1$=CO$_2$CH$_3$)

The product of Example 51D (275 mg) was dissolved in 20 mL ethanol containing 0.5 mL acetic acid and shaken with 100 mg 10% Pd/C for 3 hours at 25° C. and 50 p.s.i. hydrogen, filtered and concentrated giving 240 mg of light brown solid, HPLC 5.64 and 7.01 minutes in 60/40 acetonitrile-pH 2.1 phosphate.

1H NMR, CDCl$_3$, 300 MHz, partial, delta ppm: 1.33 and 1.35 (s, 9H total), 3.72 (s, 3H total), 6.78 (s, 1H total).

EXAMPLE 53

Methyl
3(S)-(BocPheHisamino)-2(R)-azido-4-cyclohexylbutyrate as a mixture with 3(R),2(S)isomer (I, Z=Bocamino; M=phenyl; Q=H; $R_2$=imidazol-4-ylmethyl; X=cyclohexyl; W=CH⫶⫶⫶⫶ $N_3$; and $Z^1$=$CO_2CH_3$)

A. racemic methyl 3(S)-Bocamino-4-cyclohexyl-2(S)-benzoyloxybutyrate

A solution of 600 mg of the product of Example 51A, 700 mg benzoic acid and 1.5 g triphenylphosphine in 5 mL THF was treated at 25° C. with 0.9 mL diethylazodicarboxylate. After 1.5 hours 230 mg benzoic acid, 0.5 g triphenylphosphine and 0.3 mL diethylazodicarboxylate was added and 3 hours later the mixture was cooled to 0° C. for 12 hours. The mixture was purified on silica (ethylacetate/hexanes) giving 509 mg of colorless solid, TLC Rf 0.41 in 1:3 System A.

B. racemic methyl 3(S)-Bocamino-4-cyclohexyl-2(S)-hydroxybutyrate

The product of Example 53A (550 mg) was dissolved in 5 mL methanol and treated at 25° C. with 9 mg anhydrous potassium carbonate. After 1.8 hours the mixture was concentrated and the residue purified on silica giving 326 mg of oily foam, TLC Rf 0.18 in 1:3 System A.

C. racemic methyl 3(S)-Bocamino-4-cyclohexyl-2(R)-azidobutyrate

According to the procedure for the preparation and purification of the product of Example 51B, 320 mg of the product of Example 53B gave 280 mg of colorless waxy solid, TLC Rf 0.50 in 1:3 System B.

D. racemic methyl 3(S)-amino-4-cyclohexyl-2(R)-azidobutyrate hydrochloride

According to the procedure for preparation of the product of Example 51C, 260 mg of the product of Example 53C gave 198 mg of light yellow solid.

E. methyl 3(S)-(BocPheHis(imBoc)-amino)-2(R)-azido-4-cyclohexylbutyrate as a mixture with 3(R),2(S) isomer According to the procedure for preparation and purification of the product of Example 1C, 192 mg of the product of Example 53D and 398 mg of BocPheHis(imBoc) (U.S. Pat. No. 4,559,198) gave 253 mg of a light yellow faom, TLC Rf 0.5 (ethyl acetate).

F. methyl 3(S)-(BocPheHisamino)-2(R)-azido-4-cyclohexylbutyrate as a mixture with the 3(R),2(S) isomer The product of Example 53E (211 mg) was stirred 4 hours at 25° C. in 12 mL 5:1 acetic acid-water, concentrated and dried giving 210 mg of light yellow foam, TLC Rf 0.1 in System C.

1H NMR, $CDCl_3$, 300 MHz, partial, delta ppm: 1.30 and 1.34 (s, 3:2 ratio, 9H total), 3.76 and 3.81 (s, 3:2 ratio, 3H total), 6.67 and 6.78 (s, 2:3 ratio, 1H total), 7.52 and 7.55 (s, 2:3 ratio, 1H total).

EXAMPLE 54

Methyl
3(S)-(BocPheHis-amino)-2(R)-amino-4-cyclohexylbutyrate as a mixture with the 3(R),2(S) isomer (I, Z=Bocamino; M=phenyl; Q=H; $R_2$=imidazol-4-ylmethyl; X=cyclohexyl; W=CH⫶⫶⫶⫶ $NH_2$; and $Z^1$=$CO_2CH_3$)

The product of Example 53F (170 mg) was dissolved in 15 ml ethanol and 0.4 mL acetic acid and shaken with 90 mg 10% Pd/C for 1.5 hours at 25° C. and 50 p.s.i. hydrogen, filtered, concentrated, coevaporated with ether and toluene and dried giving 170 mg of light brown solid, HPLC 5.17 and 6.17 minutes (ca. 1:1) in 35/65 acetonitrile-pH 2.1 phosphate.

1H NMR, DMSO-$d_6$, 300 MHz, partial, delta ppm: 1.29 (s, 9H), 3.56 and 3.61 (s, 3:2 ratio, 3H total), 6.80 and 7.50 (s, 1H ea).

EXAMPLE 55

MorpholinocarbonylPheLeunor-C-Sta methyl ester (I, Z=morpholinocarbonylamino; M=phenyl; Q=H; $R_2$=$CH_2CH(CH_3)_2$; X=cyclohexyl; W=CH⫶⫶⫶⫶OH; and $Z^1$=$CO_2CH_3$)

A. nor-C-Sta methyl ester hydrochloride

A solution of 0.15 g Boc-nor-C-Sta methyl ester in 4 mL of 4N HCl/dioxane was stirred at RF for 1 hour. The reaction was concentrated in vacuo to provide 0.15 g of a white solid. The material was used without further purification. NMR (300 MHz, DMSO-$d_6$) delta 3.65 (s, 3H), 4.17 (m, 1H), 6.47 (d, J=4 Hz, 1H).

B. morpholinocarbonylPheLeu methyl ester

To a solution of 0.30 g morpholinocarbonylPhe and 0.22 g HCl-LeuOMe in 5 mL anhydrous $CH_2Cl_2$ was added sequentially 0.12 g TEA, 0.18 g HBT and 0.24 g DCC. After stirring at RT 20 hours, the solution was filtered through Celite and was washed 2×10 mL 0.1N sodium hydroxide. The organic phase was dried over $MgSO_4$, filtered and concentrated in vacuo. The residue was chromatographed on $SiO_2$ (2:1 EtOAc:Hex) to provide 0.43 g pure product. NMR (300 MHz, $CDCl_3$) delta 0.89 (d, J=7 Hz, 6H), 3.71 (s, 3H), 4.48 (m, 1H), 4.57 (m, 1H), 6.25 (d, J=7 Hz, 1H).

C. morpholinocarbonylPheLeu

To a solution of 0.43 g morpholinocarbonylPheLeuOMe in 10 mL MeOH was added 0.1 g $K_2CO_3$, and the resulting solution was stirred at RT for 24 hours. The reaction mixture was concentrated in vacuo to a volume of 10 mL, and was acidified with 1N HCl and extracted 3×25 mL $CH_2Cl_2$. The combined extracts were dried over $MgSO_4$, filtered and concentrated to afford crude acid which was used without further purification. NMR (300 MHz, $CDCl_3$) delta 0.87 (2d, 6H), 4.45 (m, 1H), 4.65 (m, 1H), 5.36 (d, J=7 Hz, 1H).

D. morpholinocarbonylPheLeunor-C-Sta methyl ester

MorpholinocarbonylPheLeu (96 mg) was condensed with 80 mg nor-C-StaOMe-HCl using the DCC procedure described above. The crude product was chromatographed on $SiO_2$ (29:1 $CH_2Cl_2$:EtOH) to afford 68 mg pure product. NMR (300 MHz, $CDCl_3$) delta 0.85 (2d, 6H), 3.72 (s, 3H), 4.28 (m, 1H), 4.41 (m, 2H).

EXAMPLE 56

MorpholinocarbonylPheMetnor-C-Sta methyl ester (I, Z=morpholinocarbonylamino; M=phenyl; Q=H; $R_2=CH_3S(CH_2)_2-$; X=cyclohexyl; W=CH‖‖‖OH; and $Z^1=CO_2CH_3$)

A. morpholinocarbonylPheMet methyl ester

MorpholinocarbonylPhe (0.30 g) was coupled to 0.24 g HCl-methionineOMe using the DCC procedure in Example 55. The crude material was chromatographed on $SiO_2$ (2:1, EtOAc:Hex) to provide 0.36 g pure dipeptide. NMR (300 MHz, $CDCl_3$) delta 2.05 (s, 3H), 3.72 (s, 3H), 4.57 (m, 2H).

B. morpholinocarbonylPheMet

MorpholinocarbonylPheMet methyl ester (0.36 g) was saponified using the procedure in Example 55, affording 0.3 g crude acid which was used without further purification. NMR (300 MHz, $CDCl_3$) delta 2.01 (s, 3H), 2.44 (m, 1H), 4.61 (m, 1H).

C. morpholinocarbonylPheMetnor-C-Sta methyl ester

MorpholinocarbonylPheMet (0.10 g) was coupled to 0.080 g nor-C-StaOMe-HCl (Example 55) using DCC (Example 1). The crude product was chromatographed on $SiO_2$ (29:1, $CH_2Cl_2$:EtOH) to afford 50 mg pure product and 32 mg impure product. NMR (300 MHz, $CDCl_3$) delta 1.98 (s, 3H), 3.74 (s, 3H), 4.38 (m, 2H), 4.46 (m, 1H).

EXAMPLE 57

MorpholinocarbonylPhePhenor-C-Sta methyl ester (I, Z=morpholinocarbonylamino; M=phenyl; Q=H; $R_2$=benzyl; X=cyclohexyl; W=CH‖‖‖OH; and $Z^1=CO_2CH_3$)

A. morpholinocarbonylPhePhe methyl ester

MorpholinocarbonylPhe (0.30 g) was condensed with 0.26 g PheOMe-HCl using the DCC procedure described in Example 55. The crude dipeptide was chromatographed on $SiO_2$ (1:2 EtOAc:Hex) to afford 0.37 g pure product. NMR (300 MHz, $CDCl_3$) delta 3.65 (s, 3H), 4.49 (m, 1H), 4.78 (m, 1H).

B. morpholinocarbonylPhePhe

MorpholinocarbonylPhePhe methyl ester (0.37 g) was saponified as in Example 55 to afford 0.35 g crude acid which was used without further purification. NMR (300 MHz, $CDCl_3$) delta 4.59 (m, 1H), 4.65 (m, 1H), 5.10 (d, J=8 Hz, 1H).

C. morpholinocarbonylPhePhenor-C-Sta methyl ester

MorpholinocarbonylPhePhe (0.10 g) was condensed with 0.080 g nor-C-StaOMe-HCl using DCC as described in Example 55. The crude product was chromatographed on $SiO_2$ (29:1 $CH_2Cl_2$:EtOH) to afford 0.10 g pure compound. NMR (300 MHz, $CDCl_3$) delta 2.74 (s, 3H), 4.26 (m, 1H), 4.36 (m, 1H), 4.52 (m, 1H).

EXAMPLE 58

MorpholinocarbonylPhe S-MeCysnor-C-Sta methyl ester (I, Z=morpholinocarbonylamino; M=phenyl; Q=H; $R_2=CH_3SCH_2$; X=cyclohexyl; W=CH‖‖‖OH; and $Z^1=CO_2CH_3$)

A. morpholinocarbonylPhe S-MeCys methyl ester

MorpholinocarbonylPhe (0.96 g) and S-MeCysOMe-HCl (0.55 g) were coupled using the water soluble reagent DEC, along with TEA and HBT as in Example 55. The reaction mixture was diluted with 100 mL EtOAc, washed 2×35 mL 0.1N HCl and 2×35 mL 0.1N NaOH. The organic phase was dried over $MgSO_4$, filtered and concentrated in vacuo. The crude product (1.15 g) was pure enough to be carried through. NMR (300 MHz, $CDCl_3$) delta 2.00 (s, 3H), 3.72 (s, 3H), 4.58 (m, 1H), 4.65 (m, 1H).

B. morpholinocarbonylPhe S-MeCys

MorpholinocarbonylPhe S-MeCys methyl ester (1.15 g) was saponified as in Example 55, except the reaction was initially stirred at 0° for 15 minutes and then at RT. The crude product (1.0 g) was used without further purification. NMR (300 MHz, $CDCl_3$), delta 2.03 (s, 3H), 4.63 (m, 1H), 4.77 (m, 1H).

C. morpholinocarbonylPhe S-MeCysnor-Sta methyl ester

MorpholinocarbonylPhe S-MeCys (130 mg) was coupled to nor-C-StaOMe-HCl (69 mg) using the DCC procedure described in Example 55. The crude product was chromatographed on $SiO_2$ (19:1 $CH_2Cl_2$:EtOH) to afford 58 mg pure product. NMR (300 MHz, $CDCl_3$) delta 2.06 (s, 3H), 3.72 (s, 3H), 4.40 (m, 2H).

EXAMPLE 59

MorpholinocarbonylPhe S-EtCysnor-C-Sta methyl ester (I, Z=morpholinocarbonylamino; M=phenyl; Q=H; $R_2=CH_3CH_2SCH_2$—; X=cyclohexyl; W=CH‖‖‖OH; and $Z^1=CO_2CH_3$

A. morpholinocarbonylPhe S-EtCys methyl ester

MorpholinocarbonylPhe (0.20 g) was coupled to S-EtCysOMe-HCl (0.15 g) using DCC as described in Example 55. The crude compounds was chromatographed on $SiO_2$ (3:1 EtOAc:Hex) to afford 0.20 g pure product. NMR (300 MHz, $CDCl_3$) delta 2.16 (t, J=7 Hz, 3H), 2.45 (q, J=7 Hz, 2H), 3.73 (s, 3H), 4.64 (m, 2H).

B. morpholinocarbonylPhe S-EtCys

MorpholinocarbonylPhe S-EtCys methyl ester (0.20 g) was saponified as in Example 55 to afford 0.11 g crude acid which was used without further purification. NMR (300 MHz, $CDCl_3$) delta 2.16 (t, J=7 Hz, 3H), 2.50 (q, J=7 Hz, 2H), 4.64 (m, 1H), 4.79 (m, 1H).

C. morpholinocarbonylPhe S-EtCysnor-C-Sta methyl ester

MorpholinocarbonylPhe S-EtCys (0.11 g) was coupled to nor-C-StaOMe-HCl (75 mg) using the DCC procedure described in Example 55. The crude compounds was purified by chromatography on $SiO_2$ (29:1 $CH_2Cl_2$:EtOH) to afford 0.10 g pure product. NMR (300 MHz, $CDCl_3$) delta 2.21 (t, J=7 Hz, 3H), 2.50 (m, 2H), 3.75 (s, 3H), 4.40 (m, 2H).

EXAMPLE 60

MorpholinocarbonylPhe O-BSernor-C-Sta methyl ester (I, Z=morpholinocarbonylamino; M=phenyl; Q=H; $R_2=CH_2OCH_2C_6H_5$; X=cyclohexyl; W=CH ⁞⁞⁞⁞ OH; and $Z^1=CO_2CH_3$)

A. morpholinocarbonylPhe O-BSer methyl ester

MorpholinocarbonylPhe (0.31 g) was coupled to O-BSerOMe-HCl (0.25 g) using the standard DCC reaction described in Example 55. The crude compound was chromatographed on $SiO_2$ (1:3 EtOAc:Hex) to afford 0.28 g pure product. NMR (300 MHz, $CDCl_3$) delta 3.70 (s, 3H), 4.43 (m, 2H), 4.63 (m, 2H).

B. morpholinocarbonylPhe O-BSer

MorpholinocarbonylPhe O-BSer methyl ester (0.28 g) was saponified as described in Example 55. The crude acid (0.19 g) was used without further purification. NMR (300 MHz, $CDCl_3$) delta 4.40 (m, 2H), 4.63 (m, 1H), 4.72 (m, 1H).

C. morpholinocarbonylPhe O-BSernor-C-Sta methyl ester

MorpholinocarbonylPhe O-BSer (0.19 g) was coupled to nor-C-StaOMe-HCl (0.14 g) using the DCC procedure described in Example 55. The crude material was purified by chromatography on $SiO_2$ (29:1 $CH_2Cl_2$:EtOH) to afford 0.11 g pure product. NMR (300 MHz, $CDCl_3$) delta 3.73 (s, 3H), 4.40 (m, 2H), 4.45 (AB, 2H).

EXAMPLE 61

MorpholinocarbonylPhe O-BThrnor-C-Sta methyl ester (I, Z=morpholinocarbonylamino; M=phenyl; Q=H; $R_2=CH(CH_3)OCH_2C_6H_5$; X=cyclohexyl; W=CH ⁞⁞⁞⁞ OH; $Z^1=CH_3$)

A. morpholinocarbonylPhe O-BThr methyl ester

MorpholinocarbonylPhe (0.30 g) and OBThrOMe-HCl (0.35 g) were coupled using the standard DCC procedure (Example 55). The crude material (0.62 g) was used without further purification. NMR (300 MHz, $CDCl_3$) delta 1.13 (d, J=6 Hz, 3H), 3.63 (s, 3H), 4.38 (AB, 2H), 4.53 (m, 1H), 4.64 (m, 1H).

B. morpholinocarbonyl OBThr

MorpholinocarbonylPhe OBThr methyl ester (0.62 g) was saponified as described in Example 55, affording 0.41 g crude acid which was used without further purification. NMR (300 MHz, $CDCl_3$) delta 1.17 (d, J=6 Hz, 3H), 4.43 (AB, 2H), 4.62 (m, 1H), 4.70 (m, 1H).

C. morpholinocarbonylPhe OBThrnor-C-Sta methyl ester

MorpholinocarbonylPhe OBThr (99 mg) and nor-C-StaOMe-HCl (44 mg) were coupled using the standard DCC reaction (Example 55). The crude material was purified by chromatography (29:1 $CH_2Cl_2$:EtOH) to afford 97 mg pure product. NMR (300 MHz, $CDCl_3$) delta 1.16 (d, J=6 Hz, 3H), 3.76 (s, 3H), 4.30 (m, 1H), 4.41 (m, 1H), 4.46 (AB, 2H).

EXAMPLE 62

MorpholinocarbonylPheNvanor-C-Sta methyl ester (I, Z=morpholinocarbonylamino; M=phenyl; Q=H, $R_2$=n-propyl; X=cyclohexyl; W=CH ⁞⁞⁞⁞ OH; and $Z^1=CO_2CH_3$)

A. morpholinocarbonylPheNva methyl ester

MorpholinocarbonylPhe (0.20 g) and NvaOMe-HCl (0.10 g) was condensed using the DCC procedure described in Example 55. The crude material was chromatographed on $SiO_2$ (4:1 EtOAc:Hex) to afford 0.22 g pure product. NMR (300 MHz, $CDCl_3$) delta 0.92 (t, J=7 Hz, 3H), 3.65 (s, 3H), 4.42 (m, 1H), 4.54 (m, 1H).

B. morpholinocarbonylPheNva

MorpholinocarbonylPheNva methyl ester (0.22 g) was saponified by the standard procedure (Example 55), affording 0.17 g crude acid which was used without further purification. NMR (300 MHz, $CDCl_3$) delta 0.89 (t, J=7 Hz, 3H), 4.46 (m, 1H), 4.62 (m, 1H).

C. morpholinocarbonylPheNvanor-C-Sta methyl ester

MorpholinocarbonylPheNva (0.10 g) and nor-C-StaOme-HCl (0.075 g) were coupled using DCC as described in Example 55. The crude product was purified by chromatography (29:1 $CH_2Cl_2$:EtOH) to afford 0.12 g pure product. NMR (300 MHz, $CDCl_3$) delta 0.97 (t, J=7 Hz, 3H), 3.72 (m, 3H), 4.29 (m, 1H), 4.40 (m, 1H), 4.53 (m, 1H).

EXAMPLE 63

MorpholinocarbonylPheNlenor-C-Sta n-propylamide (I, Z=morpholinocarbonylamino; M=phenyl; Q=H, $R_2$=n-butyl; X=cyclohexyl; W=CH ⁞⁞⁞⁞ OH; and $Z^1=CONH(CH_2)_2CH_3$)

A. Boc nor-C-Sta n-propylamide

To a solution of 100 mg Boc-nor-C-Sta and 21 mg n-propylamine in 5 mL dry $CH_2Cl_2$ was added 54 mg HBT and 70 mg DEC, and the resulting solution was stirred at RT for 20 hours. The solution was diluted with 200 mL EtOAc, and washed 2×20 mL $H_2O$, 2×20 mL 0.1N HCl, 2×20 mL 0.1N NaOH. The organic phase was dried over $MgSO_4$, filtered and concentrated in vacuo to 142 mg crude amide which was used without further purification. NMR (300 MHz, $CDCl_3$) delta 0.91 (t, J=7 Hz, 3H), 1.40 (s, 9H), 3.85 (m, 1H), 4.04 (d, J=3 Hz, 1H).

B. nor-C-Sta n-propylamide hydrochloride

A mixture of 139 mg Boc-nor-C-StaNHnPr in 3 mL 4N HCl in dioxane was stirred at RT for 3 hours. The solution was concentrated in vacuo to afford 96 mg crude product which was used without further purification. NMR (300 MHz, DMSO-$d_6$) delta 0.85 (t, J=7 Hz, 3H), 3.06 (m, 2H), 4.03 (d, J=3 Hz, 1H).

C. morpholinocarbonylPheNlenor-C-Sta n-propyl amide

MorpholinocarbonylPheNle (135 mg) was coupled to HCl-nor-C-StaNHnPr (96 mg) using the DEC procedure described in Example 58. The crude product was chromatographed on $SiO_2$ (9:1 $CH_2Cl_2$:MeOH) to afford 113 mg pure product. NMR (300 MHz, $CDCl_3$) delta 0.90 (t, J=7 Hz, 3H), 4.08 (d, J=7 Hz, 1H), 4.32 (m, 2H), 4.80 (m, 1H).

EXAMPLE 64

MorpholinocarbonylPheNle nor-C-Sta i-propylamide
(I, Z=morpholinocarbonylamino; M=phenyl; Q=H;
R$_2$=n-butyl; X=cyclohexyl; W=CH⫼OH;
Z$^1$=CONHCH(CH$_3$)$_2$)

A. Boc nor-C-Sta i-propyl amide

Isopropylamine (29 mg) was coupled to Boc-nor-CSta (100 mg) using the DCC procedure described in Example 55. The crude material was chromatographed on SiO$_2$ (9:1 CH$_2$Cl$_2$) to afford 73 mg pure amide. NMR (300 MHz, CDCl$_3$) delta 1.11 (d, J=5 Hz, 3H), 1.12 (d, J=5 Hz, 3H), 1.37 (s, 9H), 3.82 (m, 1H), 3.97 (m, 1H), 4.03 (m, 1H).

B. nor-C-Sta i-propylamide hydrochloride

Boc-nor-C-StaNHiPr (62 mg) was deprotected by stirring in 2 mL 4N HCl-dioxane for 3 hours. The solution was concentrated in vacuo to 52 mg of a white solid. The crude HCl salt was used without further purification. NMR (300 MHz, DMSO-d$_6$) delta 1.10 (m, 6H), 3.92 (m, 1H), 3.98 (m, 1H).

C. morpholinocarbonylPheNlenor-C-Sta i-propyl amide

MorpholinocarbonylPheNle (48 mg) was coupled to HCl-nor-C-Sta NHiPr (48 mg) using the DCC procedure described in Example 55. The crude material was chromatographed on SiO$_2$ (19:1 CH$_2$Cl$_2$:MeOH) to afford 60 mg pure product NMR (300 MHz, CDCl$_3$) delta 1.09 (d, J=6 Hz, 6H), 4.00 (m, 1H), 4.03 (m, 3H), 4.33 (m, 2H).

EXAMPLE 65

MorpholinocarbonylPheNlenor-C-Sta i-butylamide (I,
Z=morpholinocarbonylamino; M=phenyl; Q=H;
R$_2$=n-butyl; X=cyclohexyl; W=CH⫼OH;
Z=CONHCH$_2$CH(CH$_3$)$_2$)

A. Boc nor-C-Sta i-butylamide

Isobutylamine (49 L) was coupled to Boc-nor-C-StaNHiBu (100 mg) using the DCC procedure described in Example 55. the crude material was purified by chromatography (9:1 CH$_2$Cl$_2$:MeOH) to afford 75 mg pure product. NMR (300 MHz, CDCl$_3$) delta 0.89 (d, J=6 Hz, 6H), 1.39 (s, 9H), 3.83 (m, 1H), 4.03 (m, 1H).

B. nor-C-Sta i-butylamide hydrochloride

Boc-nor-C-StaNHiBu (173 mg) was deprotected as in Example 64 to afford 170 mg crude salt which was used without further purification. NMR (300 MHz, DMSO-d$_6$) delta 0.85 (d, J=6 Hz, 6H), 2.93 (m, 2H), 4.03 (m, 1H).

C. morpholinocarbonylPheNlenor-C-Sta i-butylamide

MorpholinocarbonylPheNle (235 mg) was coupled to HCl-nor-C-StaNHiBu (160 mg) using the DCC procedure (Example 55). The crude product was purified by chromatography (9:1 CH$_2$Cl$_2$:MeOH) to afford 152 mg pure product. NMR (300 MHz, CDCl$_3$) delta 0.87 (d, J=6 Hz, 6H), 4.08 (d, J=3 Hz, 1H), 4.32 (m, 2H).

EXAMPLE 66

MorpholinocarbonylPheNlenor-C-Sta
N-methyl-N-i-propylamide (I,
Z=morpholinocarbonylamino; M=phenyl; Q=H;
R$_2$=n-butyl; X=cyclohexyl; W=CH⫼OH; and
Z$^1$=CON(CH$_3$)CH(CH$_3$)$_2$)

A. Boc nor-C-Sta N-methy1N-i-propylamide

N-methyl-N-isopropylamine (44 mg) was coupled to Boc-nor-C-Sta (120 mg) using the DCC procedure (Example 55). The crude product was chromatographed (39:1 CH$_2$Cl$_2$:MeOH) to afford 56 mg pure product. NMR (300 MHz, CDCl$_3$) delta 1.40 (s, 9H), 2.89 (s, 3H), 4.74 (m, 1H).

B. nor-C-Sta N-methyl-N-i-propylamide hydrochloride

Boc-nor-C-StaN(Me)iPr (56 mg) was deprotected as in Example 64 to afford 52 mg crude salt which was used without further purification. NMR (300 MHz, DMSO-d$_6$) delta (3.00 (s, 3H), 4.30 (s, 1H).

C. morpholinocarbonylPheNlenor-C-Sta N-methyl-N-i-propylamide

MorpholinocarbonylPheNle (73 mg) was coupled to HCl-nor-C-Sta(Me)iPr (52 mg) using the DCC procedure described in Example 55. The crude material was purified by chromatography (19:1 CH$_2$Cl$_2$:MeOH) to afford 99 mg pure product. NMR (300 MHz, CDCl$_3$) delta 2.84 (s, 3H), 4.12 (m, 1H), 4.40 (m, 1H), 4.53 (m, 1H).

EXAMPLE 67

MorpholinocarbonylPheNlenor-C-Sta
N-methyl-N-ibutylamide (I,
Z=morpholinocarbonylamino; M=phenyl; Q=H;
R$_2$=n-butyl; X=cyclohexyl; W=CH⫼OH;
Z$^1$=CON(CH$_3$)CH$_2$CH(CH$_3$)$_2$)

A. Boc nor-C-Sta N-methyl N-i-butylamide

N-Methyl-N-isobutylamine (56 mg) was coupled to Boc-nor-C-Sta (128 mg) using the DCC procedure described in Example 55. The crude material was chromatographed (9:1 CH$_2$Cl$_2$:MeOH) to afford 130 mg pure product. NMR (300 MHz, CDCl$_3$) delta 1.38 (s, 9H), 3.03 (s, 3H), 4.28 (m, 1H).

B. nor-C-Sta N-methyl-N-i-butyl amide hydrochloride

Boc-nor-C-StaN(Me)iBu (123 mg) was deprotected as described in Example 55 to afford 118 mg crude salt which was used without further purification. NMR (300 MHz, DMSO-d$_6$) delta 3.67 (s, 3H), 4.54 (m, 1H), 4.61 (m, 1H).

C. morpholinocarbonylPheNlenor-C-Sta N-methyl-N-i-butyl amide

MorpholinocarbonylPheNle (173 mg) was coupled to HCl-nor-C-StaN(Me)iBu (118 mg) using the DCC procedure described in Example 55. The crude material was chromatographed (19:1 CH$_2$Cl$_2$:MeOH) to afford 184 mg pure material. NMR (300 MHz, CDCl$_3$) delta 3.04 (s, 3H), 4.18 (m, 1H), 4.36 (m, 1H), 4.43 (m, 1H), 4.57 (m, 1H).

EXAMPLE 68

MorpholinocarbonylPheNlenor-C-Sta n-pentyl amide
(I, Z=morpholinocarbonylamino; M=phenyl; Q=H; $R_2$=n-butyl; X=cyclohexyl; W=CH⫶⫶OH; and $Z^1$=CONH(CH$_2$)$_4$CH$_3$)

A. Boc-nor-C-Sta n-pentyl amide

N-Pentylamine (29 mg) was coupled to Boc-nor-C-Sta (100 mg) using the DEC procedure described in Example 63. The crude material (128 mg) was used without further purification. NMR (300 MHz, CDCl$_3$) delta 1.41 (s, 9H), 3.25 (m, 2H), 3.86 (m, 1H), 4.05 (m, 1H).

B. nor-C-Sta n-pentyl amide hydrochloride

Boc-nor-C-StaNHnPn (128 mg) was deprotected as in Example 63 to afford 108 mg crude salt which was used without further purification. NMR (300 MHz, DMSO-d$_6$) delta 3.09 (m, 2H), 4.00 (d, J=4 Hz, 1H).

C. morpholinocarbonylPheNlenor-C-Sta n-pentyl amide

MorpholinocarbonylPheNle (138 mg) was coupled to HCl-nor-C-StaNHnPn (108 mg) using the DEC procedure described in Example 58. The crude material was chromatographed (19:1 CH$_2$Cl$_2$:MeOH) to afford 140 mg pure product. NMR (300 MHz, CDCl$_3$) delta 4.08 (m, 1H), 4.32 (m, 2H), 4.74 (m, 1H).

EXAMPLE 69

MorpholinocarbonylPheNlenor-C-Sta N,N-bisethyleneoxy amide (I, Z=morpholinocarbonylamino; M=phenyl; Q=H; $R_2$=n-butyl; X=cyclohexyl; W=CH⫶⫶OH; and $Z^1$=CON(CH$_2$CH$_2$)$_2$O)

A. Boc-nor-Sta N,N-bisethyleneoxy amide

Morpholine (43 mg) was coupled to Boc-nor-C-Sta (100 mg) using the standard DCC procedure (Example 55). The crude material was chromatographed (4:1 EtOAc:Hex) to afford 134 mg pure product. NMR (300 MHz, CDCl$_3$) delta 1.36 (s, 9H), 4.06 (d, J-5 Hz, 1H), 4.22 (br, 1H).

B. nor-C-Sta N,N-bisethyleneoxy amide hydrochloride

Boc-nor-C-StaMr (122 mg) was deprotected by the standard procedure (Example 63) to afford 125 mg crude salt which was used without further purification. NMR (300 MHz, DMSO-d$_6$) delta 4.34 (d, J=5 Hz, 1H).

C. morpholinocarbonylPheNlenor-C-Sta N,N-bisethyleneoxy amide

MorpholinocarbonylPheNle (142 mg) was coupled to HCl-nor-C-StaMr (101 mg) using the standard DCC procedure (Example 55). The crude material was purified by chromatography (19:1 CH$_2$Cl$_2$:EtOH) to afford 72 mg pure product. NMR (300 MHz, CDCl$_3$) delta 4.16 (m, 1H), 4.25 (br, 1H), 4.42 (m, 1H), 4.48 (m, 1H), 4.97 (m, 1H).

EXAMPLE 70

MorpholinoPheNlenor-C-Sta N,N-bisethylene-N'-methylaza amide (I, Z=morpholinocarbonylamino; M=phenyl; Q=H; $R_2$=n-butyl; X=cyclohexyl; W=CH⫶⫶OH; and $Z^1$=CON(CH$_2$CH$_2$)$_2$N-CH$_3$)

A. Bocnor-C-Sta N,N-bisethylene-N'-methylaza amide

1-Methylpiperazine (50 mg was coupled to Boc-nor-C-Sta (100 mg) using the standard DCC reaction (Example 55). The crude material was chromatographed (9:1 CH$_2$Cl$_2$:EtOH) to afford 118 mg pure product. NMR (300 MHz, CDCl$_3$) delta 1.36 (s, 9H), 2.30 (s, 3H), 3.96 (m, 1H), 4.24 (s, 1H).

B. nor-C-Sta N,N-bisethylene-N'-methylaza amide hydrochloride

Boc-nor-C-StaMePip (118 mg) was deprotected using the standard conditions (Example 63) to afford 113 mg crude salt which was used without further purification. NMR (300 MHz, CDCl$_3$) delta 3.48 (s, 3H), 4.22 (m, 1H), 4.39 (m, 2H).

C. morpholinocarbonylPheNlenor-C-Sta N,N-bisethylene-N'-methylaza amide

MorpholinocarbonylPheNle (133 mg) was coupled to HCl-nor-C-StaMePip (105 mg) using the standard DCC reaction (Example 55). The crude material was chromatographed (9:1 CH$_2$Cl$_2$:EtOH) to afford 110 mg pure product. NMR (300 MHz, CDCl$_3$) delta 2.33 (s, 3H), 4.17 (m, 1H), 4.31 (m, 2H), 4.52 (m, 1H).

EXAMPLE 71

MorpholinocarbonylPheNlenor-C-Sta i-propyl ester (I, Z=morpholinocarbonylamino; M=phenyl; Q=H; $R_2$=n-butyl; X=cyclohexyl; W=CH⫶⫶OH; and $Z^1$=CO$_2$CH(CH$_3$)$_2$)

A. nor-C-Sta i-propyl ester hydrochloride

A solution of 100 mg Boc-nor-C-Sta in 2 ml anhydrous isopropanol was saturated with anhydrous HCl and the resulting solution was stirred at RT overnight. The reaction mixture was concentrated in vacuo to afford 98 mg crude salt which was used without further purification. NMR (300 MHz, DMSO-d$_6$) delta 1.20 (d, J=6 Hz, 6H), 3.28 (m, 1H), 4.05 (d, J=5 Hz, 1H), 4.92 (m, 1H).

B. morpholinocarbonylPheNlenor-C-Sta i-propyl ester

MorpholinocarbonylPheNle (142 mg) was coupled to HCl-nor-C-StaOiPr (92 mg) using the standard DCC reaction (Example 55). The crude material was chromatographed (9:1 CH$_2$Cl$_2$:EtOH) to afford 60 mg pure product. NMR (300 MHz, CDCl$_3$) delta 1.24 (d, J=7 Hz, 6H), 4.06 (br, 1H), 4.19 (m, 1H), 4.43 (m, 2H), 5.00 (m, 1H).

EXAMPLE 72

MorpholinocarbonylPheO-MeSernor-C-Sta i-propyl ester (I, Z=morpholinocarbonylamino; M=phenyl; Q=H; $R_2$=CH$_3$OCH$_2$—; X=cyclohexyl; W=CH⫶⫶OH; $Z^1$=CO$_2$CH(CH$_3$)$_2$)

A. morpholinocarbonylPheOMeSer methyl ester

MorpholinocarbonylPhe (0.5 g) was coupled to DL-O-methylserineOMe (0.34 g) using the standard DEC reaction described in Example 58. The crude material (0.37 g) was used without further purification. NMR (one isomer) (300 MHz, CDCl$_3$) delta 3.24 (s, 3H), 3.76 (s, 3H), 4.65 (m, 1H).

B. morpholinocarbonylPheO-MeSer

MorpholinocarbonylPheOMSerOMe (0.37 g) was saponified as described in Example 55 to afford 0.16 g crude acid which was used without further purification. NMR (one isomer) (300 MHz, CDCl$_3$) delta 3.18 (s, 3H), 4.58 (m, 1H), 4.73 (m, 1H).

C. morpholinocarbonylPheO-MeSernor-C-Sta i-propyl ester

MorpholinocarbonylPheOMeSer (0.15 g) was coupled to HCl-nor-C-StaOiPr (0.10 g) using the standard DEC reaction (Example 58). The crude material was chromatographed (29:1 CH$_2$Cl$_2$:EtOH) to afford 43 mg pure product and 36 mg serine epimer. NMR (major isomer) (300 MHz, CDCl$_3$) delta 3.14 (s, 3H), 4.13 (m, 2H), 4.45 (m, 2H), 4.96 (m, 2H).

EXAMPLE 73

MorpholinocarbonylPheO-EtSernor-C-Sta i-propyl ester (I, Z=morpholinocarbonylamino; M=phenyl; Q=H; R$_2$=CH$_3$CH$_2$—; X=cyclohexyl; W=CH⫶⫶⫶OH; and Z$^1$=CO$_2$CH(CH$_3$)$_2$)

A. BocO-EtSer

To a solution of 0.94 g BocSer in 66 mL THF was added a solution of 1.47 g NaOMe in 2.6 mL MeOH, followed by 11.7 g EtI. After 15 minutes, more NaOMe (0.49 g) and EtI (2 mL) were added and the reaction was stirred at RT overnight. More NaOMe and EtI were added and the reaction was stirred for an additional 6 hours. The mixture was concentrated in vacuo, dissolved in 25 mL H$_2$O and washed 2×25 mL ether. The aqueous phase was acidified with concentrated HCl and extracted 4×25 mL CH$_2$Cl$_2$. The combined extracts were dried over MgSO$_4$, filtered and concentrated in vacuo to 0.34 g crude product which carried on. NMR (300 MHz, CDCl$_3$), delta 1.19 (t, J=7 Hz, 3H), 1.46 (s, 9H), 3.53 (q, J=7 Hz, 2H), 4.43 (m, 1H).

B. O-EtSer methyl ester hydrochloride

A solution of 0.51 g BocOEtSer in 25 mL anhydrous MeOH was saturated with anhydrous HCl and stirred at RT for 18 hours. The solution was concentrated in vacuo and the solid residue was recrystallized (EtOH/ether) to afford 0.31 g pure salt. NMR (300 MHz, DMSO-d$_6$) delta 1.10 (t, J=8 Hz, 3H), 3.48 (m, 2H), 3.75 (s, 3H), 4.28 (m, 1H).

C. morpholinocarbonylO-EtSer methyl ester

MorpholinocarbonylPhe (0.36 g) was coupled to HCl-OEtSerOMe (0.25 g) using the standard DEC reaction (Example 58). The crude material was chromatographed (19:1 CH$_2$Cl$_2$:EtOH) to afford 0.22 g pure product. NMR (300 MHz, CDCl$_3$) delta 1.10 (t, J=7 Hz, 3H), 3.41 (q, J=7 Hz, 2H), 3.73 (s, 3H), 4.62 (m, 2H).

D. morpholinocarbonylPheO-EtSer

MorpholinocarbonylPheOEtSerOMe (0.22 g) was saponified as described in Example 55 to afford 0.15 g crude acid which was used without further purification. NMR (300 MHz, CDCl$_3$) delta 1.12 (2t, 3H), 4.62 (m, 1H), 4.72 (m, 1H).

E. morpholinocarbonylPheO-EtSernor-C-Sta i-propyl ester

MorpholinocarbonylPheOEtSer (75 mg) was coupled to HCl-nor-C-StaOiPr (54 mg) using the standard DEC reaction (Example 58). The crude material was chromatographed (19:1 CH$_2$Cl$_2$:EtOH) to afford 50 mg pure product. NMR (300 MHz, CDCl$_3$) delta 1.12 (t, J=7 Hz, 3H), 3.44 (q, J=7 Hz, 2H), 4.30 (m, 1H), 4.43 (m, 2H), 5.04 (m, 1H).

EXAMPLE 74

MorpholinocarbonylPhetetamethyleneGlynor-C-Sta i-propyl ester (I, Z=morpholinocarbonylamino; M=phenyl; Q=H; R$_2$=—(CH$_2$)$_4$—; X=cyclohexyl; W=CH⫶⫶⫶OH; Z$^1$=CO$_2$CH(CH$_3$)$_2$)

A. tetramethyleneglycine methyl ester hydrochloride

A solution of 2.5 g alpha-tetramethyleneGly in 30 mL MeOH was saturated with anhydrous HCl and stirred at RT for 60 hours. The solution was concentrated in vacuo and the residue was recrystallized from ether/ethanol to afford 2.4 g pure product. NMR (300 MHz, DMSO-d$_6$) delta 3.77 (s, 3H).

B. morpholinocarbonylPheTMGly methyl ester

MorpholinocarbonylPhe (0.50 g) was coupled to HCl-TMGlyOMe (0.36 g) using the standard DEC reaction (Example 58). The crude material (0.48 g) was used without further purification. NMR (300 MHz, CDCl$_3$) delta 3.67 (s, 3H), 4.57 (m, 2H), 5.51 (d, J=6 Hz, 1H).

C. morpholinocarbonylPheTMGly

MorpholinocarbonylPheTMGlyOMe (0.48 g) was saponified as described in Example 55 to afford 0.43 g crude acid which was carried on without further purification. NMR (300 MHz, DMSO-d$_6$) delta 4.39 (m, 2H), 6.55 (d, J=8 Hz, 1H).

D. morpholinocarbonylPheTMGlynor-C-Sta i-propyl ester

MorpholinocarbonylPheTMGly (0.11 g) was coupled to HCl-nor-C-StaOiPr (0.10 g) using the standard DEC reaction described in Example 58. The crude material was chromatographed (3:1 EtOAc:Hex) to afford 70 mg pure product. NMR (300 MHz, CDCl$_3$) delta 4.21 (m, 1H), 4.47 (m, 1H), 4.98 (m, 2H).

EXAMPLE 75

MorpholinocarbonylPhePGlynor-C-Sta i-propyl ester (I, Z=morpholinocarbonylamino; M=phenyl; Q=H; R$_2$=CH$_3$(CH$_2$)$_4$—; X=cyclohexyl; W=CH⫶⫶⫶OH; and Z$^1$=CO$_2$CH(CH$_3$)$_2$)

A. PGly ethyl ester

A solution of 10 g GlyOEt-benzophenone imine, 8 g iodopentane and 14 g nBu$_4$NH-HSO$_4$ in 150 mL CH$_2$Cl$_2$ and 3 mL 10% NaOH was stirred at RT for 16 hours. The organic phase was separated, dried over MgSO$_4$, filtered and concentrated in vacuo. The residue was dissolved in 50 mL THF and 50 mL 0.1N HCl and stirred at RT for 4 hours. The mixture was concentrated to an aqueous solution and washed 3×50 mL ether. The aqueous phase was made basic and extracted 3×50 mL CH$_2$Cl$_2$. The combined extracts were dried over MgSO$_4$, filtered and concentrated. The residue was chromatographed (1:1 EtOAc:hex) to afford 0.51 g pure product. The corresponding HCl salt was prepared by treating the above amine with anhydrous HCl in ether. NMR (300 MHz, DMSO-d$_6$) delta 1.05 (t, J=7 Hz, 3H), 1.77 (m, 2H), 3.97 (m, 1H), 4.20 (m, 2H).

B. morpholinocarbonylPhePGly ethyl ester

MorpholinocarbonylPhe (0.40 g) was coupled to HCl-PGlyOEt (0.33 g) using the standard DEC reaction (Example 58). The crude material was chromatographed (1:3 EtOAc:Hex) to afford 0.40 g of product as a mixture of diastereomers at the PGly. NMR (300 MHz, CDCl$_3$) delta 4.13 (m, 2H), 4.42 (m, 1H), 4.57 (m, 1H).

C. morpholinocarbonylPhePGly

MorpholinocarbonylPhePGlyOEt was saponified as described in Example 55 to afford 0.33 g crude acid which was used without further purification. NMR (300 MHz, CDCl$_3$) delta 4.43 (m, 2H), 4.72 (m, 1H), 4.93 (m, 1H).

D. morpholinocarbonylPhePGlynor-C-Sta i-propyl ester

MorpholinocarbonylPhePGly (0.16 g) was coupled to HCl-nor-C-StaOiPr (0.10 g) using the standard DEC reaction (Example 58). The crude material was chromatographed (1:1 EtOAc:Hex) to afford 0.11 g of the desired L-product and 0.078 g of the D-isomer. NMR (major isomer) (300 MHz, CDCl$_3$) delta 2.27 (d, J=7 Hz, 6H), 4.25 (m, 1H), 4.46 (m, 1H), 4.53 (m, 1H), 5.03 (m, 2H).

EXAMPLE 76

MorpholinocarbonylPheO-MeHSenor-C-Sta i-propyl ester (I, Z=morpholinocarbonylamino; M=phenyl; Q=H; R$_2$=CH$_3$O(CH$_2$)$_2$—; X=cyclohexyl; W=CH ||||||||OH; and Z$^1$=CO$_2$CH(CH$_3$)$_2$)

A. Boc O-methylhomoserine

Boc-homoserine (0.51 g) was methylated as described for Boc-serine in Example 73. This afforded 0.45 g crude product which was carried on without further purification. NMR (300 MHz, CDCl$_3$) delta 1.40 (s, 9H), 3.16 (s, 3H), 3.90 (m, 2H).

B. BocO-MeHSenor-C-Sta i-propyl ester

BocOMHse (0.45 g) was coupled to nor-C-StaOiPr (0.5 g) using the DEC procedure described in Example 58 except that no TEA was used. The crude material was chromatographed (1:1 EtOAc:Hex) to afford 0.52 g pure product. NMR (300 MHz, CDCl$_3$) delta 1.21 (d, J=7 Hz, 6H), 1.38 (s, 9H), 3.27 (s, 3H), 4.19 (m, 1H), 4.38 (m, 1H), 4.96 (m, 1H).

C. O-MeHSenor-C-Sta i-propyl ester

BocOMeHse-nor-C-StaOiPr (0.52 g) was deprotected using the standard HCl/dioxane conditions described in Example 63. This afforded 0.66 g crude product which was used without further purification. NMR (300 MHz, DMSO-d$_6$) delta 1.18 (d, J=7 Hz, 6H), 3.24 (s, 3H), 4.18 (m, 1H), 4.80 (m, 1H).

D. morpholinocarbonylPheO-MeHSenor-C-Sta i-propyl ester

MorpholinocarbonylPhe (0.19 g) was coupled to HCl-OMeHse-nor-C-StaOiPr (0.20 g) using the standard DEC procedure described in Example 58. The crude material was chromatographed (29:1 CH$_2$Cl$_2$:MeOH) to afford 0.31 g pure product. NMR (300 MHz, CDCl$_3$) delta 1.23 (d, J=7 Hz, 3H), 1.25 (d, J=7 Hz, 3H), 3.19 (s, 3H), 4.29 (m, 1H), 4.42 (m, 2H), 5.04 (m, 1H).

EXAMPLE 77

MorpholinocarbonylPheHsenor-C-Sta i-propyl ester (I, Z=morpholinocarbonylamino; M=phenyl; Q=H; R$_2$=HO(CH$_2$)$_2$—; X=cyclohexyl; W=CH||||||||OH; and Z$^1$=CO$_2$CH(CH$_3$)$_2$)

A. BocO-benzylhomoserine

BocHse (0.51 g) was benzylated as described for Ser in Example 73. This afforded 0.42 g crude product which was used without further purification. NMR (300 MHz, CDCl$_3$) delta 1.38 (s, 9H), 4.10 (m, 1H), 4.45 (AB, 2H).

B. BocO-benzylhomoserinenor-C-Sta i-propyl ester

BocO-benzylHse (0.40 g) was coupled to nor-C-StaOiPr (0.50 g) using the DEC reaction described in Example 76. The crude product was chromatographed (1:1 EtOAc:Hex) to afford 0.53 g pure product. NMR (300 MHz, CDCl$_3$) delta 1.22 (d, J=7 Hz, 6H), 1.40 (s, 9H), 4.10 (m, 1H), 4.40 (m, 1H), 4.45 (m, 2H), 4.96 (m, 1H).

C. O-benzylhomoserinenor-C-Sta i-propyl ester hydrochloride

BocO-benzylHse-nor-C-StaOiPr (0.53 g) was deprotected as described in Example 76 to afford 0.54 g crude salt which was used without further purification. NMR (300 MHz, DMSO-d$_6$) delta 1.17 (d, J=7 Hz, 3H), 1.18 (d, J=Hz, 3H), 4.21 (m, 1H), 4.47 (m, 2H), 4.80 (m, 1H).

D. morpholinocarbonylPheO-benzylhomoserinenor-C-Sta i-propyl ester

MorpholinocarbonylPhe (0.53 g) was coupled to HCl-O-benzylHse-nor-C-StaOiPr (0.54 g) using the DEC reaction described in Example 76. The crude material was chromatographed (19:1 CH$_2$Cl$_2$:MeOH) to afford 0.40 g pure product. NMR (300 MHz, CDCl$_3$) delta 1.24 (d, J=7 Hz, 3H), 1.27 (d, J=7 Hz, 3H), 4.28 (m, 1H), 4.39 (AB, 2H), 4.48 (m, 2H), 5.04 (m, 1H).

E. morpholinocarbonylPheHsenor-C-Sta i-propyl ester

A mixture of 0.39 g morpholinocarbonylPheO-benzylHse-nor-C-StaOiPr and 1.0 g 10% Pd/C in 40 mL MeOH was hydrogenated at 50 p.s.i. for 7 hours. The mixture was filtered and concentrated in vacuo and the residue was chromatographed (19:1 CH$_2$Cl$_2$:MeOH) to afford 91 mg pure product along with some unreacted starting material. NMR (300 MHz, DMSO-d$_6$) delta 1.17 (d, J=7 Hz, 3H), 1.19 (d, J=7 Hz, 3H), 4.29 (m, 2H), 4.47 (m, 1H), 4.83 (m, 1H).

EXAMPLE 78

MorpholinocarbonylPheS-MeCys-oxidenor-C-Sta i-propyl ester (I, Z=morpholinocarbonylamino; M=phenyl; Q=H; R$_2$=CH$_3$SOCH$_2$—; X=cyclohexyl; W=CH||||||||OH; and Z$^1$=CO$_2$CH(CH$_3$)$_2$)

A solution of 84 mg morpholinocarbonylPheSMe-Cys-nor-C-StaOiPr (Example 17) and 24 mg m-CPBA in 10 mL CH$_2$Cl$_2$ was stirred at 0° C. for 30 minutes. The solution was diluted with 30 mL EtOAc and was washed 2×15 mL 10% Na$_2$SO$_3$ and 1×15 mL 0.1N NaOH. The organic phase was dried over MgSO$_4$, filtered and concentrated in vacuo and the residue was chromatographed (17:3 CH$_2$Cl$_2$:EtOH) to afford 40 mg pure product. NMR (300 MHz, CDCl$_3$) delta 1.29 (d, J=7 Hz, 6H), 2.78 (s, 3H), 4.37 (m, 1H), 4.44 (m, 1H), 4.77 (m, 1H), 5.00 (m, 1H).

EXAMPLE 79

MorpholinocarbonylPheS-MeCysdioxidenor-C-Sta i-propyl ester (I, Z=morpholinocarbonylamino; M=phenyl; Q=H; R$_2$=CH$_3$SO$_2$CH$_2$—; X=cyclohexyl; W=CH⦀OH; and Z=CO$_2$CH(CH$_3$)$_2$)

A solution of 20 mg morpholinocarbonylPheSMe-Cys-nor-C-StaOiPr (Example 17) and 16 mg m-CPBA in 3 mL CH$_2$Cl$_2$ was stirred 0° for 30 minutes. The reaction was worked up as in Example 78 and the residue was chromatographed (19:1 CH$_2$Cl$_2$:EtOH) to afford 13 mg pure product. NMR (300 MHz, CDCl$_3$) delta 1.28 (d, J=7 Hz, 3H), 1.30 (d, J=7 Hz, 3H), 3.00 (s, 3H), 4.26 (m, 1H), 4.45 (m, 1H), 4.85 (m, IH), 5.06 (m, 1H).

EXAMPLE 80

MorpholinocarbonylPheSernor-C-Sta i-propyl ester (I, Z=morpholinocarbonylamino; M=phenyl; Q=H; R$_2$=HOCH$_2$—; X=cyclohexyl; W=CH⦀OH; and Z$^1$=CO$_2$CH(CH$_3$)$_2$)

A. morpholinocarbonylPheO-Succinimide

To a solution of 25 g morpholinocarbonylPhe and 15.5 g N-hydroxysuccinimide in 800 mL CH$_2$Cl$_2$ was added 19 g DEC. After stirring for 20 hours at RT, the solution was washed 2×200 mL saturated NaHCO$_3$, dried over MgSO$_4$, filtered and concentrated in vacuo. This afforded 29 g crude product as a white solid. NMR (300 MHz, CDCl$_3$) delta 2.78 (m, 4H), 4.81 (d, J=8 Hz, 1H), 5.09 (m, 1H).

B. morpholinocarbonylPheSer

A solution of 0.50 g morpholinocarbonylPheOSuc in 5 mL THF was added to a solution of 0.30 g Ser in 10 mL saturated NaHCO$_3$, and the resulting mixture was stirred for 15 minutes. The reaction was diluted with 30 mL 0.1N NaOH and was washed 3×40 mL CH$_2$Cl$_2$. The aqueous phase was acidified with concentrated HCl and was extracted 6×75 mL EtOAc. The combined extracts were dried over MgSO$_4$, filtered and concentrated to afford 0.40 g crude product which was used without further purification. NMR (300 MHz, CDCl$_3$) delta 3.66 (m, 2H), 4.25 (m, 1H), 4.37 (m, 1H).

C. morpholinocarbonylPheSernor-C-Sta i-propyl ester

MorpholinocarbonylPheSer (0.39 g) was coupled to nor-C-StaOiPr (0.33 g) using the DEC procedure described in Example 76. The crude material was chromatographed (24:1 CH$_2$Cl$_2$:EtOH) to afford 0.23 g pure product. NMR (300 MHz, CDCl$_3$) delta 1.13 (d, J=7 Hz, 3H), 1.15 (d, J=7 Hz, 3H), 3.94 (m, 1H), 4.20 (m, H), 4.30 (m, 1H), 4.88 (m, 1H), 4.80 (m, 1H).

EXAMPLE 81

MorpholinocarbonylPheAlanor-C-Sta i-propyl ester (I, Z=morpholinocarbonylamino; M=phenyl; Q=H; R$_2$=CH$_3$; X=cyclohexyl; W=CH⦀OH; and Z$^1$=CO$_2$CH(CH$_3$)$_2$)

A. morpholinocarbonylPheAla

Alanine (0.24 g) and morpholinocarbonylPheOSuc (0.50 g) were allowed to react as described in Example 80 to afford 0.15 g crude product which was used without further purification. NMR (300 MHz, DMSO-d$_6$) delta 1.31 (d, J=7 Hz, 3H), 4.20 (m, 1H), 4.32 (m, 1H).

B. morpholinocarbonylPheAlanor-C-Sta i-propyl ester

MorpholinocarbonylPheAla (0.15 g) was coupled to nor-C-StaOiPr (0.13 g) using DEC as described in Example 76. The crude material was chromatographed (24:1 CH$_2$Cl$_2$:EtOH) to afford 0.18 g pure product. NMR (300 MHz, CDCl$_3$) delta 1.26 (d, J=7 Hz, 3H), 4.29 (m, 1H), 4.38 (m, 1H), 4.48 (m, 1H), 4.96 (m, 1H).

EXAMPLE 82

MorpholinocarbonylPheGlnnor-C-Sta i-propyl ester (I, Z=morpholinocarbonylamino; M=phenyl; Q=H; R$_2$=(CH$_2$)$_2$CONH$_2$; X=cyclohexyl; W=CH⦀OH; and Z$^1$=CO$_2$CH(CH$_3$)$_2$)

A. morpholinocarbonylPheGln

Glutamine (0.30 g) was allowed to react with morpholinocarbonylPheOSuc (0.50 g) as described in Example 80, affording 0.37 g crude product which was used without further purification. NMR (300 MHz, DMSO-d$_6$) delta 3.43 (m, 4H), 4.15 (m, 1H), 4.31 (m, 1H).

B. morpholinocarbonylPheGlnnor-C-Sta i-propyl ester

MorpholinocarbonylPheGln (0.37 g) was coupled to nor-C-StaOiPr (0.24 g) using DEC as described in Example 76. The crude material was chromatographed (9:1 CH$_2$Cl$_2$:EtOH) to afford 0.18 g pure product. NMR (300 MHz, DMSO-d$_6$) delta 1.17 (d, J=7 Hz, 6H), 3.94 (m, 1H), 4.8 (m, 2H), 4.25 (m, 1H), 4.80 (m, 1H).

EXAMPLE 83

MorpholinocarbonylPheNlenor-C-Sta 3-methyl-2-propanol ester (I, Z=morpholinocarbonylamino; M=phenyl; Q=H; R$_2$=n-butyl; X=cyclohexyl; W=CH⦀OH; Z$^1$=CO$_2$CH(CH$_3$)CH(CH$_3$)$_2$)

A. nor-C-Sta 3-methyl-2-propanol ester hydrochloride

A solution of 100 mg Boc-nor-C-Sta in 5 mL 3-methyl-2-propanol was saturated with anhydrous HCl and was stirred overnight. The solution was concentrated in vacuo to afford 89 mg crude product which was carried on without further purification. NMR (300 MHz, DMSO-d$_6$) delta 1.17 (d, J=7 Hz, 3H), 4.10 (m, 1H), 4.70 (m, 1H).

B. morpholinocarbonylPheNlenor-C-Sta 3-methyl-2-propanol ester

MorpholinocarbonylPheNle (113 mg, Example 63) was coupled to HCl-nor-C-Sta, 3-methyl-2-propanol ester (89 mg) using the standard DEC reaction described in Example 58. The crude product was chromatographed (19:1 CH$_2$Cl$_2$:MeOH) to afford 79 mg pure product as a mixture of diastereomers at the ester methyl. NMR (300 MHz, CDCl$_3$) delta 1.13 (d, J=6 Hz, 3H), 4.15 (m, 1H), 4.71 (m, 1H).

EXAMPLE 84

MorpholinocarbonylPheS-MeCysnor-C-Sta i-butyl ester (I, Z=morpholinocarbonylamino; M=phenyl; Q=H; R$_2$=CH$_3$SCH$_2$—; X=cyclohexyl; W=CH∥∥∥∥OH; and Z$^1$=CH$_2$CH(CH$_3$)$_2$)

A. nor-phenylSta i-butyl ester

A solution of N-Boc-2(R)-hydroxy-3(S)-amino-4-phenylbutanitrile (1.0 g) in 40 mL isobutyl alcohol was saturated with anhydrous HCl and was stirred for 48 hours at RT. The solution was concentrated and the residue was diluted with 100 mL 0.1N HCl. After stirring for 15 minutes, the solution was washed 2×100 mL ether. The aqueous phase was made basic and extracted 2×100 mL EtOAc. The combined extracts were dried over MgSO$_4$, filtered and concentrated in vacuo to afford 0.43 g crude product which was used without further purification. NMR (300 MHz, CDCl$_3$) delta 0.93 (d, J=6 Hz, 3H), 3.34 (m, 1H), 3.97 (m, 2H), 4.07 (d, J=3 Hz, 1H).

B. nor-C-Sta i-butyl ester

A mixture of 95 mg nor-PhStaOiBu and 190 mg 10% Rh/C in 5 mL meOH was hydrogenated at 50 p.s.i. for 36 hours. The mixture was filtered through Celite and concentrated. The residue was dissolved in 50 mL 0.1N HCl and washed 2×50 mL ether. The aqueous phase was made basic and extracted 2×50 mL EtOAc. The combined extracts were dried over MgSO$_4$, filtered and concentrated to afford 74 mg crude product which was used without further purification. NMR (300 MHz, CDCl$_3$) delta 0.92 (d, J=6 Hz, 3H), 4.03 (m, 2H).

C. morpholinocarbonylPheS-MeCysnor-C-Sta i-butyl ester

MorpholinocarbonylPheSMeCys (113 mg, Example 58) was coupled to nor-C-StaOiBu (70 mg) using the DEC procedure described in Example 76. The crude material was chromatographed (19:1 CH$_2$Cl$_2$:MeOH) to afford 127 mg pure product. NMR (300 MHz, CDCl$_3$) delta 0.95 (d, J=6 Hz, 3H), 2.13 (s, 3H), 3.95 (m, 2H), 4.43 (m, 2H).

EXAMPLE 85

MorpholinocarbonylPheSMeCysnor-C-Sta t-butyl ester (I, Z=morpholinocarbonylamino; M=phenyl; Q=H; R$_2$=CH$_3$SCH$_2$—; X=cyclohexyl; W=CH∥∥∥∥OH; Z$^1$=CO$_2$C(CH$_3$)$_3$)

A. nor-phenylSta t-butyl ester

The procedure for the preparation of norPhStaOiBu (Example 83) was followed for 3.0 g nitrile in 200 mL t-butanol. This afforded 184 mg crude product after work-up, which was used without further purification. NMR (300 MHz, CDCl$_3$) delta 1.39 (s, 9H), 3.64 (m, 1H), 3.83 (d, J=3 Hz, 1H).

B. nor-C-Sta t-butyl ester nor-PheStaOtBu (75 mg) was hydrogenated as in Example 83 to afford 64 mg crude product after work-up. NMR (300 MHz, CDCl$_3$) delta 1.32 (s, 9H), 3.47 (m, 1H), 3.18 (br, 1H).

C. morpholinocarbonylPheS-MeCysnor-C-Sta t-butyl ester

MorpholinocarbonylPheSMeCys (97 mg, Example 58) was coupled to 60 mg nor-C-StaOtBu using the DEC procedure described in Example 76. The crude material was chromatographed (19:1 CH$_2$Cl$_2$:MeOH) to afford 50 mg pure product. NMR (300 MHz, CDCl$_3$) delta 1.35 (s, 9H), 2.13 (s, 3H), 3.98 (m, 1H), 4.30 (m, 1H), 4.57 (m, 2H).

EXAMPLE 86

MorpholinocarbonylPheS-MeCysnor-C-Sta N-methyl amide (I, Z=morpholinocarbonylamino; M=phenyl; Q=H; R$_2$=CH$_3$SCH$_2$; X=cyclohexyl; W=CH∥∥∥∥OH; and Z$^1$=CONHCH$_3$)

A. Boc-nor-C-Sta N-methyl amide

Boc-nor-C-Sta (0.25 g) was coupled to 57 mg methylamine-HCl using the standard DCC reaction described in Example 55. The crude material was chromatographed (2:1 EtOAc:Hex) to afford 0.16 g pure product. NMR (300 MHz, CDCl$_3$) delta 1.41 (s, 9H), 2.82 (d, J=5 Hz, 3H), 3.85 (m, 1H).

B. nor-C-Sta N-methyl amide

Boc-nor-C-StaNHMe (0.16 g) was deprotected using HCl in dioxane as described in Example 63 to afford 0.13 g crude salt which was used without further purification. NMR (300 MHz, DMSO-d$_6$) delta 2.62 (s, 3H), 3.97 (d, J=4 Hz, 1H).

C. morpholinocarbonylPheS-MeCysnor-C-Sta N-methyl amide

MorpholinocarbonylPheSMeCys (98 mg, Example 58) was coupled to 73 mg HCl-nor-C-StaNHMe using the DEC procedure described in Example 58. The crude material was chromatographed (19:1 CH$_2$Cl$_2$:EtOH) to afford 52 mg product as a mixture of SMCys epimers NMR (one isomer) (300 MHz, CDCl$_3$) delta (2.02 (s, 3H), 2.79 (d, J=5 Hz, 1H), 4.29 (m, 1H), 4.57 (m, 2H).

EXAMPLE 87

MorpholinocarbonylPheS-MeCysnor-Ph-Sta i-propyl ester (I, Z=morpholinocarbonylamino; M=phenyl; Q=H; R$_2$=CH$_3$SCH$_2$; X=phenyl; W=CH∥∥∥∥OH; Z$^1$=CO$_2$CH(CH$_3$)$_2$)

A. nor-phenyl-Sta i-propyl ester

Nor-Ph-StaOiPr was prepared from 118 mg of the nitrile in an analogous manner as the isobutyl ester (Example 84). The afforded 89 mg crude product which was used without further purification. NMR (300 MHz, CDCl$_3$) delta 1.26 (d, J=7 Hz, 6H), 3.30 (m, 1H), 4.01 (d, J=2 Hz, 1H), 5.10 (m, 1H).

B. morpholinocarbonylPheS-MeCysnor-phenyl-Sta i-propyl ester

MorpholinocarbonylPheSMeCys (0.96 g, Example 58) was coupled to 0.55 g nor-PhStaOiPr using the DEC procedure described in Example 76. The crude material was chromatographed (19:1 CH$_2$Cl$_2$:MeOH) to afford 0.91 g pure product. NMR (300 MHz, CDCl$_3$) delta 1.18 (d, J=7 Hz, 3H), 1.21 (d, J=7 Hz, 3H), 2.00 (s, 3H), 4.41 (m, 2H), 4.49 (m, 1H), 5.00 (m, 1H).

EXAMPLE 88

MorpholinocarbonylO-MeTyrNlenor-C-Sta i-propyl ester (I, Z=morpholinocarbonylamino; M=p-methoxyphenyl; Q=H; R$_2$=n-butyl; X=cyclohexyl; W=CH||||||OH; and Z$^1$=CO$_2$CH(CH$_3$)$_2$)

A. BocO-MeTyr methyl ester

A solution of 7.3 g BocTyr in 100 mL MeOH was treated with a large excess of diazomethane in 250 mL ether. At times 24 hours and 48 hours, more diazomethane was added. After 72 hours total, the reaction was quenched with HOAc, concentrated, diluted with 100 mL EtOAc and washed 2×50 mL saturated NaHCO$_3$. The organic phase was dried over MgSO$_4$, filtered and concentrated. The residue was chromatographed (9:1 Hex:EtOAc) to afford 6.4 g pure product. NMR (300 MHz, CDCl$_3$) delta 1.42 (s, 9H), 3.69 (s, 3H), 3.76 (m, 3H), 4.51 (m, 1H).

B. O-MeTyr methyl ester hydrochloride

BocO-MeTyrOme (6.4 g) was deprotected using HCl in dioxane as described in Example 63. This afforded 5.1 g crude product which was used without further purification. NMR (300 MHz, DMSO-d$_6$) delta 3.76 (s, 3H), 3.74 (s, 3H), 4.19 (m, 1H).

C. O-MeTyr methyl ester isocyanate

Into a suspension of 5.1 g HCl-O-MeTyrOMe in 150 ml toluene was bubbled phosgene as the temperature was slowly increased to reflux. After all material had dissolved, the solution was cooled and concentrated in vacuo to 7.0 g crude isocyanate. NMR (300 MHz, CDCl$_3$) delta 3.85 (s, 6H), 4.27 (m, 1H), 6.89 (d, J=8 Hz, 2H), 7.14 (d, J=8 Hz, 2H).

D. morpholinocarbonylO-MeTyr methyl ester

To a solution of 5.0 g O-MeTyrOMe-isocyanate in 50 mL CH$_2$Cl$_2$ at 0° was added 2.4 g morpholine. After stirring for 15 minutes, the solution was concentrated and the residue was chromatographed (EtOAc) to afford 3.6 g pure product. NMR (300 MHz, CDCl$_3$) delta 3.66 (s, 3H), 3.72 (s, 3H), 4.67 (m, 1H), 4.91 (d, J=8 Hz, 1H).

E. morpholinocarbonylO-MeTyr

MorpholinocarbonylO-MeTyrOMe (3.6 g) was saponified as described in Example 55 to afford 3.0 crude acid which was used without further purification. NMR (300 MHz, CDCl$_3$) delta 3.78 (s, 3H), 4.61 (m, 1H), 6.82 (d, J=8 Hz, 2H), 7.08 (d, J=8 Hz, 2H).

F. morpholinocarbonylO-MeTyrNle benzyl ester

MorpholinocarbonylO-MeTyr (0.50 g) was coupled to 0.42 g HCl-NleOBn using the standard DEC reaction (Example 58). The crude material was chromatographed (19:1 CH$_2$Cl$_2$:MeOH) to afford 0.77 g pure product. NMR (300 MHz, CDCl$_3$) delta 3.76 (s, 3H), 4.50 (m, 2H), 5.13).

G. morpholinocarbonylO-MeTyrNle

A mixture of 0.77 g morpholinocarbonylO-MeTyrNleOBn and 0.38 g 10% Pd on carbon in 60 mL EtOH was hydrogenated at 50 p.s.i. for 3 hours. The mixture was filtered through Celite and concentrated in vacuo to afford 0.63 g crude acid. NMR (300 MHz, CDCl$_3$) delta 3.72 (s, 3H), 4.44 (m, 1H), 4.63 (m, 1H).

H. morpholinocarbonylO-MeTyrNlenor-C-Sta i-propyl ester

MorpholinocarbonylO-MeTyrNle (74 mg) was coupled to 51 mg HCl-nor-C-StaOiPr using the standard DCC reaction described in Example 55. The crude material was chromatographed (19:1 CH$_2$Cl$_2$:MeOH) to afford 98 mg pure product. NMR (300 MHz, CDCl$_3$) delta 3.78 (s, 3H), 4.21 (m, 1H), 4.42 (m, 2H), 5.03 (m, 1H).

EXAMPLE 89

MorpholinocarbonylO-MeTyrS-MeCysnor-C-Sta i-propyl ester (I, Z=morpholinocarbonylamino M=p-methoxyphenyl; Q=H; R$_2$=CH$_3$SCH$_2$—; X=cyclohexyl; W=CH||||||OH; and Z$^1$=CO$_2$CH(CH$_3$)$_2$)

A. morpholinocarbonylO-MeTyrS-MeCys methyl ester

MorpholinocarbonylO-MeTyr (0.25 g, Example 36) was coupled to 0.36 g HCl-S-MeCysOMe using the standard DEC reaction described in Example 58. This afforded 0.32 g crude product which was used without further purification. NMR (300 MHz, CDCl$_3$) delta 2.01 (s, 3H), 3.71 (s, 3H), 3.74 (s, 3H), 4.55 (m, 1H), 4.65 (m, 1H).

B. morpholinocarbonylO-MeTyrS-MeCys

MorpholinocarbonylO-MeCysOMe (0.32 g) was saponified as described in Example 55 to afford 0.28 g crude acid which was used without further purification. NMR (300 MHz, CDCl$_3$) delta 2.11 (s, 3H), 3.78 (s, 3H), 4.69 (m, 1H), 4.77 (m, 1H).

C. morpholinocarbonylO-MeTyrS-MeCysnor-C-Sta i-propyl ester

MorpholinocarbonylO-MeCys (0.17 g) was coupled to 0.10 g HCl-nor-C-StaOiPr using the standard DEC reaction described in Example 58. The crude material was chromatographed (19:1 CH$_2$Cl$_2$:EtOH) to afford 0.18 g pure product. NMR (300 MHz, CDCl$_3$) delta 2.08 (s, 3H), 3.75 (s, 3H), 4.39 (m, 3H), 5.01 (m, 1H).

EXAMPLE 90

MorpholinocarbonylO-MeTyrNlenor-C-Sta methyl ester (I, Z=morpholinocarbonylamino; M=p-methoxyphenyl; Q=H; R$_2$=n-butyl; X=cyclohexyl; W=CH||||||OH; and Z$^1$=CO$_2$CH$_3$)

MorpholinocarbonylTyrNle (100 mg, Example 88) was coupled to 65 mg HCl-nor-C-StaOMe (Example 55) using the standard DEC reaction (Example 58). The crude material was chromatographed (19:1 CH$_2$Cl$_2$:MeOH) to afford 121 mg pure product. NMR (300 MHz, CDCl$_3$) delta 3.80 (s, 3H), 3.82 (s, 3H), 4.26 (m, 1H), 4.45 (m, 2H).

EXAMPLE 91

MorpholinocarbonylO-MeTyrNlenor-C-Sta N-methyl amide (I, Z=morpholinocarbonylamino; M=p-methoxyphenyl; Q=H; R$_2$=n-butyl; X=cyclohexyl; W=CH||||||OH; and Z$^1$=CONHCH$_3$ MorpholinocarbonylO-MeTyrNle (132 mg, Example 88) was coupled to 78 mg HCl-nor-C-StaNHMe (Example 86) using the standard DCC reaction described in Example 55. The crude material was chromatographed (9:1 CH$_2$Cl$_2$:MeOH) to afford 155 mg pure product.

NMR (300 MHz, CDCl$_3$) delta 2.79 (d, J=5 Hz, 3H), 3.75 (s, 3H), 4.22 (m, 1H), 4.30 (m, 2H).

EXAMPLE 92

MorpholinocarbonylTyrS-MeCysnor-C-Sta i-propyl ester (I, Z=morpholinocarbonylamino; M=p-hydroxyphenyl; Q=H; R X=cyclohexyl; W=CH""""OH; and Z$^1$=CO$_2$CH(CH$_3$)$_2$)

A. BocS-MeCysnor-C-Sta i-propyl ester

BocS-MeCys (1.1 g) was coupled to 1.0 g nor-C-StaOiPr using DEC as described in Example 76 to afford 1.8 g crude material which was used without further purification. NMR (300 MHz, CDCl$_3$) delta 1.25 (d, J=6 Hz, 6H), 1.43 (s, 9H), 2.14 (s, 3H), 4.08 (m, 1H), 4.43 (m, 1H), 4.98 (m, 1H).

B. S-MeCysnor-C-Sta i-propyl ester hydrochloride

BocS-MeCys-nor-C-StaOiPr (0.42 g) was deprotected using HCl in dioxane as described in Example 63 to afford 0.38 g crude salt which was used without further purification. NMR (300 MHz, DMSO-d$_6$) delta 1.19 (d, J=6 Hz, 3H), 1.20 (d, J=6 Hz, 3H), 2.16 (s, 3H), 3.95 (m, 1H), 4.20 (m, 1H), 4.83 (m, 1H).

C. morpholinocarbonyl O-benzylTyr

To a solution of 0.5 g O-benzylTyr in 20 mL dioxane and 5 mL 2N NOH was added 0.31 g morpholinocarbonylchloride and the resulting mixture was stirred at RT overnight. The solution was concentrated and the residue was diluted with 200 mL H$_2$O and washed 2×200 mL ether. The aqueous phase was acidified and extracted 2×200 mL CHCl$_3$. The combined extracts were dried over MgSO$_4$, filtered and concentrated to 0.18 g crude product which was used without further purification. NMR (300 MHz, DMSO-d$_6$) delta 4.13 (m, 1H), 5.04 (s, 2H).

D. morpholinocarbonylTyr

A mixture of 0.18 g morpholinocarbonylO-benzylTyr and 0.18 g 10% Pd on carbon in 20 mL MeOH was hydrogenated at 50 p.s.i. for 18 hours. The mixture was filtered through Celite and concentrated to afford 0.14 g crude acid which was used without further purification. NMR (300 MHz, DMSO-d$_6$) delta 4.04 (m, 1H), 6.58 (d, J=8 Hz, 2H), 6.95 (d, J=8 Hz, 2H).

E. morpholinocarbonylTyrS-MeCysnor-C-Sta i-propyl ester morpholinocarbonylTyr (0.13 g) was coupled to 0.27 g HClS-MeCysnor-C-StaOiPr using the standard DEC reaction (Example 58). The crude product was chromatographed (9:1 CH$_2$Cl$_2$:MeOH) to afford 0.15 g pure product. NMR (300 MHz, CDCl$_3$) delta 1.24 (d, J=6 Hz, 3H), 1.26 (d, J=6 Hz, 3H), 4.41 (m, 3H), 5.02 (m, 1H).

EXAMPLE 93

Morpholinocarbonyl o-TyrS-MeCysnor-C-Sta i-propyl ester (I, Z=morpholinocarbonylamino; M=o-hydroxyphenyl; Q=H; R$_2$=CH$_3$SCH$_2$—; X=cyclohexyl; W=CH""""OH; and Z$^1$=CO$_2$CH(CH$_3$)$_2$)

A. Boc o-Tyr

To a mixture of 1.1 g o-Tyr in 15 mL THF and 15 mL 20% Na$_2$CO$_3$ was added 2.0 g Boc$_2$O and the resulting mixture was stirred at RT for 3 hours. The reaction was diluted with 30 mL H$_2$O, acidified and extracted 3×50 mL CH$_2$Cl$_2$. The combined extracts were dried over MgSO$_4$, filtered and concentrated. The residue was recrystallized from ether-hexane to afford 1.2 g pure product. NMR (300 MHz, DMSO-d$_6$) delta 1.32 (s, 9H), 4.13 (m, 1H).

B. Boc O-benzyl-o-Tyr benzyl ester

A mixture of 1.2 g Boc-oTyr, 1.1 mL benzylbromide and 1.3 g K$_2$CO$_3$ in 40 mL acetone was heated to reflux for 20 hours. Additional reagents (benzylbromide 0.25 mL, K$_2$CO$_3$ 0.36 g) were added and heating was continued for 2 hours. The cooled mixture was diluted with 40 mL H$_2$O and extracted 3×75 mL EtOAc. The combined extracts were washed 3×50 mL H$_2$O, dried over MgSO$_4$, filtered and concentrated. Chromatography (4:1 Hex:EtOAc. The combined extracts were washed 3×50 mL H$_2$O, dried over MgSO$_4$, filtered and concentrated. Chromatography (4:1 Hex:EtOAc) afforded 1.25 g pure product. NMR (300 MHz, CDCl$_3$) delta 1.38 (s, 9H), 4.58 (m, 1H), 5.06 (m, 4H).

C. O-benzyl-o-Tyr benzyl ester hydrochloride

BocO-benzyl-o-Tyr benzyl ester (1.25 g) was deprotected using HCl in dioxane as described in Example 63 to afford 1.1 g crude salt which was used without further purification. NMR (300 MHz, DMSO-d$_6$) delta 4.24 (m, 1H), 5.02 (AB, 2H), 5.12 (s, 2H).

D. morpholinocarbonylO-benzyl-o-Tyr benzyl ester

O-Benzyl-o-Tyr benzyl ester (1.1 g) was treated with phosgene in refluxing toluene as described in Example 88. The crude isocyanate was dissolved in 15 mL CH$_2$Cl$_2$, cooled to 0° and treated with 0.35 g morpholine. The solution was stirred at RT for 3 hours, after which it was diluted with 50 mL EtOAc and washed with 15 mL 0.1N HCl and 2×15 mL saturated NaHCO$_3$. The organic phase was dried over MgSO$_4$, filtered and concentrated. The residue was chromatographed (2:3 Hex:EtOAc) to afford 0.60 g pure product. NMR (300 MHz, CDCl$_3$) delta 4.65 (m, 1H), 5.06 (AB, 2H), 5.07 (s, 2H).

E. morpholinocarbonylO-benzyl-o-Tyr

A mixture of 0.60 g morpholinocarbonyl-O-benzyl-o-Tyr benzyl ester and 2 g K$_2$CO$_3$ in 5 mL H$_2$O and 15 mL MeOH was heated to reflux for 18 hours. The solution was concentrated and the residue was diluted with 30 mL H$_2$O and washed 2×25 mL ether. The aqueous layer was acidified and extracted 3×50 mL EtOAc. The combined extracts were dried over MgSO$_4$, filtered and concentrated to afford 0.35 g crude acid. NMR (300 MHz, DMSO-d$_6$) delta 4.37 (m, 1H), 5.12 (s, 2H).

F. morpholinocarbonyl-o-Tyr

A mixture of 0.35 g morpholinocarbonylO-benzyl-o-Tyr and 0.35 g 10% Pd on carbon in 30 mL MeOH was hydrogenated at 50 p.s.i. for 18 hours. The mixture was filtered through Celite and concentrated to afford 0.33 g crude material. NMR (300 MHz, DMSO-d$_6$) delta 4.16 (m, 1H).

G. morpholinocarbonyl-o-TyrS-MeCysnor-C-Sta i-propyl ester

Morpholinocarbonyl-o-Tyr (0.10 g) was coupled to 0.12 g S-MeCys-nor-C-StaOiPr using DEC as described in Example 76. The crude material was chromatographed (9:1 CH$_2$Cl$_2$:MeOH) to afford 0.13 g pure product as a mixture at the o-Tyr position. NMR (one isomer) (300 MHz, CDCl$_3$) delta 1.98 (s, 3H), 4.36 (m, 3H), 4.97 (m, 1H).

EXAMPLE 94

Morpholinocarbonyl p-ClTyrS-MeCysnor-C-Sta i-propyl ester (I, Z=morpholinocarbonylamino; M=p-chlorophenyl; Q=H; R$_2$=CH$_3$SCH$_2$; X=cyclohexyl; W=CH⦀OH; Z$^1$=CO$_2$CH(CH$_3$)$_2$)

A. morpholinocarbonyl-p-chloroTyr

To a solution of 0.5 g p-chloroTyr in 5 mL 2N NaOH and 20 mL dioxane was added 0.36 g morpholinecarbonylchloride as described in Example 92 to afford 0.26 g crude product which was used without further purification. NMR (300 MHz, DMSO-d$_6$) delta 4.65 (m, 1H), 6.97 (d, J=8 Hz, 2H), 7.19 (d, J=8 Hz, 2H).

B. morpholinocarbonyl p-ClTyrS-MeCysnor-C-Sta ipropyl ester

Morpholinocarbonyl p-ClTyr (70 mg) was coupled to 82 mg S-MeCysnor-C-StaOiPr using DEC as described in Example 76. The crude material was chromatographed (19:1 CH$_2$Cl$_2$:MeOH) to afford 118 mg pure product as a mixture of isomers at the pCTyr position. NMR (one isomer) (300 MHz, CDCl$_3$) delta 1.97 (s, 3H), 4.37 (m, H), 5.96 (m, 1H).

EXAMPLE 95

2-Morpholino-3-phenylpropionylNlenor-C-Sta i-propyl ester (I, Z=morpholino; M=phenyl; Q=H; R$_2$=n-butyl; X=cyclohexyl; W=CH⦀OH; and Z$^1$=CO$_2$CH(CH$_3$)$_2$)

A. ethyl 2-morpholino-3-phenylpropionate

A solution of 2.0 g ethyl 2-bromo-3-phenylpropionate and 2.8 g morpholine in 5 mL DMF was stirred overnight at RT. The mixture was diluted with 75 mL 1% HCl and washed 3×50 mL ether. The aqueous phase was made basic and extracted 3×100 mL EtOAc. The combined extracts were dried over MgSO$_4$, filtered and concentrated. The residue was chromatographed (35% EtOAc:Hex) to afford 0.8 g pure product. NMR (300 MHz, CDCl$_3$) delta 1.12 (t, J=7 Hz, 3H), 3.36 (m, 1H), 4.04 (m, 2H).

B. 2-morpholino-3-phenylpropionic acid

A solution of 0.65 g of the ethyl ester of Example 95A in 3.7 mL 1N NaOH and 5 mL MeOH was refluxed for 3 hours. The solution was acidified with anhydrous HCl and concentrated. The residue was dried thoroughly on high vacuum. NMR (300 MHz, DMSO-d$_6$) delta 3.90 (br, 4H), 4.15 (m, 1H).

C. 2-morpholino-3-phenylpropionylNle benzyl ester

The product of Example 95B (0.35 g) was coupled to 0.33 g NleObenzyl ester using DEC as described in Example 58. The crude material was chromatographed (39:1 CH$_2$Cl$_2$:MeOH) to afford 0.45 g product as a mixture of isomers at the asymmetric 2-carbon of the propionyl moiety. NMR (one isomer) (300 MHz, CDCl$_3$) delta 3.68 (m, 4H), 4.57 (m, 1H), 5.17 (AB, 2H).

D. 2-morpholino-3-phenylpropionylNle

The product of Example 95C (0.55 g) was deprotected by hydrogenation (40 psi) with 0.28 g 10% Pd on carbon in 50 mL MeOH for 2 hours. The mixture was filtered through Celite and concentrated to afford 0.41 g crude acid which was used without further purification. NMR (300 MHz, DMSO-d$_6$) delta 3.74 (m, 4H), 4.38 (m, 1H).

E. 2-morpholino-3-phenylpropionylNlenor-C-Sta i-propyl ester

The product of Example 95D (54 mg) was coupled to 43 mg HCl-nor-C-StaOiPr using DEC as described in Example 58. The crude material was chromatographed (19:1 CH$_2$Cl$_2$:MeOH) to afford 49 mg pure product and 47 mg of the MPP diastereomer. NMR (300 MHz, CDCl$_3$) delta 4.12 (m, 1H), 4.39 (m, 1H), 5.00 (m, 1H).

EXAMPLE 96

2-(4-Methylpiperazino)-3-phenylNlenor-C-Sta i-propyl ester (I, Z=4-methylpiperazino; M=phenyl; X=cyclohexyl; Q=H; R$_2$=n-butyl; W=CH⦀OH; and Z$^1$=CO$_2$CH(CH$_3$)$_2$)

A. 2-(4-methylpiperazino)-3-phenylpropionic acid ethyl ester

Ethyl 2-bromo-3-phenylpropionate (1.95 g) was treated with 3.05 g N-methylpiperazine as described in Example 95 to afford 0.30 g pure product after chromatography (9:1 CH$_2$Cl$_2$:MeOH). NMR (300 MHz, CDCl$_3$) delta 1.10 (d, J=7 Hz, 3H), 2.26 (s, 3H), 3.37 (m, 1H), 4.00 (m, 2H).

B. 2-(4-methylpiperazino)-3-phenylpropionic acid

A mixture of 0.56 g of the ethyl ester of Example 96A in 31 mL 1N NaOH and 20 mL EtOH was refluxed for 16 hours. Anhydrous HCl was bubbled in and the mixture was concentrated. The residue was dissolved in warm iPrOH-MeOH (1:1) and filtered and the filtrate was concentrated to afford 0.55 g crude product. NMR (300 MHz, DMSO-d 2.72 (s, 3H), 3.80 (m, 1H).

C. 2-(4-methylpiperazino)-3-phenylpropionylNle benzyl ester

The product of Example 96B (0.55 g) was coupled to 0.51 g NleOBn using the DEC procedure described in Example 58. The crude material was chromatographed (19:1 CH$_2$Cl$_2$:MeOH) to afford 0.42 g product as a mixture of epimers at the asymmetric 2-carbon of the propionyl group. NMR (300 MHz, CDCl$_3$) delta 1.27 (s, 3H), 2.85 (m, 1H), 3.26 (m, 1H), 4.54 (m, 1H).

D. 2-(4-methylpiperazino)-3-phenylpropionylNle

The product of example 96C (0.42 g) was deprotected as described in Example 95 to afford 0.31 g of crude acid which was used without further purification. NMR (300 MHz, DMSO-d$_6$) delta 2.48 (s, 3H), 4.32 (m, 1H).

E. 2-(4-methylpiperazino)-3-phenylpropionylNle nor-C-Sta i-propyl ester

The product of Example 96D (76 mg) was coupled to 60 mg HCl-nor-C-StaOiPr using DEC (Example 58). The crude material was chromatographed (9:1 CH$_2$Cl$_2$:MeOH) to afford 30 mg and 33 mg of epimers. NMR (300 MHz, CDCl$_3$) delta 2.35 (s, 3H), 4.16 (m, 1H), 4.40 (m, 1H), 5.01 (m, 1H).

EXAMPLE 97

2-(3,5-dioxomorpholino)-3-phenylpropionylNlenor-C-Sta i-propyl ester (I, Z=3,5-dioxomorpholino; M=phenyl; Q=H; $R_2$=n-butyl; X=cyclohexyl; W=CH‖‖‖ OH; and $Z^1$=$CO_2CH(CH_3)_2$

A. 2-(3,5-dioxomorpholino)-3-phenylpropionic acid benzyl ester

To a solution of 0.21 g HCl-PheO-benzyl ester and 0.10 mL TEA in 10 mL $CH_2Cl_2$ was added 80 mg glycolic anhydride. The solution was stirred at RT for 2 hours. The mixture was diluted with 200 mL EtOAc and washed 2×20 mL 0.1N HCl, 20 mL $H_2O$ and 20 mL brine. The organic phase was dried over $MgSO_4$, filtered and concentrated to afford 0.32 g crude product. NMR (300 MHz, $CDCl_3$) delta 3.14 (m, 2H), 4.12 (m, 4H), 4.95 (m, 1H), 5.13 (AB, 2H).

A solution of the above crude acid and 76 mg pyridine in 5 mL $Ac_2O$ was heated to 100° for 18 hours. The reaction was added to 100 mL $H_2O$ and was extracted 2×100 mL EtOAc. The combined extracts were washed with 20 mL 0.1N HCl, 20 mL 0.1N NaOH and 20 mL $H_2O$. The organic phase was dried over $MgSO_4$, filtered and concentrated to afford 0.23 g crude product. NMR (300 MHz, $CDCl_3$) delta 4.18 (2AB, 4H), 5.19 (AB, 2H), 5.53 (m, 1H).

B. 2-(3,5-dioxomorpholino)-3-phenylpropinic acid

The product of Example 97A was deprotected as described in Example 95 to afford 0.15 g of crude product. NMR (300 MHz, DMSO-$d_6$) delta 4.32 (AB, 4H), 5.30 (m, 1H).

C. 2-(3,5-dioxomorpholino)-3-phenylpropionylNle benzyl ester

The product of Example 97B (0.15 g) was coupled to 0.16 g HCl-NleObenzyl ester using the standard DEC reaction described in Example 58. The crude material was chromatographed (4:1 $CH_2Cl_2$:MeOH) to afford 0.14 g pure product. NMR (300 MHz, $CDCl_3$) delta 4.18 (AB, 4H), 4.63 (m, 1H), 5.16 (AB, 2H).

D. 2-(3,5-dioxomorpholino)-3-phenylpropionylNle

The product of Example 97C (0.14 g) was deprotected as described in Example 95 to afford 0.12 g crude product. NMR (300 MHz, DMSO-$d_6$) delta 4.24 (AB, 4H), 4.62 (m, 1H), 5.17 (m, 1H).

E. 2-(3,5-dioxomorpholino)-3-phenylpropionylNle nor-C-Sta i-propyl ester

The product of Example 97D (0.12 g) was coupled to HCl-nor-C-StaOiPr using the standard DEC reaction described in Example 58. The crude material was chromatographed (19:1 $CH_2Cl_2$:MeOH) to afford 88 mg pure product. NMR (300 MHz, $CDCl_3$) delta 4.18 (m, 1H), 4.32 (s, 4H), 4.48 (m, 1H), 5.02 (m, 1H).

EXAMPLE 98

2-(3-Oxomorpholino)-3-phenylpropionylNlenor-C-Sta i-propyl ester (I, Z=3-oxomorpholino; M=phenyl; Q=H; $R_2$=n-butyl; X=cyclohexyl; W=CH‖‖‖‖‖OH; and $Z^1$=$CO_2CH(CH_3)_2$)

A. N-glycoloylphenylalanine benzyl ester

To a solution of 2.23 g of the acylation product between PheObenzyl ester and glycolic anhydride (Example 96) in 6.6 mL THF at 0° was added 1.1 eq $BH_3$-DMS slowly and the resulting solution was stirred for 5 hours. $H_2O$ (5 mL) was added dropwise followed by 5 mL 0.1N HCl. The mixture was added 150 mL $H_2O$, acidified and extracted 2×150 mL EtOAc. The combined extracts were washed 2×30 mL 0.1N NaOH, 30 mL $H_2O$. The organic phase was dried over $MgSO_4$, filtered and concentrated. The residue was chromatographed (39:1 $CH_2Cl_2$:MeOH) to afford 0.43 g pure product. NMR (300 MHz, $CDCl_3$) delta 3.99 (AB, 2H), 4.97 (m, 1H), 5.15 (AB, 2H).

B. N-(0-mesylglycolyl)phenylalanine benzyl ester

To a solution of 0.41 g of the above alcohol and 0.41 g TEA in 10 mL $CH_2Cl_2$ at 0° was added 0.11 mL mesyl chloride dropwise, and the resulting solution was stirred at 0° for 1 hour. The solution was diluted with 200 mL EtOAc and washed with 30 mL 0.1N HCl, 0.1N NaOH. The organic phase was dried over $MgSO_4$, filtered and concentrated to afford 0.25 g crude mesylate. NMR (300 MHz, $CDCl_3$) delta 2.92 (s, 3H), 4.29 (m, 2H), 4.92 (m, 1H), 5.13 (AB, 2H).

C. N-(iodoethoxyacetyl)phenylalanine benzyl ester

A mixture of 0.25 g of the above mesylate and 0.23 g NaI in 20 mL acetone was refluxed for 6 hours. The reaction was poured into 100 mL $H_2O$ and extracted 2×100 mL EtOAc. The combined extracts were washed with 50 mL brine, dried over $MgSO_4$, filtered and concentrated. The crude material was chromatographed (9:1 $CH_2Cl_2$:MeOH) to afford 0.35 g pure iodide. NMR (300 MHz, $CDCl_3$) delta 3.96 (s, 2H), 4.93 (m, 1H), 5.11 (AB, 2H).

D. 2-(3-oxomorpholino)-3-phenylpropionic acid benzyl ester

To a solution of 0.16 g of the above iodide in 3 mL THF at −78° was added 1.1 eq. $KNTMS_2$ dropwise and the resulting solution was stirred for 5 hours at −78°. $NH_4Cl$ (1 mL) was added slowly and the mixture was poured into 100 mL $H_2O$, acidified and extracted 2×100 mL EtOAc. The combined extracts were washed with 20 mL brine, dried over $MgSO_4$, filtered and concentrated. The residue was chromatographed (9:1 $CH_2Cl_2$:MeOH) to afford 71 mg pure product. NMR (300 MHz, $CDCl_3$) delta 4.10 (AB, 2H), 5.19 (AB, 2H), 5.27 (m, 1H).

E. 2-(3-oxomorpholino)-3-phenylpropionic acid

The product of Example 98C (96 mg) was deprotected as described in Example 95 to afford 70 mg crude acid. NMR (300 MHz, DMSO-$d_6$) delta 3.92 (AB, 2H), 5.04 (m, 1H).

F. 2-(3-oxomorpholino)-3-phenylpropionylNle benzyl ester

The product of Example 98D (90 mg) was coupled to 98 mg NleO benzyl ester using the standard DEC reaction described in Example 58. The crude material was chromatographed (39:1 $CH_2Cl_2$:MeOH) to afford 127 mg pure product. NMR (300 MHz, $CDCl_3$) delta 4.14 (s, 2H), 5.54 (m, 1H), 5.16 (m, 2H), 5.32 (m, 1H).

G. 2-(3-oxomorpholino)-3-phenylpropionylNle

The product of Example 98E (127 mg) was deprotected as described in Example 95 to afford 114 mg crude acid which was used without further purification. NMR (300 MHz, DMSO-$d_6$) delta 4.12 (br, 2H), 4.52 (br, 1H).

H. 2-(3-oxomorpholino)-3-phenylpropionylNlenor-C-Sta i-propyl ester

The product of Example 98F (114 mg) was coupled to 92 mg HCl-nor-C-staOiPr using the DEC reaction (Example 58). The crude material was chromatographed (19:1 $CH_2CL_2MeOH$) to afford 13 mg pure product. NMR (300 MHz, $CDCl_3$) delta 4.42 (m, 2H), 5.02 (m, 2H).

EXAMPLE 99

3-OxomorpholinocarbonylPheNlenor-C-Sta i-propyl ester (I, Z=3-oxomorpholinocarbonylamino; Q=H; M=phenyl; $R_2$=n-butyl; X=cyclohexyl; W=CH∥∥∥∥OH; and $Z^1=CO_2CH(CH_3)_2$)

A. 3-oxomorpholinocarbonylPhe benzyl ester

To a suspension of 79 mg pentane-washed NaH in 5 mL THF was added a solution of 200 mg 3-ketomorpholine in 10 mL THF. The resulting mixture was stirred for 5 minutes at RT and then cooled to 0°. A solution of 584 mg PheOBn-isocyanate in 15 mL THF was added dropwise and the resulting solution was stirred at 0° for 1 hour. The reaction mixture was poured into 100 mL $H_2O$ and extracted 2×100 mL EtOAc. The combined extracts were washed with 20 mL 0.1N HCl, 20 mL 0.1N NaOH, dried over $MgSO_4$, filtered and concentrated. The crude material was chromatographed (4:1 EtOAc: $CH_2Cl_2$) to afford 132 mg pure product. NMR (300 MHz, $CDCl_3$) delta 4.24 (s, 2H), 4.82 (m, 1H), 5.18 (AB, 2H).

B. 3-oxomorpholinocarbonylPhe

The product of Example 99A (0.64 g) was deprotected as described on Example 95 to afford 0.44 g crude acid. NMR (300 MHz, DMSO-$d_6$) delta 4.22 (s, 2H), 4.51 (m, 1H).

C. 3-oxomorpholinocarbonylPheNle benzyl ester

The product of Example 99B (0.44 g) was coupled to 0.41 g NleOBn using the standard DEC reaction (Example 58) to afford 0.73 g crude material which as used without further purification. NMR (300 MHz, $CDCl_3$) delta 4.25 (m, 2H), 4.61 (m, 1H), 4.16 (m, 2H).

D. 3-oxomorpholinocarbonylPheNle

The product of Example 99C (0.72 g) was deprotected as described in Example 95 to afford 0.56 g crude material. NMR (300 MHz, DMSO-$d_6$) delta 4.19 (m, 2H), 4.65 (m, 2H).

E. 3-oxomorpholinocarbonylPheNlenor-C-Sta i-propyl ester

The product of Example 99D (125 mg) was coupled to 91 mg HCl-nor-C-StaOiPr using DEC (Example 58). The crude material was chromatographed (19:1 $CH_2Cl_2$:MeOH) to afford 73 mg product. NMR (300 MHz, $CDCl_3$) delta 4.20 (m, 2H), 4.39 (m, 1H), 4.52 (m, 1H), 5.01 (m, 1H).

EXAMPLE 100

MethoxyethylaminocarbonylPheNlenor-C-Sta i-propyl ester (I, $Z=CH_3O(CH_2)_2NHCONH$; M=phenyl; Q=H; X=cyclohexyl; $R_2$=n-butyl; W=CH∥∥∥∥OH; and $Z^1=CO_2CH(CH_3)_2$)

A. methoxyethylaminocarbonylPhe benzyl ester

To a stirred solution of 0.20 g PheOBn-isocyanate in 10 mL $CH_2Cl_2$ was added 59 mg 0-Me-ethanolamine and the solution was stirred for 1 hour. The reaction was diluted with 200 mL ether and was washed with 20 mL 0.1N HCl and 20 mL 0.1N NaOH. The organic phase was dried over $MgSO_4$, filtered and concentrated to afford 0.20 g crude product. NMR (300 MHz, $CDCl_3$) delta 3.28 (s, 3H), 4.80 (m, 1H), 5.11 (m, 2H).

B. methoxyethylaminocarbonylPhe

A mixture of 0.20 g of the above benzyl ester and 0.10 g 10% Pd on carbon in 50 mL MeOH was hydrogenated at 50 p.s.i. for 2 hours. The mixture was filtered through Celite and concentrated to afford 0.19 g crude product. NMR (300 MHz, DMSO-$d_6$) delta 3.24 (s, 3H), 4.30 (m, 1H).

C. methoxyethylaminocarbonylPheNle benzyl ester

The above Phe derivative (0.19 g) was coupled to 0.14 g NleOBn using the standard DEC procedure (Example 58). This afforded 0.23 g crude material which was used without purification. NMR (300 MHz, $CDCl_3$) delta 3.26 (s, 3H), 4.52 (m, 2H), 5.10 (m, 2H).

D. methoxyethylaminocarbonylPheNle

A mixture of 0.23 g of the above compound and 0.12 g 10% Pd on carbon in 50 mL EtOH was hydrogenated at 50 p.s.i. for 2 hours. The mixture was filtered and concentrated to afford 0.16 g crude product. NMR (300 MHz, DMSO-$d_6$) delta 3.21 (s, 3H), 4.10 (m, 1H), 4.41 (m, 1H).

E. methoxyethylaminocarbonylPheNlenor-C-Sta i-propyl ester

The above acid (0.17 g) was coupled to 0.13 g HCl-nor-C-Sta OiPr using the standard DEC reaction (Example 58). The crude material was chromatographed (19:1 $CH_2Cl_2$:MeOH) to afford 0.18 g pure product. NMR (300 MHz, $CDCl_3$) delta 3.28 (s, 3H), 4.32 (m, 1H), 4.45 (m, 1H), 4.57 (m, 1H), 5.03 (m, 1H).

EXAMPLE 101

HydroxyethylaminocarbonylPheNlenor-C-Sta i-propyl ester (I, $Z=HO(CH_2)_2NHCONH$; M=phenyl; Q=H; $R_2$=n-butyl; X=cyclohexyl; W=CH∥∥∥∥OH; and $Z^1=CO_2CH(CH_3)_2$)

A. hydroxyethylaminocarbonylPhe benzyl ester

To a solution of 0.50 g PheOBn-isocyanate in 10 mL $CH_2Cl_2$ was added 0.12 g ethanolamine and the resulting solution was stirred 4 hours. The mixture was diluted with 200 mL EtOAc and was washed with 20 mL 0.1N HCl and 20 mL 0.1N NaOH. The organic phase was dried over $MgSO_4$, filtered and concentrated to afford 0.44 g crude product. NMR (300 MHz, $CDCl_3$) delta 4.79 (m, 1H), 4.12 (m, 2H).

B. t-butyldimethylsilyloxyethylaminocarbonylPhe benzyl ester

To a solution of 0.44 g of the above alcohol in 10 mL DMF was added 0.24 g t-butyldimethylsilylchloride and 0.22 g imidazole. After 18 hours, the solution was added to 150 mL H$_2$O and was extracted 2×150 mL EtOAc. The combined extracts were washed with 30 mL H$_2$O, dried over MgSO$_4$, filtered and concentrated. The residue was chromatographed (39:1 CH$_2$Cl$_2$:MeOH) to afford 0.50 g pure product. NMR (300 MHz, CDCl$_3$) delta 0.89 (s, 9H), 4.98 (m, 1H), 5.13 (m, 2H).

C. t-butyldimethylsilyloxyethylaminocarbonylPhe

A mixture of the above benzyl ester (0.18 g) and 0.09 g 10% Pd on carbon in 30 mL MeOH was hydrogenated at 50 p.s.i. for 3 hours. The mixture was filtered through Celite, and concentrated to afford 0.13 g crude material. NMR (300 MHz, DMSO-d$_6$) delta 0.89 (s, 3H), 4.27 (m, 1H).

D. t-butyldimethylsilyloxyethylaminocarbonylPheNle benzyl ester

The above acid (0.13 g) was coupled to 96 mg NleOBn using the DEC procedure (Example 58). Chromatography (19:1 CH$_2$Cl$_2$:MeOH) afforded 0.10 g pure product. NMR (300 MHz, DMSO-d$_6$) delta 0.91 (s, 9H), 4.50 (m, 2H), 4.72 (m, 1H), 5.11 (s, 2H).

E. t-butyldimethylsilyloxyethylaminocarbonylPheNle

The above product was deprotected by hydrogenation as described in Example 100, affording 78 mg crude material. NMR (300 MHz, DMSO-d$_6$) delta 0.88 (s, 9H), 4.00 (m, 1H), 4.37 (m, 1H).

F. t-butyldimethylsilyloxyethylaminocarbonylPheNle nor-C-Sta i-propyl ester

The above acid (73 mg) was coupled to 45 mg HCl-nor-C-StaOiPr (DEC, Example 58) to afford 116 mg crude product. NMR (300 MHz, CDC13) delta 0.86 (s, 9H), 4.38 (m, 1H), 4.45 (m, 1H), 5.02 (m, 1H).

G. hydroxyethylaminocarbonylPheNlenor-C-Sta i-propyl ester

The above material (116 mg) was deprotected by treatment with 1.5 eq. Bu$_4$NF in 5 mL THF for 2 hours. The solution was diluted with 200 mL EtOAc and was washed with 20 mL 0.1N HCl and 20 mL 0.1N NaOH. The organic phase was dried over MgSO$_4$, filtered and concentrated and the residue was chromatographed (9:1 CH$_2$Cl$_2$:MeOH) to afford 63 mg pure product. NMR (300 MHz, CDCl$_3$) delta 4.41 (m, 1H), 4.50 (m, 1H), 4.74 (m, 1H), 5.07 (m, 1H).

EXAMPLE 102

MorpholinosulfonylPheNlenor-C-Sta i-propyl ester (I, Z=morpholinosulfonylamino; M=phenyl; Q=H; R$_2$=n-butyl; X=cyclohexyl; W=CH⦀OH; and Z$^1$=CO$_2$CH(CH$_3$)$_2$)

A. morpholinosulfonylPheNle benzyl ester

A solution of 0.29 g PheNleOBn, 0.40 g morpholinosulfonylchloride and 0.36 g TEA in 10 mL CH$_2$Cl$_2$ was refluxed for 16 hours. Additional measures of the latter two reagents were added and heating was continued for 8 hours. The solution was diluted with 50 mL EtOAc and was washed with 25 mL 0.1N HCl and 25 mL 0.1N NaOH. The organic phase was dried over MgSO$_4$, filtered and concentrated, and the residue was chromatographed (2:1 Hex:EtOAc) to afford 0.36 g pure product. NMR (300 MHz, CDCl$_3$) delta 4.04 (m, 1H), 4.60 (m, 1H), 5.15 (m, 2H).

B. morpholinosulfonylPheNle

The above material (0.36 g) was deprotected (Example 100) to afford 0.30 g crude product. NMR (300 MHz, DMSO-d$_6$) delta 3.95 (m, 1H), 4.10 (m, 1H).

C. morpholinosulfonylPheNlenor-C-Sta i-propyl ester

The product of Example 102B (0.29 g) was coupled to 0.12 g HCl-nor-C-StaOiPr using DEC (Example 58). Chromatography (29:1 CH$_2$Cl$_2$:EtOH) afforded 0.29 g pure product. NMR (300 MHz, CDCl$_3$) delta 4.02 (m, 1H), 4.41 (m, H2H), 5.06 (m, 1H).

EXAMPLE 103

MorpholinomethylphosphonoPheNlenor-C-Sta i-propyl ester (I, Z=morpholinoP(OCH$_3$) (O)amino; M=phenyl; Q=H; R$_2$=n-butyl; X=cyclohexyl; W=CH⦀OH; Z$^1$=CO$_2$CH(CH$_3$)$_2$)

A. morpholinomthylphosphinicoPheNle benzyl ester

A solution of 0.30 g PheNleOBn, 0.30 g TEA and 0.44 g morpholino methyl chlorophosphate in 10 mL CH$_2$CL$_2$was stirred for 60 hours. The solution was diluted with 50 mL EtOAc and was washed with 25 mL 0.1N HCl and 0.1N NaOH. The organic phase was dried over MgSO$_4$, filtered and concentrated. The residue was chromatographed (19:1 CH$_2$Cl$_2$:EtOH) to afford 0.18 g product as a mixture of isomers at phosphorus. NMR (300 MHz, CDCl$_3$) delta 3.57 (d, J=10Hz, 3H), 4.50 (m, 1H), 5.09 (m, 2H).

B. morpholinomethylphosphinicoPheNle

The above material was deprotected as described in Example 100 to afford 0.10 g crude material. NMR (300 MHz, DMSO-d$_6$) delta 3.26 (d, J=10Hz, 3H), 3.96 (m, 1H).

C. morpholinomethylphosphinicoPheNlenor-C-Sta i-propyl ester

The product of Example 103B (0.10 g) was coupled to 58 mg HCl-nor-C-StaOiPr using the DEC procedure (Example 58). Chromatography (19:1 CH$_2$Cl$_2$:EtOH) afford 28mg pure material. NMR (300MHz, CDCl$_3$) delta 3.61 (d, J=11Hz, 3H), 4.44 (m, 1H), 4.43 (m, 1H), 4.99 (m, 1H).

EXAMPLE 104

ThiomorpholinocarbonylPheNlenor-C-Sta i-propyl ester (I, Z=thiomorpholinocarbonylamino; Q=H; M=phenyl; X=cyclohexyl; W=CH⦀OH; Z$^1$=CO$_2$CH(CH$_3$)$_2$)

A. thiomorpholinocarbonylPhe benzyl ester

To a solution of 1.0 g PheOBn-isocyanate in 10 mL CH$_2$Cl$_2$ at 0° was added 0.85 g thiomorpholine and the resulting solution was stirred at RT for 1.5 hours. The solution was diluted with 50 mL EtOAc and washed 2×25 mL 0.1N HCl. The organic phase was dried over MgSO$_4$, filtered and concentrated to afford 1.26 g crude product which was used without further purification. NMR (300 MHz, CDCl$_3$) delta 4.83 (m, 2H), 5.15 (AB, 2H).

B. thiomorpholinocarbonylPhe

A mixture of 1.26 g of the above material and 4.5 g K$_2$CO$_3$ in 15 mL H$_2$O and 70 mL MeOH was stirred at RT for 60 hours and then heated to reflux for 16 hours. The mixture was concentrated to an aqueous solution and was washed 2×50 mL ether. The aqueous phase was acidified and extracted 3×50 mL CHCl$_2$. The combined extracts were dried over MgSO$_4$, filtered and concentrated. NMR (300 MHz, DMSO-d$_6$) delta 3.01 (m, 2H), 4.26 (m, 1H).

C. thiomorpholinocarbonylPheNle benzyl ester

The product of Example 104B (0.72 g) was coupled to 0.75 g NleOBn using the standard DEC reaction (Example 58) to afford 1.1 g crude product which was used without further purification. NMR (300 MHz, CDCl$_3$) delta 4.47 (m, 1H), 4.58 (m, 1H), 5.12 (m, 2H).

D. thiomorpholinocarbonylPheNle

The product of Example 104C (1.1 g) was deprotected as described for Example 104B above. This afforded 0.70 g crude product which was carried on. NMR (300 MHz, DMSO-d$_6$) delta 3.59 (m, 4H), 4.46 (m, 1H), 4.73 (m, 1H).

E. thiomorpholinocarbonylPheNlenor-C-Sta i-propyl ester

The product of Example 104D (0.70 g) was coupled to 0.50 g HCl-nor-C-StaOiPr using the DEC reaction (Example 58) and the crude material was chromatographed (29:1 CH$_2$Cl$_2$:EtOH) to afford 0.65 g pure product. NMR (300 MHz, CDCl$_3$) delta 4.28 (m, 1H), 4.43 (m, 1H), 4.57 (m, 1H), 5.00 (m, 1H).

EXAMPLE 105

1-OxothiomorpholinocarbonylPheNlenor-C-Sta i-propyl ester (I, Z=thiomorpholinocarbonylaminosulfoxide; M=phenyl; Q=H; R$_2$=n-butyl; X=cyclohexyl; W=CH⫼OH; Z$^1$=CO$_2$CH(CH$_3$)$_2$)

To a solution of 0.10 g of the product of Example 104E in 5 mL CH$_2$Cl$_2$ at 0° was added 35 mg mCPBA and the resulting solution was stirred for 15 minutes. The solution was diluted with 20 mL EtOAc and washed 2×20 mL 10% Na$_2$SO$_3$ and 20 mL 0.1N NaOH. The organic phase was dried over MgSO$_4$, filtered and concentrated and the residue was chromatographed (9:1 CH$_2$Cl$_2$:EtOH) to afford 82 mg pure product. NMR (300 MHz, CDCl$_3$) delta 4.29 (m, 1H), 3.38 (m, 1H), 4.59 (m, 1H), 4.94 (m, 1H).

EXAMPLE 106

1,1-DioxothiomorpholinocarbonylPheNlenor-C-Sta i-propyl ester (I, Z=thiomorpholinocarbonylaminosulfone; M=phenyl; Q=H; R$_2$=n-butyl; X=cyclohexyl; W=CH⫼OH; and Z$^1$=CO$_2$CH(CH$_3$)$_2$)

A. 1,1-dioxothiomorpholinocarbonylPhe benzyl ester

To a solution of 0.64 g of the product of Example 104A in 20 mL CH$_2$Cl$_2$ at 0° was added 1.0 g mCPBA and the resulting solution was stirred for 16 hours. The solution was diluted with 100 mL EtOAc and was washed 3×50 mL 10% Na$_2$SO$_3$. The organic phase was dried over MgSO$_4$, filtered and concentrated. The crude material was chromatographed (1:1 EtOAc-Hex) to afford 0.47 g pure product. NMR (300 MHz, CDCl$_3$) delta 4.79 (m, 1H), 5.16 (AB, 2H).

B. 1,1-dioxothiomorpholinocarbonylPhe

The product of Example 106A (0.47 g) was deprotected as described in Example 100 to afford 0.30 g crude acid which was used without further purification. NMR (300 MHz, DMSO-d$_6$) delta 4.05 (m, 1H), 4.60 (m, 1H), 5.15 (AB, 2H).

C. 1,1-dioxothiomorpholinocarbonylPheNle benzyl ester

The product of Example 106B (0.30 g) was coupled to 0.29 g NleOBn using the DEC reaction described in Example 58 to afford 0.46 g crude product which was used without further purification. NMR (300 MHz, CDCl$_3$) delta 4.50 (m, 2H), 5.12 (AB, 2H).

D. 1,1-dioxothiomorpholinocarbonylPheNle

The product of Example 106C (0.46 g) was deprotected as described in Example 100 to afford 0.36 g crude acid which was used without further purification. NMR (300 MHz, DMSO-d$_6$) delta 3.97 (m, 1H), 4.32 (m, 1H).

E. 1,1-dioxothiomorpholinocarbonylPheNlenor-C-Sta i-propyl ester

The product of Example 106D (0.26 g) was coupled to 0.18 g HCl-nor-C-StaOiPr using DEC (Example 58) to afford 0.31 g pure product after purification by chromatography (19:1 CH$_2$Cl$_2$:EtOH). NMR (300 MHz, CDCl$_3$) delta 4.28 (m, 1H), 4.47 (m, 1H), 4.60 (m, 1H), 5.02 (m, 1H).

EXAMPLE 107

MorpholinocarbonylPheS-MeCysnor-C-Sta benzyl ester (I, Z=morpholinocarbonylamino; M=phenyl; Q=H; R$_2$=CH$_3$SCH$_2$—; X=cyclohexyl; W=CH⫼OH; and Z$^1$=CO$_2$CH$_2$C$_6$H$_5$)

A. Bocnor-C-Sta benzyl ester

Bocnor-C-Sta (0.10 g) was esterified with 0.11 g benzyl alcohol using the standard DEC reaction (Example 58) with 0.25 eq. DMAP. The crude material was chromatographed (39:1 CH$_2$Cl$_2$:MeOH) to afford 0.10 g pure ester. NMR (300 MHz, CDCl$_3$) delta 1.39 (s, 9H), 4.10 (s, 1H), 4.13 (s, 1H), 5.14 (AB, 2H).

B. nor-C-Sta benzyl ester hydrochloride

The product of Example 107A (0.10 g) was deprotected as described in Example 63 to afford 96 mg crude salt which was used without further purification. NMR (300 MHz, DMSO-d$_6$) delta 4.16 (m, 1H), 5.12 (m, 2H).

C. morpholinocarbonylPheS-MeCysnor-C-Sta benzyl ester

The product of Example 107B (0.12 g) was coupled to 84 mg HCl-nor-C-StaOBn using the standard DEC reaction (Example 58). The crude material was chromatographed (19:1 CH$_2$Cl$_2$:MeOH) to afford 92 mg pure product. NMR (300 MHz, CDCl$_3$) delta 2.08 (s, 3H), 4.40 (m, 3H), 5.14 (AB, 2H).

EXAMPLE 108

MorpholinocarbonylPheS-MeCysnor-C-Sta cyclohexylmethyl ester (I, Z=morpholinocarbonylamino; M=phenyl; Q=H; $R_2$=$CH_3SCH_2$—; X=cyclohexyl; W=CH‖‖‖‖‖OH; and $Z^1$=$CO_2CH_2C_6H_{11}$)

A. Bocnor-C-Sta cyclohexylmethyl ester

Bocnor-C-Sta (70 mg) was esterified with 80 mg cyclohexylmethanol as described in Example 107 to afford 40 mg pure material after chromatography (39:1 $CH_2Cl_2$:MeOH). NMR (300 MHz, $CDCl_3$) delta 1.35 (s, 9H), 3.39 (d, J=6Hz, 1H), 4.08 (m, 1H).

B. nor-C-Sta cyclohexylmethyl ester hydrochloride

The product of Example 108A (40 mg) was deprotected as described in Example 63 to afford 37 mg crude salt. NMR (300 MHz, DMSO-$d_6$) delta 3.53 (s, 1H), 4.10 (m, 1H).

C. morpholinocarbonylPheS-MeCysnor-C-Sta cyclohexylmethyl ester

MorpholinocarbonylPheS-MeCys (42 mg) was coupled to 34 mg of the product of Example 108B using the DEC reaction (Example 58). Chromatography (19:1 $CH_2Cl_2$:MeOH) afforded 50 mg pure product. NMR (300 MHz, $CDCl_3$) delta 2.12 (s, 3H), 4.42 (m, 3H).

EXAMPLE 109

2-(Morpholinocarbonyloxy)-3-phenylpropionylNlenorC-Sta i-propyl ester (I, Z=morpholinocarbonyloxy; M=phenyl; Q=H; $R_2$=n-butyl; X=cyclohexyl; W=CH‖‖‖‖‖OH; and $Z^1$=$CO_2CH(CH_3)_2$)

A. 2-(morpholinocarbonyloxy)-3-phenylpropionic acid methyl ester

To a solution of 0.74 g methyl phenyllactate in 10 mL $CH_2Cl_2$ was added 0.60 g morpholinecarbonyl chloride and 1.1 g DMAP, and the resulting solution was stirred at RT overnight. An additional 0.60 g morpholinecarbonyl chloride was added and stirring was continued for 2 days. The mixture was poured into 100 mL $H_2O$ and was extracted 2×100 mL EtOAc. The combined extracts were washed with 20 mL 0.1N HCl and 20 mL 0.1N NaOH, and were dried over $MgSO_4$, filtered and concentrated to afford 1.24 g crude product. NMR (300 MHz, $CDCl_3$) delta 3.75 (s, 3H), 5.19 (m, 1H).

B. 2-(morpholinocarbonyloxy)-3-phenylpropionic acid

The product of Example 109A (1.2 g) was deprotected as described in Example 55 to afford 1.1 g crude acid. NMR (300 MHz, DMSO-$d_6$) delta 4.22 (m, 1H).

C. 2-(morpholinocarbonyloxy)-3-phenylpropionylNle benzyl ester

The product of Example 109B (0.12 g) was coupled to 0.12 g NleOBn using DEC as described in Example 58. This afforded 0.20 g crude product which was carried on. NMR (300 MHz, CDC13) delta 4.59 (m, 1H), 5.14 (AB, 2H), 5.37 (m, 1H).

D. 2-(morpholinocarboxyloxy)-3-phenylpropionylNle

The product of Example 109C (0.20 g) was deprotected as described in Example 100 to afford 0.16 g crude acid which was carried on. NMR (300 MHz, DMSO-$d_6$) delta 4.15 (m, 1H), 5.09 (m, 1H).

E. 2-(morpholinocarbonyloxy)-3-phenylpropionylNle nor-C-Sta i-propyl ester

The product of Example 109D (0.15 g) was coupled to 0.11 g HCL-nor-C-StaOiPr using the DEC procedure described in Example 58. The crude material was chromatographed (19:1 $CH_2Cl_2$:MeOH) to afford 0.16 g pure product. NMR (300 MHz, $CDCl_3$) delta 4.22 (m, 1H), 4 41 (m, 1H), 5.02 (m, 1H), 5.28 (m, 1H).

EXAMPLE 110

0-Acetyl morpholinocarbonylPheS-MeCysnor-C-Sta i-propyl ester (I, Z=morpholinocarbonylamino; M=phenyl; Q=H; $R_2$=$CH_3SCH_2$—; W=CH‖‖‖‖‖OCOCH_3; X=cyclohexyl; and $Z^1$=$CO_2CH(CH_3)_2$)

To a solution of 0.10 g of the product of Example 17 in 1 mL pyridine was added 26 mg $Ac_2O$ and the resulting solution was stirred at RT overnight. The solution was diluted with 100 mL EtOAc and was washed 2×10 mL 0.1N HCl and 2×10 mL 0.1N NaOH. The organic phase was dried over $MgSO_4$, filtered and concentrated. The crude material was chromatographed (19:1 $CH_2Cl_2$:MeOH) to afford 90 mg pure product. NMR (300 MHz, $CDCl_3$) delta 2.16 (s, 6H), 4.37 (m, 1H), 4.52 (m, 2H), 4.88 (d, J=3Hz, 1H), 4.96 (m, 1H).

EXAMPLE 111

MethylaminocarbonylPheNlenor-C-Sta i-propyl ester (I, Z=$CH_3NHCONH$; M=phenyl; Q=H; $R_2$=n-butyl; X=cyclohexyl; W=CH‖‖‖‖‖OH; and $Z^1$=$CO_2CH(CH_3)_2$

A. methylaminocarbonylPhe benzyl ester

To a solution of 0.30 g PheOBn-isocyanate in 20 mL $CH_2Cl_2$ was added 0.51 mL of a 2.3M $MeNH_2$ solution in benzene and the resulting solution was stirred for 4 hours. The solution was diluted with 200 mL EtOAc, and was washed with 20 mL 0.1N HCl and 20 mL 0.1N NaOH. The organic phase was dried over $MgSO_4$, filtered and concentrated to afford 0.30 g crude product which was carried on. NMR (300 MHz, $CDCl_3$) delta 2.69 (d, J=5Hz, 3H), 4.42 (m, 1H), 4.83 (m, 2H).

B. methylaminocarbonylPhe

The product of Example 111A (0.30 g) was deprotected as described in Example 100 to afford 0.23 g crude acid which was used without further purification. NMR (300 MHz, DMSO-$d_6$) delta 2.62 (s, 3H), 4.33 (m, 1H).

C. methylaminocarbonylPheNle benzyl ester

The product of Example 111B (0.23 g) was coupled to NleOBn using the standard DEc reaction (Example 58) to afford 0.38 g crude material which was carried on without purification. NMR (300 MHz, $CDCl_3$) delta 2.51 (br, 3H), 4.29 (m, 1H), 4.46 (m, 1H), 5.14 (s, 2H).

D. methylaminocarbonylPheNle

The product of Example 111C (0.37 g) was deprotected as described in Example 100 to afford 0.29 g crude acid which was used without purification. NMR (300 MHz, DMSO-$d_6$) delta 2.52 (d, J=5Hz, 3H), 4.17 (m, 1H), 4.46 (m, 1H).

E. methylaminocarbonylPheNlenor-C-Sta i-propyl ester

The product of Example lllD (0.15 g) was coupled to 0.13 g HCl-nor-C-StaOiPr using the standard DEC reaction (Example 58) to afford 0.13 g pure product after chromatography (9:1 $CH_2Cl_2$:MeOH). NMR (300 MHz, $CDCl_3$) delta 2.77 (d, J=5Hz, 3H), 4.34 (m, 2H), 4.47 (m, 1H), 4.74 (m, 1H), 5.01 (m, 1H).

EXAMPLE 112

MorpholinocarbonylThalaS-MeCysnor-C-Sta i-propyl ester (I, Z=morpholinocarbonylamino; M=2-thienyl; Q=H; $R_2$=$CH_3SCH_2$—; X=cyclohexyl; W=CHIIIIIIIIOH; and $Z^1$=$CO_2CH(CH_3)_2$)

A. morpholinocarbonylThala

To a solution of 100 mg of 2-thienylalanine in 15 ml of dioxane:water (2:1; v:v) and adjusted to pH 11 with sodium hydroxide was added 96 mg of morpholinosulfonyl chloride and the reaction mixture allowed to stir overnight at room temperature. The pH was again adjusted to 11 and 40 mg of additional sulfonyl chloride added. After stirring for two hours the aqueous solution was extracted with methylene chloride, the pH adjusted to about 2 and extracted with ethyl acetate. The organic phase was separated, washed with brine and dried ($Na_2SO_4$). The solvent was removed to give 66 mg of the intermediate.

B. morpholinocarbonylThalaS-MeCysnor-C-Sta i-propyl ester

Following the general procedure of Example 55, 100 mg of the product of 92B, 66 mg of the product of Example 112A, 48 mg of DCC, 32 mg of HBT and 20 mg of N-methylmorpholine gave 168 mg of crude product. Chromatographing on silica gel gave 59 mg of pure product. NMR (300 Hz, $CDCl_3$) delta 1.13 (m, 6H), 2.05 (s, 3H), 3.0–3.4 (4H, m), 3.5–3.65 (4H, m) and 6.85–7.15 (m, 3H).

EXAMPLE 113

MorpholinocarbonylNphalaS-MeCysnor-C-Sta i-propyl ester (I, Z=morpholinocarbonylamino; M=1-napthyl; Q=H; $R_2$=$CH_3SCH_2$—; X=cyclohexyl; W=CHIIIIIIIOH; and $Z^1$=$CO_2CH(CH_3)_2$)

A. morpholinocarbonylNphala

Using the general procedure of Example 112A, 420 mg of morpholinosulfonylchloride, 500 mg of 1-naphthylalanine, 3 ml 1N sodium hydroxide and 200 mg sodium bicarbonate in 5 ml of 1:1 tetrahydrofuran water gave 120 mg of the desired intermediate.

B. morpholinocarbonylNphalaS-MeCysnor-C-Sta i-propyl ester

Employing the usual coupling procedure, 145 mg of the product of Example 93B, 131 mg of the above product, 82 mg DCC, 55 mg of HBT and 45 ul of N-methylmorpholine in 15 ml of methylene chloride gave 253 mg of product which was chromatographed on silica gel using 1–1.5% methanol in chloroform, 83 mg. NMR (300 Hz, $CDCl_3$) delta 1.2 (d, J=5Hz, 6H), 2.01 (s, 3H), 3.05 (m, 2H), 3.41 (m, 2H) and 6.75–8.18 (7H, m).

EXAMPLE 114

MorpholinocarbonylPheS-MeCysnor-C-Sta methyl ester (I, Z=morpholinocarbonylamino; M=phenyl; $R_2$=$CH_3SCH_2$—; Q=H; X=cyclohexyl; W=CHIIIIIIIOH; and $Z^1$=$CO_2CH_3$ Following the usual coupling step procedure, 135 mg of S-MeCysnor-C-Sta methyl ester hydrochloride, 88.2 mg of morpholinocarbonylPhe, 32.1 mg of N-methylmorpholine, 42.9 mg HBT and 65.4 mg of DCC in 20 ml of methylene chloride gave mg of product. Chromatographing on silica gel using chloroform-methanol (99:1; v:v) gave 103 mg of pure product, identical to that prepared in Example 58. NMR (300 Hz, $CDCl_3$) delta 2.1 (s, 3H), 3.7 (s, 3H), 3.0–3.4 (m, 4H), 3.5–3.85 (m, 4H) and 7.3 (s, 5H).

EXAMPLE 115

MorpholinocarbonylPheS-MeCysnor-C-Sta N-methyl amide (I, Z=morpholinocarbonylamino; Q=H; M=phenyl; $R_2$=$CH_3SCH_2$—; X=cyclohexyl; W=CHIIIIIIIOH; and $Z^1$=$CONHCH_3$ The product of Example 114 (45 mg) dissolved in 10 ml of methanol was treated with methyl amine until saturated and the reaction mixture stored at room temperature overnight. The solvent was removed and the residue triturated with diethyl ether, 30 mg. The product was identical to that in Example 86. NMR (300 Hz, $CDCl_3$) delta 2.1 (s, 3H), 2.65 (3H, s), 2.85 (d, J=5Hz, 2H) and 7.2 (s, 5H).

EXAMPLE 116

MorpholinocarbonylPheS-MeCysnor-C-Sta N-trifluoroethyl amide (I, Z=morpholinocarbonylamino; M=phenyl; Q=H; $R_2$=$CH_3SCH_2$—; X=cyclohexyl; W=CHIIIIIIIOH; $Z^1$=$CONHCH_2CF_3$)

A. Bocnor-C-Sta N-trifluoroethylamide

Employing the general coupling procedure, 33 mg of trifluoroethylamine by hydrochloride, 75.3 mg of Bocnor-C-Sta, 25 mg of N-methylmorpholine, 33 mg HBT and 51.5 mg of DCC in 20 mL of methylene chloride gave 121 mg of the desired intermediate as a foam.

B. nor-C-Sta N-trifluoroethylamide hydrochloride

The product of Example 116A was deblocked using HCl -dioxane (5 mL) at room temperature for 90 minutes. Removal of the solvent gave 87 g of product.

C. BocS-MeCysnor-C-Sta N-trifluoroethylamide

Using the general coupling procedure, 87 mg of the product of Example 116B, 58.8 mg of BocS-MeCys, 25.3 mg N-methylmorpholine, 33.8 mg HBT and 51.5 mg of DCC in 20 mL of methylene chloride gave 146 mg of the desired intermediate.

D. S-MeCysnor-C-Sta N-trifluoroethyl amide hydrochloride

The product of Example 116C (146 mg) was deblocked using 5 mL of dioxane saturated with HCl for 90 minutes at room temperature. Removal of the solvent gave 121 mg of product.

E. morpholinocarbonylPheS-MeCysnor-C-Sta N-trifluoroethyl amide

Again, using the coupling procedure, 121 mg of the product Example 116D, 69.5 mg morpholinocarbonyl-Phe, 25.3 mg N-methylmorpholine, 33.8 HBT and 51.5 mg DCC in 20 ml of methylene chloride gave 123 mg of product. Chromatographing on silica gel using chloroform-methanol (99:1; v:v) gave 57 mg of pure product. NMR (300 Hz, CDCl$_3$) delta 3.1–3.5 (m, 4H), 3.5–3.8 (m, 4H) and 7.3 (s, 5H).

EXAMPLE 117

(2-Methoxycarbonylpyrrolid-1-yl)carbonylPheSMe-Cysnor-C-Sta i-propyl ester (I, Z=1-(2-methoxycarbonylpyrrolidyl)carbonylamino; M=phenyl; Q=H; R$_2$=CH$_3$SCH$_2$—; X=cyclohexyl; W=CH||||||||OH; and Z$^1$=COCH(CH$_3$)$_2$)

A. (2-methoxycarbonylpyrrolid-1-yl)carbonylPhe benzyl ester

A solution of 66 mg of proline methyl ester hydrochloride in 10 mL of CH$_2$Cl$_2$ and 70 ul of N,N-diisopropylethylamine was treated with 112 mg of 1-benzyloxycarbonyl-2-phenethyl isocyanate at 0° C. and the reaction stirred overnight. Work-up yielded 153 mg of the desired intermediate.

B. (2-methoxycarbonylpyrrolid-1-yl)carboxylPhe

Using the procedure of Example 18B, the product of Example 117A was debenzylated to give 170 mg of intermediate.

C. (2-methoxycarbonylpyrrolid-1-yl)carbonylPhe S-MeCysnor-C-Sta i-propyl ester Using the usual coupling procedure, the product of Example 92B (174 mg), the above intermediate (140 mg), 82 mg of DCC, 55 mg of HBt and 45 ul of N-methylmorpholine in 10 mL of CH$_2$Cl$_2$ gave 230 mg of crude product. Chromatographing on silica gel using 1–1.5% methanol in chloroform gave 102 g of product. NMR (300 Mz, CDCl$_3$) delta 1.21 (6H, m), 2.09 (s, 3H), 2.78–2.89 (2H, m), 3.0–3.2 (2H, m), 3.65 (s, 3H) and 7.12–7.32 (m, 5H).

EXAMPLE 118

N-Methyl-N-methoxycarbonylmethylaminocarbonyl-PheS-MeCys nor-C-Sta i-propyl ester (I, Z=CH$_3$OCOCH$_2$N(CH$_3$)CONH; M=phenyl; Q=H; R$_2$=CH$_3$SCH$_2$—; X=cyclohexyl; W=CH||||||||OH; Z$^1$=CO$_2$CH(CH$_3$)$_2$)

A. N-(methoxycarbonylmethyl)-N-methylaminocarbonyl-Phe benzyl ester

A reaction mixture comprising L-phenylalanine benzyl ester (171 mg), 72 mg of N-methyl-N-chlorocarbonylglycine methyl ester and 47 ul of N-methylmorpholine in 15 mL of CH$_2$Cl$_2$ was stirred at 0° C. and then overnight at room temperature. 4-Dimethylaminopyridine (10 mg) was added and stirring continued for 3 hours. Additional carbamyl chloride (40 mg) was added and the reaction stirred for several days. The solvent was removed and the residue chromatographed on silica gel using chloroform. The pure intermediate, 105 mg, was isolated in fractions 22–30.

B. N-(methoxycarbonylmethyl)-N-methylaminocarbonyl-Phe

The product of Example 118A was debenzylated following the general procedure of Example 18B to give 129 mg of crude intermediate.

C. N-methyl-N-methoxycarbonylmethylamincarbonylPhe S-MeCysnor-C-Sta i-propyl ester Using the previously described coupling procedure, 155 mg of the product of Example 92B, 115 mg of the above product, 81 mg of DCC, 53 mg of HBT and 43 ul of N-methylmorpholine in 10 mL of CH$_2$Cl$_2$ gave 251 mg of product. Chromatographing on silica gel using 1–2% methanol in chloroform gave 70 mg of the desired product NMR (300 Hz, CDCl$_3$) delta 1.23 (m, 6H), 2.03 (s, 3H), 2.9 (s, 3H), 3.65 (s, 3H) and 7.1–7.28 (m, 5H).

EXAMPLE 119

N-Methyl-N-methoxycarbonylmethylaminocarbonyl-PheNlenor-C-Sta i-propyl ester (I, Z=CH$_3$OCOCH$_2$N(CH$_3$)CONH; M=phenyl; Q=H; R$_2$=n-butyl; X=cyclohexyl; W=CH||||||||OH; and Z$^1$=CO$_2$CH(CH$_3$)$_2$)

A. NIenor-C-Sta hydrochloride

Using the usual coupling procedure, BocNle (78 mg), nor-C-Sta i-propyl ester hydrochloride, 69 mg DCC, 45 mg HBT and 37 ul of N-methylmorpholine in 10 mL of CH$_2$Cl$_2$ gave 171 mg of product.

The Boc was removed from the product by treatment with 10 mL of dioxane saturated with HCl for 3 hours. Workup gave 155 mg of the named product.

B. N-methyl-N-methoxycarbonylmethylaminocarbonyl-PheNlenor-C-Sta i-propyl ester Again, employing the usual coupling procedure, 101 mg of the product of Example 118B, 155 mg of the above product, 70 mg of DCC, 46 mg of HBT and 37 ul of N-methylmorpholine gave 209 of product which was purified by chromatographing on silica gel using 0.5–1% methanol in chloroform as the eluent, 51 mg. NMR (300 Hz, CDCl$_3$) delta 0.85 (t, J=5Hz, 3H), 1.12 (m, 6H), 2.77 (s, 3H), 3.09–3.19 (m, 2H), 3.62 (s, 3H) and 7.1–7.29.

MorpholinocarbonylPheNlenor-C-Sta N-2-methylbutyl amide (I, Z=morpholinocarbonylamino; M=phenyl; Q=H; R$_2$=n-butyl; X=cyclohexyl; W=CH||||||||OH; and Z$^1$=CONHCH$_2$CH(CH$_3$)C$_2$H$_5$)

A. nor-C-Sta N-2-methylbutylamide hydrochloride

Starting with 80.6 mg of Boc nor-C-Sta and 22.3 mg of 2-methylbutylamine and using the DCC coupling procedure of Example 64A followed by the deblocking procedure of Example 64B gave 87 mg of the named product.

B. morpholinocarbonylPheNlenor-C-Sta N2-methylbutylamide

MorpholinocarbonylPheNle (100 mg) was coupled to nor-C-Sta N-2-methylbutylamide using the DCC procedure of Example 55. The crude material was chromatographed on silica gel (99:1 CHCl₃:methanol) and after 80×4 ml fractions (97.5:2.5) to give 80 mg of the desired product. NMR (300 Hz, CDCl₃) delta 0.8–1.05 (m, 6H), 2.5 (d, J=5Hz, 2H), 3.0–3.4 (m, 4H), 3.4–3.84 (m, 4H), 5.35 (d, J=5Hz, 1H) and 7.3 (s, 5H).

EXAMPLE 121

MorpholinocarbonylPheS-MeCysnor-C-Sta N-2,2-dimethyl-3-dimethylaminopropyl amide (I, Z=morpholinocarbonylamino; M=phenyl; Q=H; R₂=CH₃SCH₂—; X=cyclohexyl; W=CHIIIIIIIIIOH; and Z¹=CONHCH₂C(CH₃)₂CH₂N(CH₃)₂)

A. nor-C-Sta N-2,2-dimethyl-3-dimethylaminopropyl amide hydrochloride

Starting with 50 mg of Boc nor-C-Sta and 22 mg of N,N,2,2-tetramethyl-1,3-propandimine and using the DCC coupling procedure of Example 64A followed by the deblocking procedure of Example 64B gave 98 mg of the desired intermediate.

B. S-MeCysnor-C-Sta 2,2-dimethyl-3-dimethylaminopropyl amide hydrochloride

Using 98 mg of the product of Example 121A and 60 mg of Boc S-MeCys and following the DCC coupling procedure followed by the Boc deblocking procedure gave 120 mg of product.

C. morpholinocarbonylPheS-MeCysnor-C-Sta 2,2-dimethyl-3-dimethylaminopropyl amide The product of Example 121B (120 mg) and morpholinocarbonylPhe (66 mg) were coupled using the DCC procedure of Example 55 to give 116 mg. NMR (300 Hz, CDCl₃+CH₃OD) delta 0.81 (s, 6H), 1.15 (s, 6H), 2.0 (s, 3H), 3.1–3.4 (m, 4H), 3.4–3.64 (m, 4H) and 7.06–7.15 (m, 5H).

EXAMPLE 122

MorpholinocarbonylPheS-MeCysnor-C-Sta N-2-picolyl amide (I, Z=morpholinocarbonylamino; M=phenyl; Q=H; R₂=CH₃SCH₂—; X=cyclohexyl; W=CHIIIIIIIOH; and Z¹=CONHCH₂C₅H₄N)

A. nor-C-Sta N-2-picolyl amide dihydrochloride

Using the coupling procedure of Example 64A 60.2 mg of Boc nor-C-Sta and 21.6 mg of 2-aminomethylpyridine gave 108 mg of Bocnor-C-Sta N-2-picolyl amide, which was deblocked using the procedure of Example 64B to give 83 mg of the named intermediate.

B. S-MeCysnor-C-Sta N-2-picolyl amide dihydrochloride

BocS-MeCys (47 mg) was coupled with 83 mg of the above product using the DCC procedure of Example 55 to give 126 mg of product, which was deblocked with hydrogen chloride in dioxane to give 78 mg of the named product

C. morpholinocarbonylPheS-MeCysnor-C-Sta N-2-picolyl amide

Again, using the DCC coupling procedure of Example 55, 78 mg of the product of Example 122B and 44.9 mg of morpholinocarbonylPhe gave 113 mg of the product which was chromatographed on silica gel using chloroform-methanol from 99:1 to 95:5 as the eluent, 22 mg. NMR (300 Hz, CDCl₃) delta 2.05 (s, 3H), 2.85 (J=5Hz, 2H), 3.0–3.4 (m, 4H), 3.4–3.7 (m, 4H) and 7.0–7.9 (m, 9H).

EXAMPLE 123

3-Hydroxypyrid-2-ylcarbonylPhe S-MeCysnor-C-Sta i-propyl ester (I, Z=3-hydroxypyrid-2-ylcarbonylamino; M=phenyl; Q=H; R₂=CH₃SCH₂—; X cyclohexyl; W=CHIIIIIIIIOH; and Z¹=CO₂CH(CH₃)₂)

According to the procedure for the preparation and purification of the product of Example 38B, except that 34 uL, 1.2 equivalent of triethylamine was used to neutralize the amine hydrochloride, 110 mg of the product of Example 39 and 28 mg of 3-hydroxypicolinic acid gave 78 mg of colorless powder, TLC Rf 0.42 in 2:1 ethyl acetate-hexane.

1H NMR, CDCl₃, 250 MHz, partial, delta ppm: 1.26 and 1.27 (d, 3H ea), 2.11 (s, 3H), 2.60 and 2.85 (dd, 1H ea), 3.26 (m, 3H), 4.09, 4.37, 4.45, 4.79 and 5.03 (m, 1H ea), 6.5, 6.81 and 8.49 (d, 1H ea), 8.08 (m, 1H).

EXAMPLE 124

MorpholinocarbonylPheNlenor-C-Sta cyclohexylmethyl ketone (I, Z=morpholinocarbonylamino; M=phenyl; Q=H; R₂=n-butyl; X=cyclohexyl; W=CHIIIIIIIOH; and Z¹=—COCH₂C₆H₁₁) A. (S)-4-t-butoxycarbonylamino-3(R)-benzyloxy

A. (S)-4-t-butoxycarbonylamino-3-(R)-benzyloxy1,5-dicyclohexyl-2-butanone

To a solution of cyclohexylmethylmagnesium bromide (from 0.78 mL cyclohexylmethyl bromide and 0.14 g magnesium in 3 mL ether) was treated with 1.00 g 3(S)-t-butoxycarbonylamino-2(R)-benzyloxy-4-cyclohexylbutyraldehyde (product of Example 5A, U.S. Pat. No. 4,668,769) in 6 mL ether at 5° C. over 2–3 minutes. After 25 minutes the mixture was treated with aqueous ammonium chloride, extracted with ether and washed with 1N HCl, aqueous bicarbonate, dried, concentrated and purified on silica eluting with ethyl acetate/hexanes giving 278 mg of a mixture of the two alcohol isomers, TLC Rf's 0.48 and 0.41 in 1:3 ethyl acetate/hexanes. This product was dissolved in 5 mL 1:2 ether-acetone and treated at 0° C. with 1 mL chromic acid solution (Org. Syn. Coll. Vol. V, p. 310). After 15 minutes the mixture was diluted with ether and washed with aqueous NaOH, dried and chromatographed on silica in ethyl acetate/hexanes giving 201 mg of yellow oil, TLC Rf 0.59 in 1:3 ethyl acetate-hexanes.

B. 4(S)-amino-3(R)-benzyloxy-1,5-dicyclohexyl-2-butanone hydrochloride

The product of Example 124A (195 mg) was dissolved in 2 mL 4N HCl-dioxane and stirred at 25° C. for 1 hour, concentrated, and dried, giving 165 mg of colorless powder, TLC Rf 0.56 in System C (spotted plate exposed to NH₃ prior to elution).

C. morpholinocarbonylPheNlenor-C-Sta cyclohexylmethyl ketone benzyl ester

According to the general procedure for preparation of the product of Example 38B, except that 1.3 equivalent triethylamine was used to neutralize the amine salt, 158 mg of the product of Example 124B and 152 mg of the product of Example 7C gave after purification on silica in ethyl acetate-hexanes 228 mg of colorless foam, TLC Rf 0.29 in 2:1 System A.

D. morpholinocarbonylPheNlenor-C-Sta cyclohexylmethyl ketone

The product of Example 124C (220 mg) was dissolved in 20 mL of 1:1 methanol-acetic acid and shaken with 250 mg 10% Pd/C for 22 hours at 25° C. and 50 p.s.i. hydrogen, filtered through Supercel, concentrated, coevaporated with added toluene and ether, and dried giving 179 mg of amber foam which was chromatographed on silica in ethyl acetate-hexanes giving 131 mg colorless powder, TLC Rf 0.44 in ethyl acetate.

1H NMR, CDCl$_3$, 250 MHz, partial, delta ppm: 0.87 (t, 3H), 2.40, 2.53, 3.05 and 3.12 (dd, 1H ea), 3.28 (m), 3.62 (m, 4H), 4.07 (br, 1H), 4.15 (m, 1H), 4.52 (m, 2H), 5.00, 6.23 and 6.51 (d, 1H ea).

EXAMPLE 125

4-OxopiperidinocarbonylPheS-MeCysnor-C-Sta i-propyl ester ethylene ketal (I, Z=4-oxopiperidinocarbonylamino ethylene ketal; M=phenyl; Q=H;

R$_2$=CH$_3$SCH$_2$—; X=cyclohexyl; W=CH‖‖‖‖‖OH; and Z$^1$=CO$_2$CH(CH$_3$)$_2$)

According to the procedure for preparation and purification of the product of Example 50, 150 mg of the product of Example 39 and 32 uL of 4-piperidone ethylene ketal gave 60 mg of colorless powder, TLC Rf 0.30 in ethyl acetate, HPLC 2.76 and 3.09 minutes (ca. 2:1) in 80/20 acetonitrile-water. The major component was separated by semipreparative reverse-phase HPLC on a 9.8×250 mm Zorbax C-8 column in 70/30 acetonitrile-water, 60 mg of the mixture giving 28 mg of the earlier-eluting compound.

1H NMR, CDCl$_3$, 250 MHz, partial, delta ppm: 0.92 (m), 1.26 and 1.28 (d, 3H ea), 2.09 (s, 3H), 2.72, 2.93, 3.08 and 3.29 (dd, 1H ea), 3.34 (m), 3.92 (s, 4H), 4.10 (br, 1H), 4.35–4.53 (m, 3H), 4.87 (d, 1H), 5.06 (septet, 1H), 6.95 and 7.11 (d, 1H ea), 7.18–7.38 (m, aromatic).

EXAMPLE 126

N-BocPiperid-4-ylcarbonylPheS-MeCysnor-C-Sta i-propyl ester (I, Z=N-Bocpiperid-4-ylcarbonylamino; M=phenyl; Q=H; R$_2$=CH$_3$SCH$_2$—; X=cyclohexyl; W=CH‖‖‖‖‖OH; Z$^1$=CO$_2$CH(CH$_3$)$_2$)

Using the procedure for preparation and purification of the product of Example 38B, except that 1.3 equivalent triethylamine was used to neutralize the amine hydrochloride, 230 mg of the product of Example 39 and 97 mg of N-Boc-isonipecotic acid gave 241 mg of colorless powder, TLC Rf 0.49 in ethyl acetate.

1H NMR, CDCl$_3$, 250 MHz, partial, delta ppm: 1.28 (d, 6H), 1.46 (s, 9H), 2.14 (s, 3H), 2.62, 2.91, 3.05 and 3.16 (dd, 1H ea), 2.70 (m), 3.39, 5.98, 6.53 and 6.75 (d, 1H ea), 4.35 and 4.45 (m, 1H ea), 5.04 (septet, 1H), 7.13–7.37 (m, aromatic).

EXAMPLE 127

Piperid-4-ylcarbonylPhe S-MeCysnor-C-Sta i-propyl ester (I, Z=piperid-4-ylcarbonylamino; M=phenyl; Q=H; R$_2$=CH$_3$SCH$_2$—; X=cyclohexyl; W=CH‖‖‖‖‖OH; and Z$^1$=CO$_2$CH(CH$_3$)$_2$)

The product of Example 126 (175 mg) was dissolved in 4N HCl-dioxane for 30 minutes at 25° C., concentrated and dried giving 157 g of pale yellow powder, TLC Rf 0.20 in System C (the spotted plate was exposed to ammonia prior to elution).

1H NMR, DMSO-d$_6$, 250 MHz, partial, delta ppm: 1.28 and 1.29 (d, 3H ea), 2.09 (s, 3H), 4.00, 4.21 and 4.45 (m, 1H ea), 4.86 (septet, 1H), 5.36, 7.69, 8.15 and 8.30 (d, 1H ea).

EXAMPLE 128

4-OxopiperidinocarbonylPhe S-MeCysnor-C-Sta i-propyl ester (I, Z=4-oxopiperidinocarbonylamino; M=phenyl; Q=H; R$_2$=CH$_3$SCH$_2$—; X=cyclohexyl; W=CH‖‖‖‖‖OH; and Z$^1$=CO$_2$CH(CH$_3$)$_2$)

A. 4-oxopiperidinocarbonylPhe benzyl ester

4-Piperidone hydrochloride (819 mg) was dissolved in 15 mL dichloromethane and treated at 0° C. with 740 uL triethylamine and 1.50 g of the product of Example 7A (isocyanatoPheOBn). After 1.5 hours the mixture was dissolved in ethyl acetate, washed with 1N HCl (3x), aqueous NaHCO$_3$, brine, dried over MgSO$_4$, concentrated, dissolved in 10 mL hot 2:1 ethyl acetate-hexanes, cooled and filtered removed 0.6 g of a solid, TLC Rf 0.53 in 1:1 System A. The mother liquors were chromatographed on silica in 1:1 ethyl acetate-hexanes giving 322 mg of a clear oil, TLC Rf 0.13 in System A, whose NMR spectrum was in accord with the title structure.

B. 4-oxopiperidinocarbonylPhe

The product of Example 128A (297 mg) was dissolved in 15 mL 1:10 acetic acid-methanol and shaken at 25° C. and 50 p.s.i. hydrogen with 150 mg 10% Pd/C for 30 minutes, filtered, concentrated and coevaporated with added toluene giving 227 mg colorless foam, TLC Rf 0.05 in ethyl acetate.

C. 4-oxopiperidinocarbonylPhe S-MeCysnor-C-Sta i-propyl ester

Using the procedure for preparation and purification of the product of Example 38B, except that triethylamine was used to neutralize the amine hydrochloride, 100 mg of S-MeCysnor-C-Sta isopropyl ester hydrochloride (product of Example 48D) and 73 mg of the product of Example 128B gave 116 mg of colorless solid, TLC Rf 0.29 in ethyl acetate.

EXAMPLE 129

CarboxylbutylcarbonylPhe S-MeCysnor-C-Sta i-propyl ester (I, Z=HO$_2$C(CH$_4$CONH—; M=phenyl; Q=H, R$_2$=CH$_3$SCH$_2$; X=cyclohexyl; W=CH‖‖‖‖‖OH; and Z$^1$=CO$_2$CH(CH$_3$)$_2$)

A. (CH$_3$)$_3$CO$_2$C(CH$_2$)$_4$COPhe S-MeCysnor-C-Sta ipropyl ester

Hexanedicarboxylic acid mono tert-butyl ester (0.10 g) was condensed with 0.10 g Phe S-MeCysnor-C-Sta i-propyl ester hydrochloride using DEC as described in Example 58. Chromatography on SiO$_2$ (1 19 MeOH:CH$_2$Cl$_2$) afforded 95 mg pure product. NMR (300 MHz, CDCl$_3$) delta 1.41 (s, 9H), 4.38 (m, 2H), 4.62 (m, 1H), 5.01 (m, 1H).

B. carboxybutylcarbonylPhe S-MeCysnor-C-Sta i-propyl ester

A solution of 90 mg of the above t-butyl ester in 2 mL trifluoroacetic acid and 2 mL CH$_2$Cl$_2$ was stirred at room temperature for 1 hour. After standard acid-base workup, the crude material was purified by chromatography (9:1 CH$_2$Cl$_2$:MeOH) to afford 52 mg pure product. NMR (300 MHz, CDCl$_3$) delta 2.08 (s, 3H), 4.40 (m, 2H), 4.73 (m, 1H), 4.97 (m, 1H).

EXAMPLE 130

AminopentylcarbonylPhe S-MeCysnor-C-Sta i-propyl ester (I, Z=H$_2$N(CH$_2$)$_5$CONH—; M=phenyl; Q=H; R$_2$=CH$_3$SCH$_2$; X=cyclohexyl; W=CH$\text{IIIIIII}$OH; and Z$^1$CO$_2$CH(CH$_3$)$_2$)

A. BocaminopentylcarbonylPhe S-MeCysnor-C-Sta i-propyl ester

N-Boc-6-aminohexanoic acid (59 mg) was coupled to Phe S-MeCysnor-C-Sta i-propylester hydrochloride (133 mg) using the standard DEC reaction (Example 58) to afford 145 mg of crude product which was used without further purification. NMR (300 MHz, CDCl$_3$) delta 1.43 (s, 9H), 2.12 (s, 3H), 4.35 (m, 1H), 4.43 (m, 1H, 4.58 (m, 1H), 4.62 (m, 1H), 5.03 (m, 1H).

C. aminopentylcarbonylPhe S-MeCysnor-C-Sta i-propyl ester

A solution of 140 mg of the product of Example 130A in 3 mL 4N HCl in dioxane was stirred for 45 minutes and concentrated. Acid-base work-up afforded 100 mg pure product. NMR (300 MHz, CDCl$_3$) delta 2.07 (s, 3H), 4.36 (m, 2H), 4.64 (m, 1H), 4.98 (m, 1H).

EXAMPLE 131

MorpholinocarbonylPheAspnor-C-Sta i-propyl ester (I, Z=morpholinocarbonylamino; M=phenyl; Q=H; R$_2$=HO$_2$CCH$_2$; X=cyclohexyl; W= $\text{IIIIII}$OH; and Z$^1$=CO$_2$CH(CH$_3$)$_2$)

A. morpholinocarbonylPhe Asp benzyl ester

Aspartic acid beta-benzyl ester (0.4 g) was treated with morpholinocarbonylPhe hydroxysuccinimide ester as described in Example 80 to afford 0.42 g crude material which was used without further purification. NMR (300 MHz, DMSO-d$_6$) delta 4.34 (m, 1H), 4.61 (m, 1H), 5.10 (s, 2H).

B. morpholinocarbonylPhe Asp(0-benzyl ester)norC-Sta i-propyl ester

The product of Example 131A (.29 g) was coupled to 0.12 g nor-C-Sta i-propyl ester using the standard DEC reaction (Example 76) to afford 0.20 g crude material which was used without further purification. NMR (300MHz, CDCl$_3$) delta 4.39 (m, 2H), 4.65 (m, 1H), 5.02 (m, 1H), 5.09 (AB, 2H).

C. morpholinocarbonylPhe Aspnor-C-Sta i-propyl ester

A solution of 0.20 g of the above crude benzyl ester and 0.4 g 10% Pd on carbon in 30 mL MeOH was hydrogenated at 45 p.s.i. for 30 minutes. The mixture was filtered through Celite and concentrated. The residue was chromatographed (23:1:1 CHCl$_3$:MeOH:AcOH) to afford 81 mg pure product. NMR (300 MHz, DMSO-d$_6$) 4 17 (m, 1H), 4.28 (m, 1H), 4.44 (m, 1H), 4.84 (m, 1H).

EXAMPLE 132

MorpholinocarbonylPhe Asnnor-C-Sta i-propyl ester (I, Z=morpholinocarbonylamino; M=phenyl; Q=H; R$_2$=H$_2$NCOCH$_2$; X=cyclohexyl; W=CH$\text{IIIIIII}$OH; and Z$^1$=CO$_2$CH(CH$_3$)$_2$)

A. morpholinocarbonylPheAsn

Asparagine (0.5 g) was treated with 1.0 g morpholinocarbonylPhe hydroxy succinimide as described in Example 80. The crude material (0.80 g) was used without further purification. NMR (300 MHz, DMSO-d$_6$) delta 4.10 (m, 1H), 3.34 (m, 1H), 4.53 (m, 1H).

B. morpholinocarbonylPhe Asnnor-C-Sta i-propyl ester

The above product (0.18 g) was coupled to 0.10 g nor-C-Sta i-propyl ester using the standard DEC reaction (Example 76) to afford 0.17 g pure product after chromatography (9:1 CH$_2$Cl$_2$:MeOH). NMR (300 MHz, CDCl$_3$) delta 4.39 (m, 2H), 4.62 (m, 1H), 5.01 (m, 1H).

EXAMPLE 133

MorpholinocarbonylPheValnor-C-Sta i-propyl ester (I, Z=morpholinocarbonylamino; M=phenyl; Q=H; R$_2$=CH(CH$_3$)$_2$;X=cyclohexyl; W=CH $\text{IIIIII}$OH; and Z$^1$=CO$_2$CH(CH$_3$)$_2$)

A. morpholinocarbonylPheVal

Valine (0.40 g) was treated with 0.60 g morpholinocarbonylPhe hydroxysuccinimide ester as described in Example 80. The crude material (0.53 g) was used without further purification. NMR (300 MHz, DMSO-d$_6$) delta 0.92 (d, J=7Hz, 3H), 4.18 (m, 1H), 4.43 (m, 1H).

morpholinocarbonylPheValnor-C-Sta i-propyl ester

The above product (0.17 g) was coupled to 0.10 g nor-C-Sta i-propyl ester using the standard DEC reaction (Example 76). The crude material was chromatographed (24:1 CH$_2$Cl$_2$:MeOH) to afford 0.15 g pure product. NMR (300 MHz, CDCl$_3$) delta 0.77 (d, J=6Hz, 3H), 0.84 (d, J=7Hz, 3H), 4.45 (m, 1H), 4.52 (m, 1H), 5.00 (m, 1H).

EXAMPLE 134

IsovalerylPhe Nlenor-C-Sta i-propyl ester (I, Z=(CH$_3$)$_2$CHCH$_2$CONH; M=phenyl; Q=H; R$_2$=n-butyl; X=cyclohexyl; W=CH $\text{IIIIII}$OH; and Z$^1$=CO$_2$CH(CH$_3$)$_2$)

Employing the aforementioned coupling procedure of Example 5B, 107 mg of isovalerylPhe Nle, 72 mg of nor-C-Sta i-propyl ester, 68 mg of HBT and 57 mg of DEC in 1 mL of CH$_2$Cl$_2$ gave, after chromatographing on SiO$_2$ using 1:1 ethyl acetate-hexanes as the eluent, 121 mg of the desired product. NMR (300 MHz, CDCl$_3$), delta 0.9 (m, 9H), 1.22 (d, 6H), 2.93–3.08 (m, 2H), 4.05 (m, 1H), 4.19, 4.40, 4.66 (m, 1H ea), 4.98 (septet, 1H), 6.09, 6.25, 6.52 (d, 1H ea) and 7.1–7.24 (m, 5H).

EXAMPLE 135

MorpholinocarbonylhomoPheNlenor-C-Sta i-propyl ester (I, Z=morpholinocarbonylamino; M=benzyl; R$_2$=n-butyl; Q=H; X=cyclohexyl; Z$^1$=CO$_2$CH(CH$_3$)$_2$; and W=CH$\text{IIIIIIII}$OH)

Using the DCC procedure of Example 55, 138 mg of morpholinocarbonylhomoPheNle, 95 mg of nor-C-Sta i-propyl ester hydrochloride, 70 mg of DCC, 46 mg of HBT and 38 ul of N-methyl morpholine gave, after chromatographing on SiO$_2$ using 1-2% methanol in chloroform, 62 mg of the desired product. NMR (300 MHz, CDCl$_3$) delta 1.2 (d, 5H), 3.2 (m, 2H), 3.5 (m, 2H) and 7.2 (s, 5H).

We claim:

1. A compound of the formula

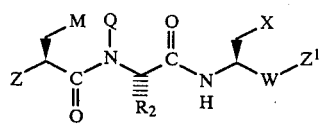

(I)

and a pharmaceutically acceptable salt thereof, wherein Z is R$_1$—(Y)$_m$—(A)$_p$, where R$_1$ is morpholino; Y is C=O; A is N(CH$_3$), NH or O; m and p are each 1; M is phenyl, benzyl, naphthyl, thienyl, methoxyphenyl, hydroxyphenyl, chlorophenyl or (C$_6$-C$_7$)cycloalkyl; Q is methyl or hydrogen; R$_2$ is (C$_1$-C$_5$)alkyl, (C$_1$-C$_3$)alkylthio(C$_1$-C$_2$)alkyl, (C$_1$-C$_3$)alkoxy(C$_1$-C$_2$)alkyl, benzyloxy(C$_1$-C$_2$)alkyl, benzyl hydroxy (C$_1$-C$_2$)alkyl, carboxy,(C$_1$-C$_2$)alkyl, guanido (C$_1$-C$_3$)alkyl, (C$_1$-C$_3$)alkylsulfinyl(C$_1$-C$_2$)alkyl, (C$_1$-C$_3$)alkylsulfonyl(C$_1$-C$_2$)alkyl, 4-benzyloxycarbonylaminobutyl, 4-aminobutyl, imidazol-4-ylmethyl, N-t-butoxycarbonylimidazol-4-ylmethyl or carbamyl(C$_1$-C$_2$)alkyl; X is cyclohexyl, i-propyl or phenyl; W is CH OH; Z$^1$ is CH$_2$OH or R—S—T where R is C=O, S is O, NH, N(CH$_3$), CH$_2$ or a chemical bond linking R and T; and T is (C$_1$-C$_5$)alkyl, hydroxy(C$_1$-C$_4$)alkyl, CONH—(C$_1$-C$_4$)alkyl, hydrogen, trifluoroethyl, (C$_6$-C$_7$)cycloalkyl, (C$_6$-C$_7$)cycloalkylmethyl, phenyl, benzyl, amino(C$_2$-C$_5$)alkyl, O-(C$_1$-C$_2$)alkyl hydroxylamino, morpholino, 4-(C$_1$-C$_2$)alkylpiperazino or omega-di(C$_1$-C$_2$)alkylamino(C$_3$-C$_5$)alkyl with the provisos that when T is CONH—(C$_1$-C$_4$)alkyl, is CH$_2$, NH, N(CH$_3$) or CH$_2$; when T is (C$_2$-C$_5$)alkylamino, O—(C$_1$-C$_2$)alkyl hydroxylamino, morpholino or 4-(C$_1$-C$_2$)alkylpiperazino, S is CH$_2$ or a chemical bond linking R and T; and when R$_1$ is morpholino, Y is C=O, A is NH, m and p are each 1, M is phenyl, R$_2$ is (C$_1$-C$_5$)-alkyl or (C$_1$-C$_3$)alkylthio(C$_1$-C$_2$)alkyl, X is cyclohexyl, W is CH OH, R is C=O and S is O, NH, N(CH$_3$), CH$_2$ or a chemical bond linking R and T, then T is hydroxy(C$_1$-C$_4$)alkyl, CONH—(C$_1$-C$_4$)alkyl, hydrogen, trifluoroethyl, (C$_6$-C$_7$)cycloalkyl, (C$_6$-C$_7$)cycloalkylmethyl, phenyl, benzyl, amino(C$_2$-C$_5$)alkyl, O—(C$_1$-C$_2$)alkyl hydroxylamino, morpholino, 4-(C$_1$-C$_2$)alkylpiperazino or omega-di(C$_1$-C$_2$)alkylamino(C$_3$-C$_5$)alkyl.

2. A compound of claim 1, wherein Y is C=O, A is NH, Q is hydrogen, X is cyclohexyl, W is CH OH, R is C=O, T is benzyl or (C$_1$-C$_5$)alkyl and m and p are each 1.

3. The compound of claim 2, wherein M is 2-thienyl, R$_2$ is CH$_3$SCH$_2$—, S is O and T is i-propyl.

4. The compound of claim 2, wherein M is phenyl, R$_2$ is HOCH$_2$, S is O and T is i-propyl.

5. The compound of claim 2, wherein M is phenyl, R$_2$ is CH$_3$O(CH$_2$)$_2$—, S is O and T is i-propyl.

6. The compound of claim 2, wherein M is phenyl, R$_2$ is CH$_3$SCH$_2$—, S is O and T is benzyl.

7. The compound of claim 2, wherein M is 4-hydroxyphenyl, R$_2$ is CH$_3$SCH$_2$—, S is O and T is i-propyl.

8. The compound of claim 2, wherein M is 4-methoxyphenyl, R$_2$ is n-butyl, S is O and T is methyl.

9. The compound of claim 2, wherein M is phenyl, R$_2$ is CH$_3$OCH$_2$—, S is O and T is i-propyl.

10. The compound of claim 2, wherein M is phenyl, R$_2$ is CH$_3$CH$_2$OCH$_2$—, S is O and T is i-propyl.

11. A method of treating hypertension in a mammal which comprises administering to said mammal an antihypertensive effective amount of a compound according to claim 1.

12. A pharmaceutical composition comprising an antihypertensive effective amount of a compound according to claim 1 and a pharmaceutcally acceptable diluent or carrier.

* * * * *

UNITED STATES PATENT AND TRADEMARK OFFICE
CERTIFICATE OF CORRECTION

PATENT NO. : 4,935,405

DATED : June 19, 1990

INVENTOR(S) : Dennis J. Hoover, Robert L. Rosati and Ronald T. Wester

It is certified that error appears in the above-identified patent and that said Letters Patent is hereby corrected as shown below:

Claim 1, column 91, line 28, "W is CH  OH" should read
--W is CH||||OH--;

Claim 1, column 91, line 37, "$_1$-C$_4$)alkyl, is CH$_2$," should read
--$_1$-C$_4$)alkyl, S is --;

Claim 1, column 92, line 3, "W is CH  OH" should read
--W is CH||||OH--.

Signed and Sealed this

Seventeenth Day of September, 1991

Attest:

HARRY F. MANBECK, JR.

*Attesting Officer*  *Commissioner of Patents and Trademarks*